US010186672B2

(12) United States Patent
Xia et al.

(10) Patent No.: US 10,186,672 B2
(45) Date of Patent: Jan. 22, 2019

(54) ORGANIC ELECTROLUMINESCENT MATERIALS AND DEVICES

(71) Applicant: Universal Display Corporation, Ewing, NJ (US)

(72) Inventors: Chuanjun Xia, Lawrenceville, NJ (US); Bert Alleyne, Newtown, PA (US); Raymond C. Kwong, Fo Tan (HK); James Fiordeliso, Yardley, PA (US); Michael S. Weaver, Princeton, NJ (US); Nasrin Ansari, Princeton, NJ (US); Alan Deangelis, Pennington, NJ (US); Dinesh Rayabarapu, Overland Park, KS (US); Vadim Adamovich, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

(21) Appl. No.: 15/467,724

(22) Filed: Mar. 23, 2017

(65) Prior Publication Data

US 2017/0194577 A1 Jul. 6, 2017

Related U.S. Application Data

(60) Division of application No. 14/791,741, filed on Jul. 6, 2015, now Pat. No. 9,630,983, which is a continuation of application No. 13/968,551, filed on Aug. 16, 2013, now Pat. No. 9,076,973, which is a continuation of application No. 13/062,141, filed as application No. PCT/US2009/055890 on Sep. 3, 2009, now Pat. No. 8,519,384, which is a continuation-in-part of application No. PCT/US2009/052045, filed on Jul. 29, 2009.

(60) Provisional application No. 61/093,967, filed on Sep. 3, 2008, provisional application No. 61/140,459, filed on Dec. 23, 2008, provisional application No. 61/229,088, filed on Jul. 28, 2009.

(51) Int. Cl.
| | |
|---|---|
| *C07F 15/00* | (2006.01) |
| *H01L 51/00* | (2006.01) |
| *C09K 11/06* | (2006.01) |
| *H05B 33/14* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1007* (2013.01); *C09K 2211/1011* (2013.01); *C09K 2211/1059* (2013.01); *C09K 2211/1066* (2013.01); *C09K 2211/1074* (2013.01); *C09K 2211/1092* (2013.01); *C09K 2211/185* (2013.01); *H01L 51/006* (2013.01); *H01L 51/0054* (2013.01); *H01L 51/0074* (2013.01); *H01L 51/0081* (2013.01); *H01L 51/5016* (2013.01)

(58) Field of Classification Search
CPC ........................................................ C07F 15/00
USPC ................................................................ 546/2
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,005,522 | B2 | 2/2006 | Deaton |
| 7,087,321 | B2 | 8/2006 | Kwong et al. |
| 7,090,928 | B2 | 8/2006 | Thompson et al. |
| 7,125,998 | B2 | 10/2006 | Stossel et al. |

(Continued)

FOREIGN PATENT DOCUMENTS

| | | |
|---|---|---|
| EP | 0650955 | 5/1995 |
| EP | 1239526 | 9/2002 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Charanjit Aulakh
(74) *Attorney, Agent, or Firm* — Duane Morris LLP

(57) ABSTRACT

Methods of making novel organic compounds containing a twisted aryl group are provided. In particular, the compounds provided contain a 2-phenylpyridine ligand having a twisted aryl group on the pyridine portion of the ligand. The compounds may be used in organic light emitting devices, particularly as emitting dopants. Devices comprising the compounds containing twisted aryl may demonstrate improved color, efficiency, stability and manufacturing.

5 Claims, 9 Drawing Sheets

(56) References Cited

U.S. PATENT DOCUMENTS

| | | |
|---|---|---|
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,635,526 B2 | 12/2009 | Stossel et al. |
| 8,119,255 B2 | 2/2012 | Xia |
| 8,778,508 B2 * | 7/2014 | Kwong .............. H01L 51/0085 428/690 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0088728 A1 | 4/2006 | Kwong et al. |
| 2006/0134459 A1 | 6/2006 | Huo et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0003789 A1 | 1/2007 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0124805 A1 | 5/2009 | Alleyne et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |

FOREIGN PATENT DOCUMENTS

| | | |
|---|---|---|
| EP | 1725079 | 11/2006 |
| EP | 2034538 | 3/2009 |
| JP | 2001357977 | 12/2001 |
| JP | 2004-355898 | 12/2004 |
| JP | 200511610 | 1/2005 |
| JP | 2006151888 | 6/2006 |
| JP | 2007123392 | 5/2007 |
| JP | 2007254297 | 10/2007 |
| JP | 2008074939 | 4/2008 |
| JP | 2008-531684 | 8/2008 |
| TW | 201016665 | 5/2010 |
| WO | 2001039234 | 5/2001 |
| WO | 2002002714 | 1/2002 |
| WO | 200215645 | 2/2002 |
| WO | 2003040257 | 5/2003 |
| WO | 2003060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005/083033 | 9/2005 |
| WO | 2005089025 | 9/2005 |
| WO | 2005/097943 | 10/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006/093466 | 9/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007/056330 | 5/2007 |
| WO | 2007063754 | 6/2007 |
| WO | 2007063796 | 6/2007 |
| WO | 2008056746 | 5/2008 |
| WO | 2008073440 | 6/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009073246 | 6/2009 |
| WO | 2009086028 | 7/2009 |
| WO | 2009100991 | 8/2009 |
| WO | 2010027583 | 3/2010 |
| WO | 2010028151 | 3/2010 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

(56) References Cited

OTHER PUBLICATIONS

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing NΛCΛN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergåd et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Notice of Reasons for Rejection dated May 23, 2016 for corresponding JP Patent Application No. 2015-161797.
Korean Office Action dated Feb. 11, 2016 for corresponding KR Application No. 10-2015-7033289.
U.S. Appl. No. 61/093,967, filed Sep. 3, 2008.
U.S. Appl. No. 61/140,459, filed Dec. 23, 2008.
U.S. Appl. No. 61/229,088, filed Jul. 28, 2009.
U.S. Appl. No. 60/940,310, filed May 25, 2007.
International Search Report corresponding to the PCT/Us2009/055890 application filed Sep. 3, 2009.
International Search Report corresponding to the PCT/US09/52045 application filed Jul. 29, 2009.
Bettington, Sylvia, "The synthesis and photophysical studies of cyclometalated iridium (III) complexes," Durham E-Theses, University of Durham, Department of Chemistry, Dec. 2003.

* cited by examiner

Compound 1

Compound 2

Formula I  Formula II

ORGANIC ELECTROLUMINESCENT MATERIALS AND DEVICES

CROSS-REFERENCE TO RELATED APPLICATIONS

This application is a divisional application of co-pending U.S. patent application Ser. No. 14/791,741, filed Jul. 6, 2015, which is a continuation application of U.S. patent application Ser. No. 13/968,551, filed Aug. 16, 2013, now U.S. Pat. No. 9,076,973 issued on Jul. 7, 2015, which is a continuation application of U.S. patent application Ser. No. 13/062,141, filed May 20, 2011, now U.S. Pat. No. 8,519,384 issued on Aug. 27, 2013, which is a U.S. national phase application filed under 35 U.S.C. § 371 of International Application No. PCT/US2009/55890, filed Sep. 3, 2009, which is a continuation-in-part of application No. PCT/US2009/052045, filed on Jul. 29, 2009, and claims priority to provisional application No. 61/093,967, filed on Sep. 3, 2008, provisional application No. 61/140,459, filed on Dec. 23, 2008, and provisional application No. 61/229,088, filed on Jul. 28, 2009.

FIELD OF THE INVENTION

The present invention relates to organic materials that may be advantageously used in organic light emitting devices. More particularly, the present invention relates to a method of making organic materials for such devices, as well as novel organic materials.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure:

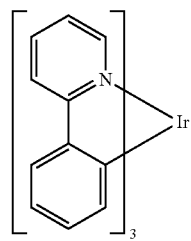

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A method is provided for making heteroleptic Ir(III) complexes having extended conjugation. The method, comprising:

reacting

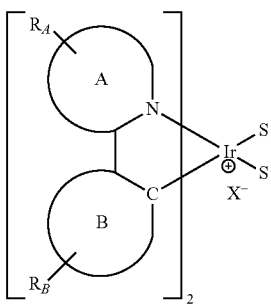

with

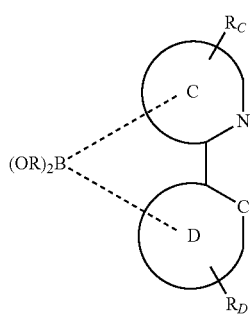

to form

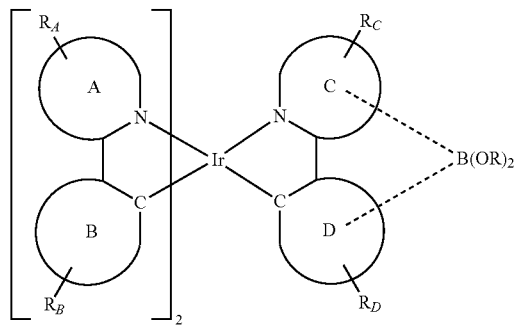

S is a neutral ligand. X is a counterion. Preferably, S is selected from the group consisting of triflate, tosylate, trifluoroacetate, tetrafluoroborate, and hexafluorophosphate. A and B are each independently a 5 or 6-membered aromatic or heteroaromatic ring, and A-B represents a bonded pair of aromatic or heteroaromatic rings coordinated to the iridium via a nitrogen atom on ring A and an $sp^2$ hybridized carbon atom on ring B. C and D are each independently a 5 or 6-membered aromatic or heteroaromatic ring, and C-D represents a bonded pair of aromatic or heteroaromatic rings coordinated to the iridium via a nitrogen ring atom on ring C and an $sp^2$ hybridized carbon atom on ring D. $R_A$, $R_B$, $R_C$, and $R_D$ are each independently selected from the group consisting of no substitution, alkyl, heteroalkyl, aryl, or heteroaryl groups. Each of $R_A$, $R_B$, $R_C$, and $R_D$ represent one or more substituents. Preferably, $R_A$, $R_B$, $R_C$, and $R_D$ are selected from the group consisting of benzene, pyrimidine, pyridine, thiophene, thianapthene, fluorine, carbazole, and dibenzothiophene. R is an alkyl, heteroalkyl, or perfluoroalkyl group and the two $R_S$ are optionally joined to form a cycle.

Additionally, phosphorescent emissive materials are provided. The materials are heteroleptic complexes with extended conjugation on the heterocyclic ring. The materials may be advantageously used in organic light emitting devices. In particular, the materials may be useful as the emissive dopant of such devices. The materials are selected from the group consisting of:

Compound 1

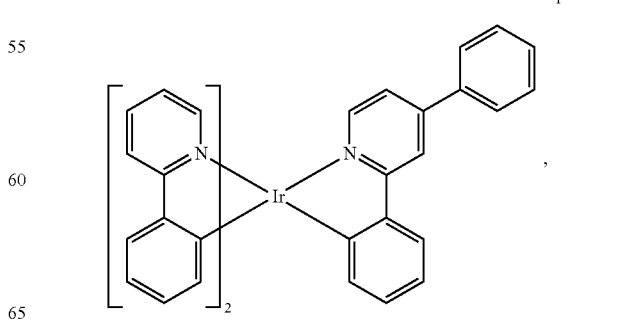

Compound 2

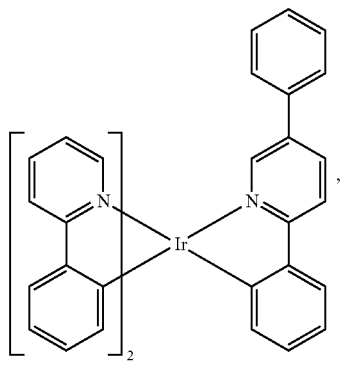

Compound 3

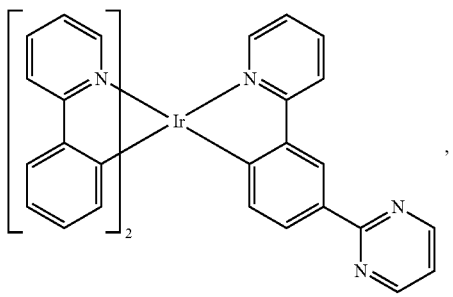

Compound 4

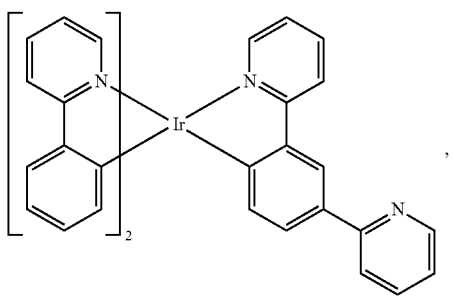

Compound 5

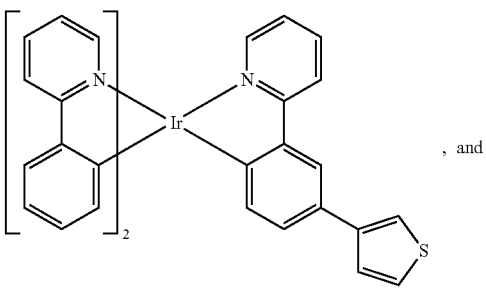

, and

Compound 6

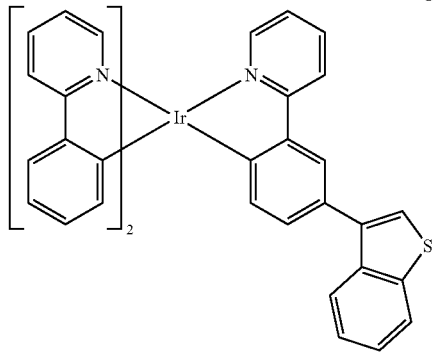

In one aspect, Compound 1 may be preferred. In another aspect, Compound 2 may be preferred.

Additionally, an organic light emitting device is provided. The device has an anode, a cathode, and an organic layer disposed between the anode and the cathode, where the organic layer comprises a compound selected from Compounds 1-6. The organic layer may further comprise a host. Preferably, the host includes a triphenylene group. More preferably, the host includes a triphenylene further substituted with terphenyl. Most preferably, the host is H1.

A consumer product is also provided. The product contains a device that has an anode, a cathode, and an organic layer disposed between the anode and the cathode, where the organic layer further comprises a compound selected from Compounds 1-6.

Heteroleptic iridium compounds are provided, which may be advantageously used in organic light emitting devices. The heteroleptic compounds are selected from the group consisting of:

Compound 8

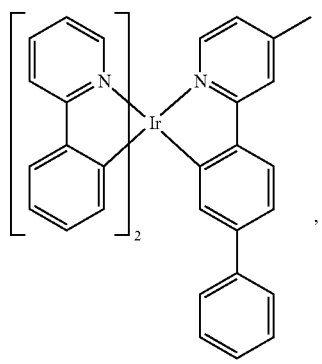

Compound 9

Compound 10

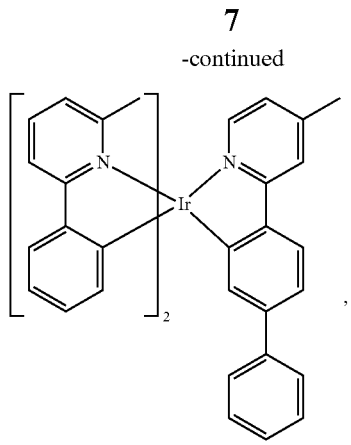

Compound 11

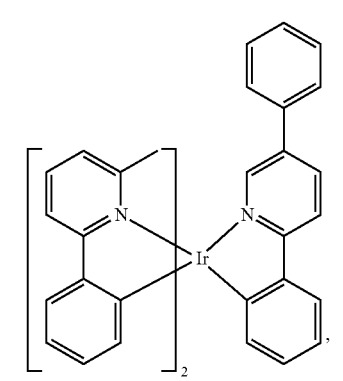

Compound 12

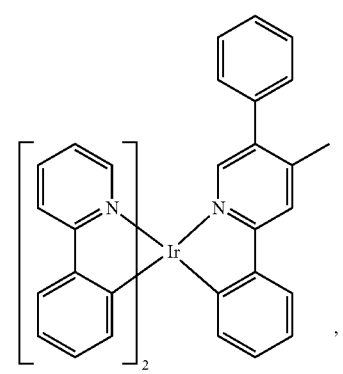

Compound 13

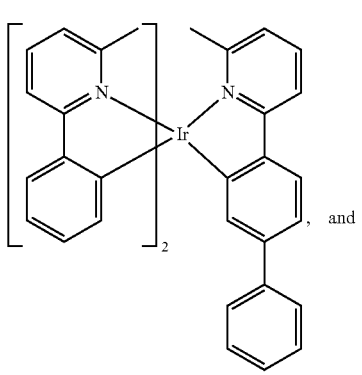, and

Compound 14

In one aspect, Compound 8 may be preferred. In another aspect, Compound 9 may be preferred. In yet another aspect, Compound 10 may be preferred. In a further aspect, Compound 11 may be preferred. In yet another aspect, Compound 12 may be preferred. In a further aspect, Compound 13 may be preferred. In yet another aspect, Compound 14 may be preferred.

Additionally, an organic light emitting device is provided. The device has an anode, a cathode, and an organic layer disposed between the anode and the cathode, where the organic layer comprises a compound selected from Compounds 8-14. The organic layer may further comprise a host having a triphenylene group further substituted with an aryl or a heteroaryl. Preferably, the host contains a triphenylene group further substituted with a terphenyl or a dibenzothiophene. More preferably, the host is H1 or H2.

A consumer product is also provided. The product contains a device that has an anode, a cathode, and an organic layer disposed between the anode and the cathode, where the organic layer further comprises a compound selected from Compounds 8-14.

Additionally, a method for making heteroleptic compounds without significant ligand scrambling is provided. The method, comprising:

reacting with

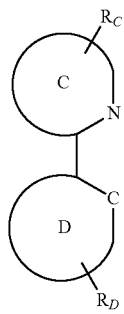

to form

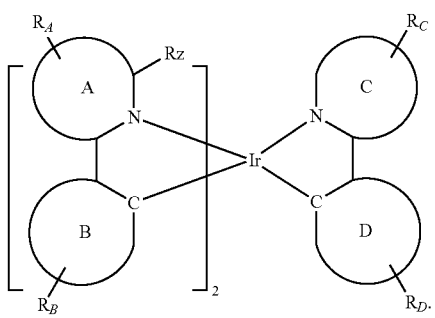

S is a neutral ligand. X is a counterion. Preferably, X is selected from the group consisting of triflate, tosylate, trifluoroborate, and hexafluorophosphate. A and B are each independently a 5 or 6-membered aromatic or heteroaromatic ring, and A-B represents a bonded pair of aromatic or heteroaromatic rings coordinated to the iridium via a nitrogen atom on ring A and an sp² hybridized carbon atom on ring B. C and D are each independently a 5 or 6-membered aromatic or heteroaromatic ring, and C-D represents a bonded pair of aromatic or heteroaromatic rings coordinated to the iridium via a nitrogen ring atom on ring C and an sp² hybridized carbon atom on ring D. $R_A$, $R_B$, $R_C$, and $R_D$ are each independently selected from the group consisting of no substitution, alkyl, heteroalkyl, aryl, or heteroaryl groups, and each of $R_A$, $R_B$, $R_C$, and $R_D$ represent one or more substituents. Preferably, $R_A$, $R_B$, $R_C$, and $R_D$ are selected from the group consisting of benzene, pyrimidine, pyridine, thiophene, thianaphthene, fluorine, carbazole, and dibenzothiophene. $R_Z$ is not H. Preferably, $R_Z$ is methyl.

A heteroleptic compound having the formula $Ir(L_{A-B})_2(L_{C-D})$ is provided. $L_{A-B}$ is

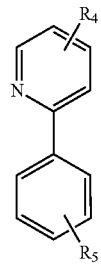

$L_{C-D}$ is selected from the group consisting of

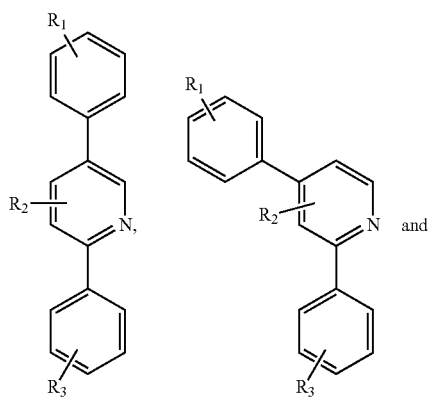

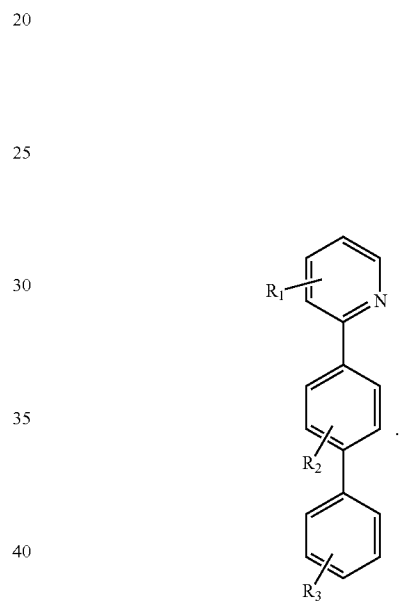

$R_1$, $R_2$, $R_3$, $R_4$ and $R_5$ are each independently selected from the group consisting of hydrogen and alkyl, and each of $R_1$, $R_2$, $R_3$, $R_4$ and $R_5$ may represent mono, di, tri, tetra, or penta substitutions. Preferably, $R_1$, $R_2$, $R_3$, $R_4$ and $R_5$ are each independently hydrogen and methyl. More preferably, $L_{C-D}$ is selected from the group consisting of:

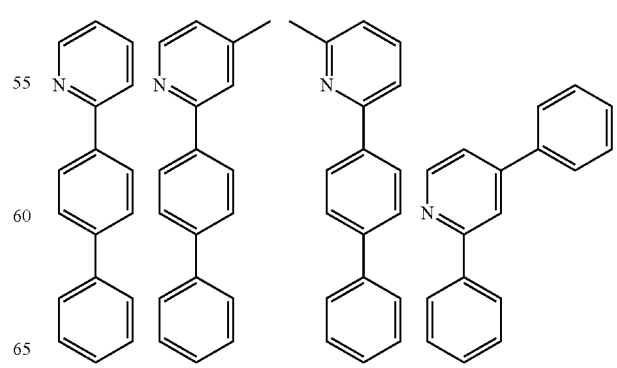

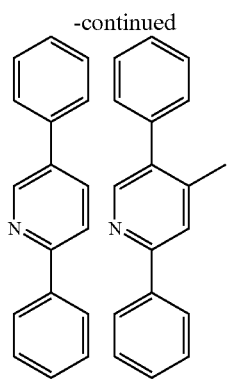

Novel phosphorescent organic materials are provided. The organic materials are compounds containing at least one ligand having an alkyl substituent and an aryl substituent such that the substituent aryl is twisted out of plane (i.e., twisted aryl in this document) more than the usual unsubstituted phenyl-phenyl. The compounds may be advantageously used in organic light emitting devices. In particular, the compounds may be useful as an emitting dopant in such devices.

Compounds are provided, the compounds comprising a ligand L having the structure:

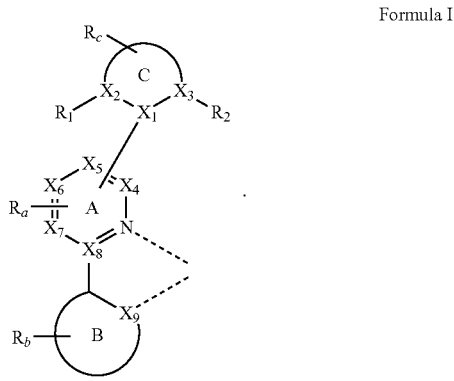

Formula I

B and C are each independently a 5 or 6-membered carbocyclic or heterocyclic ring. A-B represents a bonded pair of carbocyclic or heterocyclic rings coordinated to a metal M via a nitrogen atom on ring A and a sp² hybridized carbon atom on ring B. A-C represents a bonded pair of carbocyclic and heterocyclic rings. $R_a$, $R_b$, and $R_c$ may represent mono, di, tri, or tetra substitutions. $R_a$, $R_b$, and $R_c$ are independently selected from the group consisting of hydrogen, alkyl, alkoxy, amino, alkenyl, alkynyl, arylkyl, aryl, and heteroaryl. $X_1$, $X_2$, $X_3$, $X_4$, $X_5$, $X_6$, $X_7$, $X_8$, and $X_9$ are independently selected from carbon and nitrogen. Preferably, A is pyridine. $R_1$ and $R_2$ are independently selected from the group consisting of hydrogen, alkyl, alkoxy, amino, alkenyl, alkynyl, arylkyl, aryl, and heteroaryl. At least one of $R_1$, $R_2$, and the $R_a$ substituents adjacent to Ring C is not hydrogen. Preferably, only one of $R_1$, $R_2$, and the $R_a$ substituents adjacent to C is not hydrogen. Preferably, only one of $R_1$, $R_2$, and the $R_a$ substituents adjacent to C is alkyl. More preferably, only one of $R_1$, $R_2$, and the $R_a$ substituents adjacent to C is ethyl. Most preferably, only one of $R_1$, $R_2$, and the $R_a$ substituents adjacent to C is methyl. The ligand L is coordinated to the metal M having an atomic number greater than 40. Preferably, the metal M is Ir.

Examples of the compounds may include compounds having the structure:

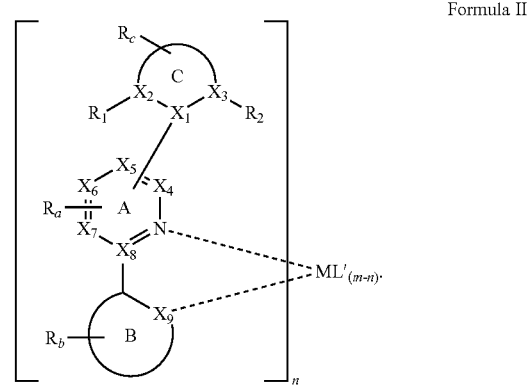

Formula II m is the oxidation state of the metal M. Preferably, the metal M is Ir. Preferably, A is pyridine. n is at least 1. L' is a monoanionic bidentate ligand. Preferably, only one of $R_1$, $R_2$, and the $R_a$ substituents adjacent to C is not hydrogen. Preferably, only one of $R_1$, $R_2$, and the $R_a$ substituents adjacent to C is alkyl. More preferably, only one of $R_1$, $R_2$, and the $R_a$ substituents adjacent to C is ethyl. Most preferably, only one of $R_1$, $R_2$, and the $R_a$ substituents adjacent to C is methyl.

Particular examples of compounds having Formula II are provided and include Compound 15-Compound 20. R is not hydrogen. Preferably, R is alkyl.

Specific examples of compounds having Formula II are provided, including Compound 21-Compound 37. In one aspect, Compounds 21, 22, 25, 29, 30, 31 and 34 may be preferred compounds.

In one aspect, compounds are provided wherein the compound is selected from the group consisting of:

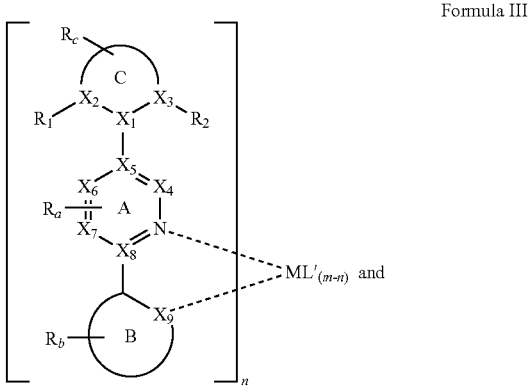

Formula III and

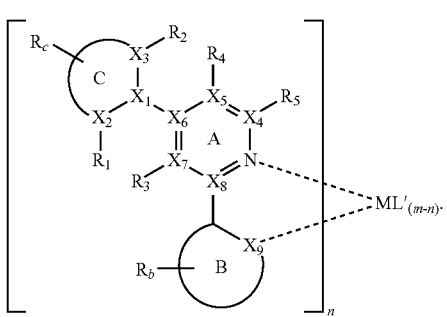

Formula IV

At least one of $R_1$, $R_2$, $R_3$, and $R_4$ is not hydrogen. $R_5$ is selected from the group consisting of hydrogen, alkyl, alkoxy, amino, alkenyl, alkynyl, arylkyl, aryl, and heteroaryl. Preferably, A is pyridine. In one aspect, $R_1$ and $R_2$ are hydrogen and one of $R_3$ and $R_4$ is alkyl. Exemplary compounds may include Compounds 21-24, 29-34, 36 and 37. In another aspect, one of $R_1$ and $R_2$ is alkyl and $R_3$ and $R_4$ are hydrogen. Exemplary compounds may include Compounds 25-28 and 35.

In another aspect, the compound is selected from the group consisting of:

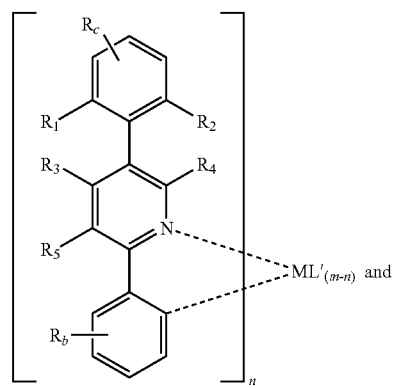

Formula V

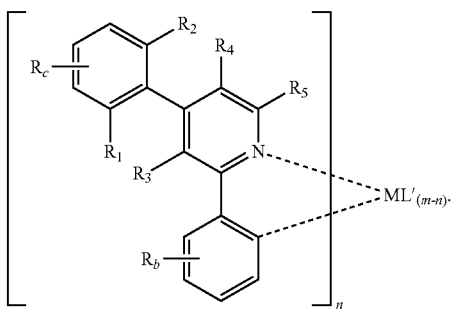

Formula VI

Compounds having Formula II include homoleptic compounds and heteroleptic compounds. Examples of homoleptic compound include Compounds 21-24 and 35. Examples of heteroleptic compounds include Compounds 25-34, 36 and 37.

In one aspect, compounds are provided having a ligand L' selected from the group consisting of:

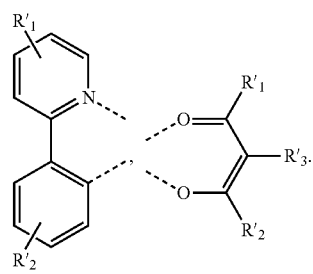

$R'_1$, $R'_2$ and $R'_3$ are independently selected from the group consisting of hydrogen, alkyl, alkoxy, amino, alkenyl, alkynyl, arylkyl, aryl, and heteroaryl.

In one aspect, compounds where the alkyl substituent (i.e., the alkyl substituent inducing the twist in the aryl substituent) is present on the pyridine ring of the ligand L are preferred. Preferably the compound is selected from the group consisting of Compounds 21-23, 29-31, 34, 36 and 37.

In another aspect, compounds where the alkyl substituent is para to the nitrogen of the pyridine ring may be especially preferred. Preferably, the compound is selected from the group consisting of Compounds 21, 22, 29-31, 34, 36 and 37.

An organic light emitting device is also provided. The device has an anode, a cathode, and an organic layer disposed between the anode and the cathode, where the organic layer comprises a compound having Formula I, as described above. Selections for the substituents described as preferred for the compounds having Formula I are also preferred for use in a device that comprises a compound having Formula I. These selections include those described for the metal M; the formulas II-VI; the substituents R, $R_1$, $R_2$, $R_3$, $R_4$, $R_5$, and $R_a$ substituents adjacent to C; the position of ring C; and rings A, B, and C.

In one aspect, the device comprises a compound having Formula II, as described above. Preferably, the metal M is Ir. Preferably, A is pyridine. In another aspect, the device comprises a compound having Formula III or Formula IV, as described above. Devices containing a compound wherein only one of $R_1$, $R_2$, and the $R_a$ substituents adjacent to C is alkyl may also be preferred. In yet another aspect, the device comprises a compound having Formula V or Formula VI, as described above. Certain devices are provided wherein the device contains a compound selected from the group consisting of Compound 21-Compound 37. Preferably, the device contains Compound 21, Compound 22, Compound 25, Compound 29, Compound 30, Compound 31 or Compound 34.

In one aspect, devices are provided wherein the organic layer is an emissive layer and the compound having the formula of Formula I is an emitting dopant. Moreover, the organic layer may further comprise a host. Preferably, the host has the structure:

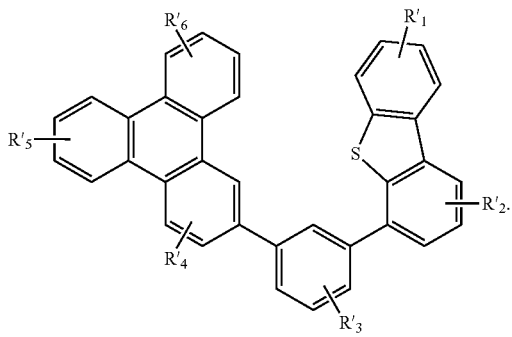

R'₁, R'₂, R'₃, R'₄, R'₅, and R'₆ are independently selected from the group consisting of hydrogen, alkyl, alkoxy, amino, alkenyl, alkynyl, arylkyl, aryl, and heteroaryl.

A consumer product comprising a device is also provided. The device comprises an anode, a cathode, and an organic layer disposed between the anode and the cathode, where the organic layer comprises a compound having Formula I, as described above. Selections for the substituents described as preferred for the compounds having Formula I are also preferred for use in a consumer product containing a device that comprises a compound having Formula I. These selections include those described for the metal M; the formulas II-VI; the substituents R, R₁, R₂, R₃, R₄, R₅, and $R_a$ substituents adjacent to C; the position of ring C; and rings A, B, and C.

Additionally, low temperature methods for making homoleptic compounds are provided. In particular, the methods are for making homoleptic Ir (III) compounds. These compounds may preferably contain a twisted aryl.

A first method for making a homoleptic Ir(III) complex is provided. The first method comprising:

reacting

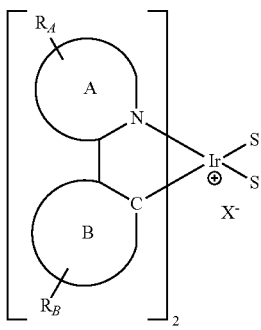

with

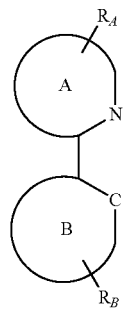

in the presence of a low boiling alcohol to form

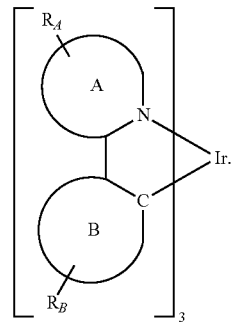

At least one of $R_A$ and $R_B$ is an alkyl group and the alkyl group is not adjacent to the nitrogen on the pyridine ring. S is a neutral ligand. X is a counterion. Preferably, X is triflate. A and B are each independently a 5 or 6-membered carbocyclic or heterocyclic ring. A-B represents a bonded pair of carbocyclic or heterocyclic rings coordinated to the iridium via a nitrogen atom on ring A and an sp² hybridized carbon atom on ring B. Each of $R_A$ and $R_B$ may represent mono, di, tri, or tetra substitutions. $R_A$ and $R_B$ are each independently selected from the group consisting of hydrogen, alkyl, alkoxy, amino, alkenyl, alkynyl, arylkyl, aryl, and heteroaryl.

In one aspect, the low boiling alcohol is selected from the group consisting of methanol, ethanol, n-propanol, isopropanol, n-butanol, a 1:1 ratio of ethanol and methanol, 2-methoxyethanol, and 2-ethoxyethanol. Preferably, the low boiling alcohol is selected from the group consisting of isopropanol which boils at 108° C., ethanol which boils at 78° C., and a 1:1 ratio of ethanol and methanol which has a boiling point between 65° C. and 78° C. More preferably, the low boiling alcohol is ethanol or a 1:1 ratio of ethanol and methanol. Most preferably, the low boiling alcohol is a 1:1 ratio of ethanol and methanol.

Preferably, A is:

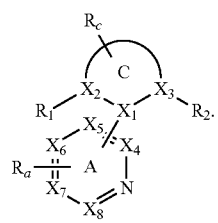

C is a 5 or 6-membered carbocyclic or heterocyclic ring. A-C represents a bonded pair of carbocyclic and heterocyclic rings. $R_A$ and $R_C$ may represent mono, di, tri, or tetra substitutions. $R_A$ and $R_C$ are independently selected from the group consisting of hydrogen, alkyl, alkoxy, amino, alkenyl, alkynyl, arylkyl, aryl, and heteroaryl. $X_1$, $X_2$, $X_3$, $X_4$, $X_5$, $X_6$, $X_7$, $X_8$, and $X_9$ are independently selected from carbon and nitrogen. $R_1$ and $R_2$ are independently selected from the group consisting of hydrogen, alkyl, alkoxy, amino, alkenyl, alkynyl, arylkyl, aryl, and heteroaryl. At least one of $R_1$, $R_2$, and the $R_a$ substituents adjacent to C is not hydrogen.

In one aspect, the first method comprises:
reacting

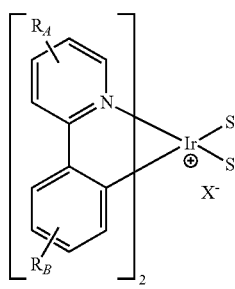

with

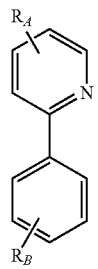

in the presence of a low boiling alcohol to form

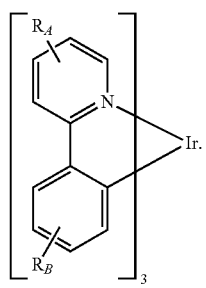

Specific compounds, including Compound 21, Compound 22, and Compound 24, may be formed using this method.

A second method for making homoleptic Ir (III) compounds is also provided. The second method comprises:
reacting

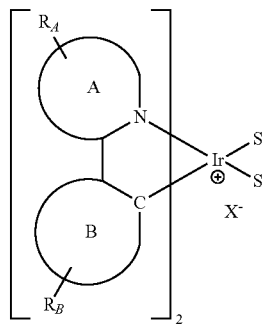

with

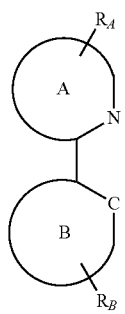

in the absence of solvent to form

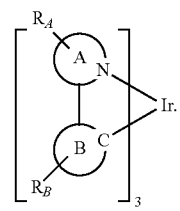

At least one of $R_A$ and $R_B$ is an alkyl group and the alkyl group is adjacent to the nitrogen on the pyridine ring. S is a neutral ligand. X is a counterion. Preferably, X is triflate. A and B are each independently a 5 or 6-membered carbocyclic or heterocyclic ring. A-B represents a bonded pair of carbocyclic or heterocyclic rings coordinated to the iridium via a nitrogen atom on ring A and an $sp^2$ hybridized carbon atom on ring B. Each of $R_A$ and $R_B$ may represent mono, di, tri, or tetra substitutions. $R_A$ and $R_B$ are each independently selected from the group consisting of hydrogen, alkyl, alkoxy, amino, alkenyl, alkynyl, arylkyl, aryl, and heteroaryl.

Preferably, A is:

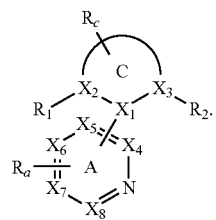

C is a 5 or 6-membered carbocyclic or heterocyclic ring. A-C represents a bonded pair of carbocyclic and heterocyclic rings. $R_A$ and $R_C$ may represent mono, di, tri, or tetra substitutions. $R_A$ and $R_C$ are independently selected from the group consisting of hydrogen, alkyl, alkoxy, amino, alkenyl, alkynyl, arylkyl, aryl, and heteroaryl. $X_1$, $X_2$, $X_3$, $X_4$, $X_5$, $X_6$, $X_7$, $X_8$, and $X_9$ are independently selected from carbon and nitrogen. $R_1$ and $R_2$ are independently selected from the group consisting of hydrogen, alkyl, alkoxy, amino, alkenyl, alkynyl, arylkyl, aryl, and heteroaryl. At least one of $R_1$, $R_2$, and the $R_a$ substituents adjacent to C is not hydrogen.

In one aspect, the second method comprises:
reacting

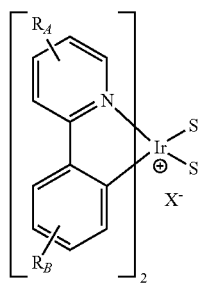

with

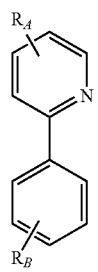

in the absence of solvent to form

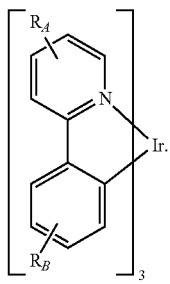

Specific compounds, including Compound 23, may be formed using this method.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
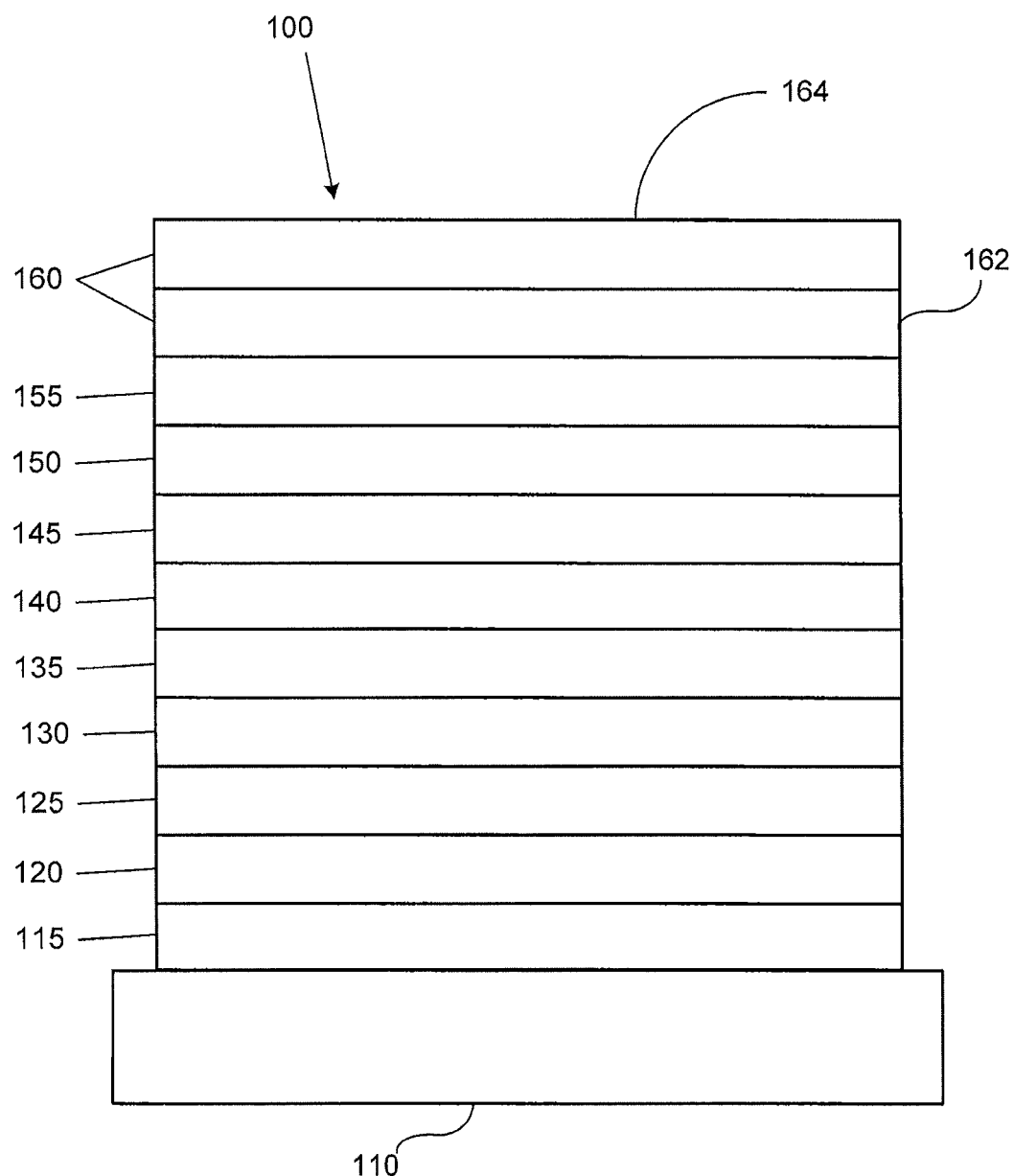
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
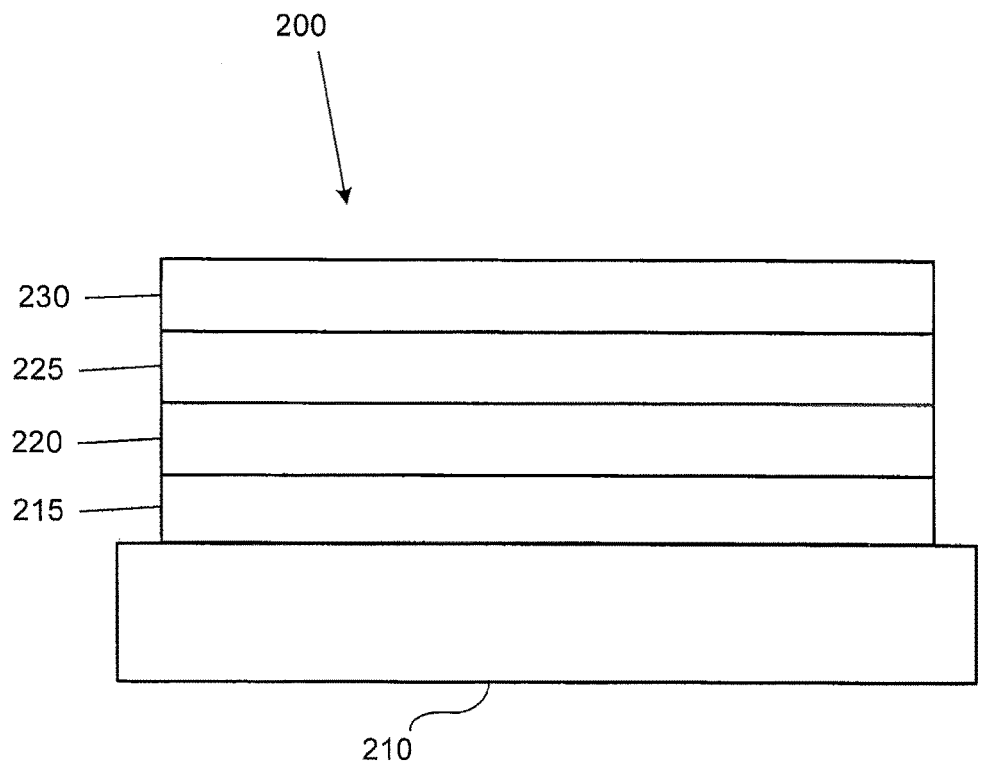
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Compounds are provided, comprising a heteroleptic Ir (III) complex having extended conjugation. In particular, the complex has extended conjugation on the heterocyclic ring which coordinates to the metal through nitrogen. Heteroleptic iridium complexes are of great interest because their photophysical, thermal, and electronic properties can be tuned according to the ligands that are attached to the metal center. One advantage to using heteroleptic iridium complexes is that they offer improved device lifetime and a lower sublimation temperature, therefore offering improved manufacturing, as compared to homoleptic Ir (III) complexes. For example, a heteroleptic complex containing 2-phenylpyridine and 2-(biphenyl-3-yl)pyridine, has shown an improved lifetime compared to a related homoleptic complex. Further, the sublimation temperature of the heteroleptic complex is almost 70° C. lower than the homoleptic complex. See, U.S. Provisional Application No. 60/940,310. Heteroleptic complexes which demonstrate improved stability and low sublimation temperatures, such as those disclosed herein, are highly desirable for use in OLEDs. In particular, the heteroleptic Ir (III) complexes may be especially desirable for use in white organic light emitting devices (WOLEDs).

The existing synthetic methods for making many heteroleptic iridium complexes may not be practical. In particular, existing synthetic routes include the halogenation of iridium complexes and further functionalized (see, Stossel et al., Rhodium complexes and iridium complexes, 2005, EP1504015B1; Stossel et al., Rhodium and iridium complexes, 2006, U.S. Pat. No. 7,125,998), the use of boronic ester substituted iridium complexes generated from halogenated complexes and further functionalized (see, Kwong et al., Method for synthesis of iridium (III) complexes with sterically demanding ligands, 2006, U.S. application Ser. No. 12/044,848), and the low temperature BuLi/ZnCl$_2$ method (see, Huo et al, OLEDs with mixed ligand cyclometallated complexes, 2006, US20060134459A1). The low temperature BuLi/ZnCl$_2$ method, for example, produces mer-isomers of the complex, which are not normally desired, and thus must then be converted to the useful fac-isomer of the complex. See, Huo et al, OLEDs with mixed ligand cyclometallated complexes, 2006, US20060134459A1. Thus, this method may not be practical for large scale synthesis of the complex. While offering improved yield, the method that involves converting a brominated iridium complex to a boronic ester to ultimately yield the final product is indirect. See, Kwong et al., Method for synthesis of iridium (III) complexes with sterically demanding ligands, 2006, U.S. application Ser. No. 12/044, 848. Therefore, it is highly desirable to provide a more practical and direct synthetic method for making heteroleptic Ir (III) complexes.

The method, as described herein, can be used to make heteroleptic Ir (III) complexes that may be advantageously used in OLEDs and, in particular, WOLEDs. For example, the method described herein can be used to make especially desirable heteroleptic Ir (III) complexes such as Compound 1, Compound 2 and Compound 7.

A method for making Ir (III) heteroleptic complexes having extended conjugation, the method comprising reacting

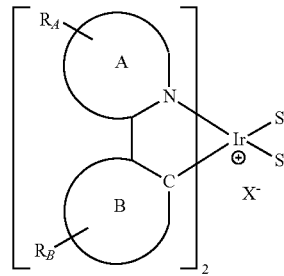

with

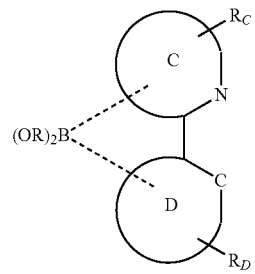

to form

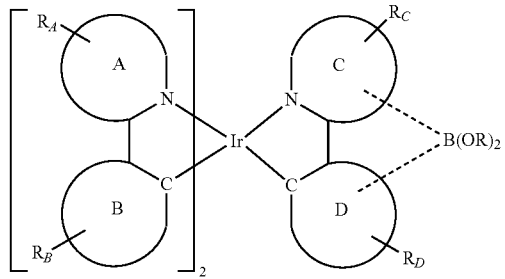

where S is a neutral ligand. X is a counterion. A and B are each independently a 5 or 6-membered aromatic or heteroaromatic ring, and A-B represents a bonded pair of aromatic or heteroaromatic rings coordinated to the iridium via a nitrogen atom on ring A and an sp$^2$ hybridized carbon atom on ring B. C and D are each independently a 5 or 6-membered aromatic or heteroaromatic ring, and C-D represents a bonded pair of aromatic or heteroaromatic rings coordinated to the iridium via a nitrogen ring atom on ring C and an sp$^2$ hybridized carbon atom on ring D. $R_A$, $R_B$, $R_C$, and $R_D$ are each independently selected from the group consisting of no substitution, alkyl, heteroalkyl, aryl, or heteroaryl groups. Each of $R_A$, $R_B$, $R_C$, and $R_D$ represent one or more substituents. R is an alkyl, heteroalkyl, or perfluoroalkyl group and the two $R_S$ are optionally joined to form a cycle.

In one aspect of the method, the counterion X is selected from the group consisting of triflate, tosylate, trifluoroacetate, tetrafluoroborate, and hexafluorophosphate.

In one aspect, $R_A$, $R_B$, $R_C$, and $R_D$ are selected from the group consisting of benzene, pyrimidine, pyridine, thiophene, thianaphthene, fluorine, carbazole, and dibenzothiophene.

In another aspect, the method includes reacting

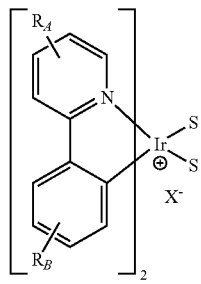

with

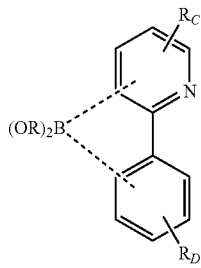

to form

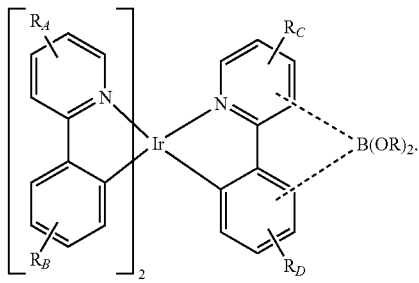

In one aspect of the method, the group $B(OR)_2$ is attached to ring C. In another aspect, the group $B(OR)_2$ is attached to ring D. In a particular aspect of the method, the group $B(OR)_2$ is

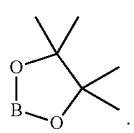

In one aspect, the method includes reacting

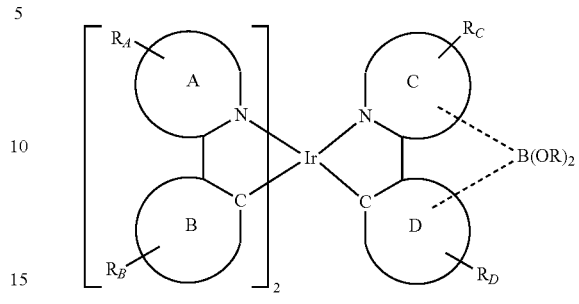

with RX to form

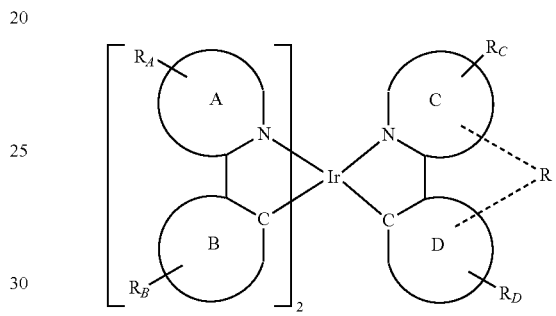

wherein R is aryl or heteroaryl and X is selected from the group consisting of I, Br, Cl, and OTf.

In one aspect, the method includes reacting

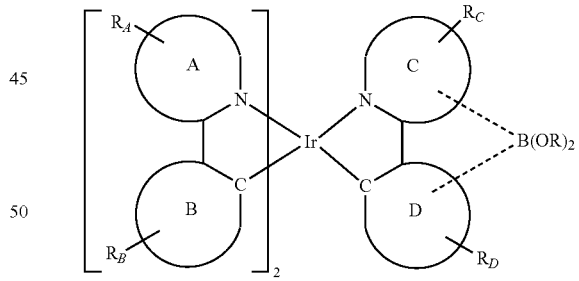

with

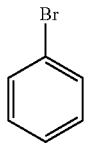

to form
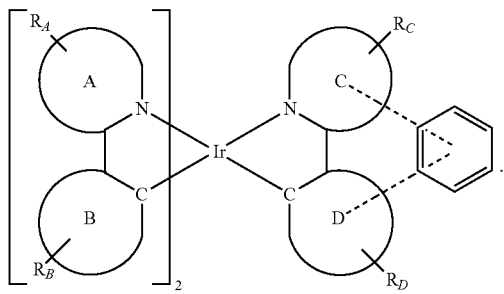
In a certain aspect of the method, the complex
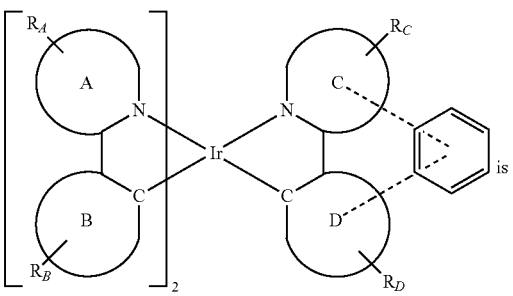 is
Compound 1
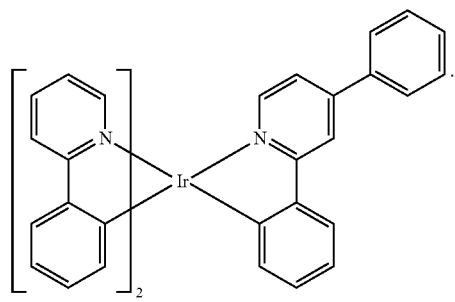
In another aspect, the complex is
Compound 7
In yet another aspect, the complex is
Compound 2
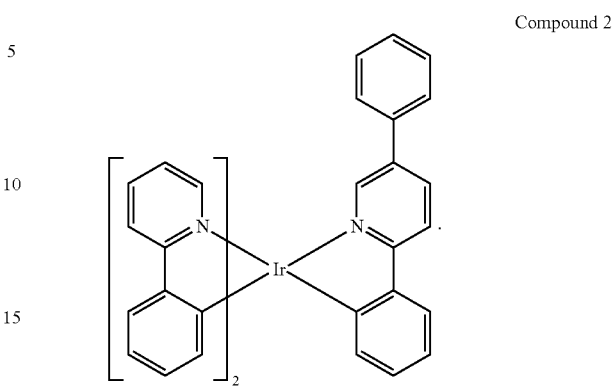
In another aspect, the method includes reacting
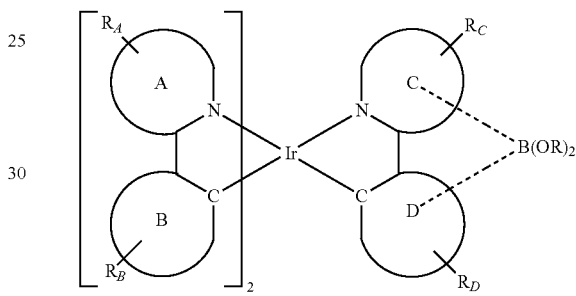
with
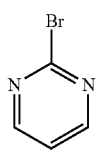
to form
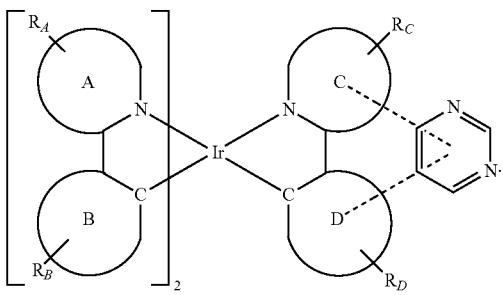

In a certain aspect of the method, the complex
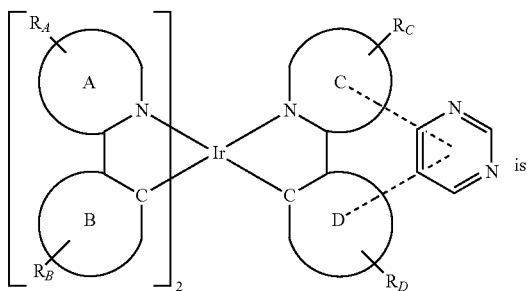
is
to form
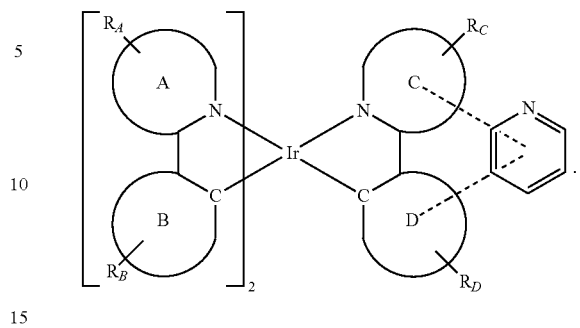
In a certain aspect, the complex
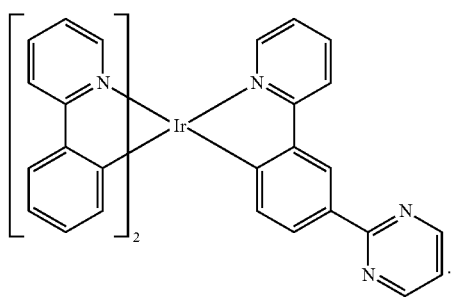
is
Compound 3
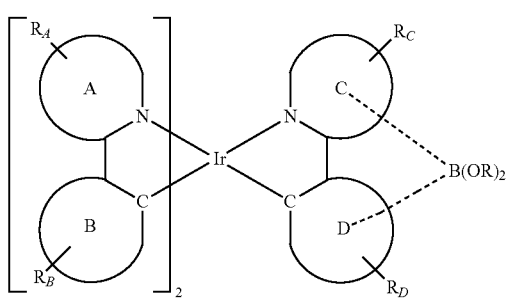
In another aspect, the method includes reacting
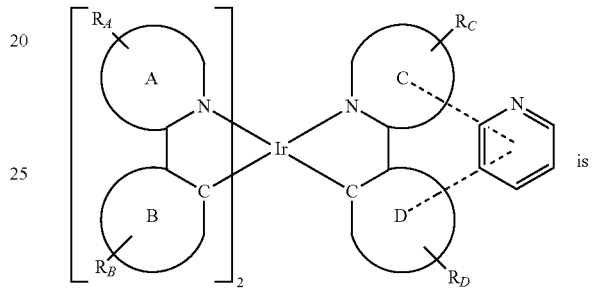
Compound 4
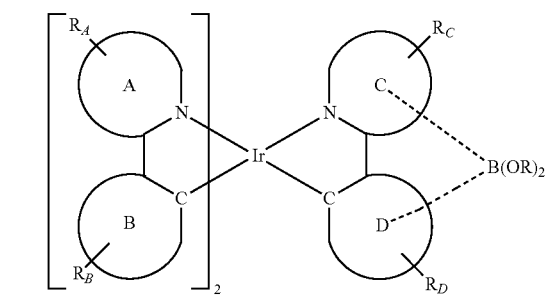
In another aspect, the method includes reacting
with
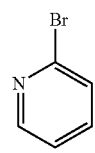
with
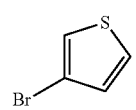

to form
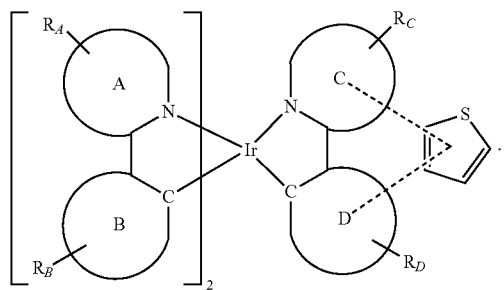
In a certain aspect, the complex
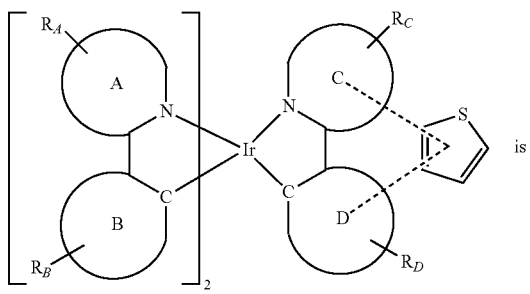
is
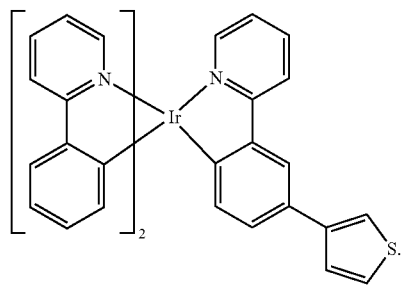
Compound 5
In yet another aspect, the method includes reacting
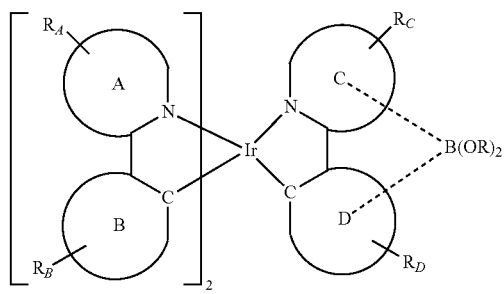
with
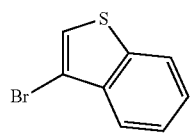
to form
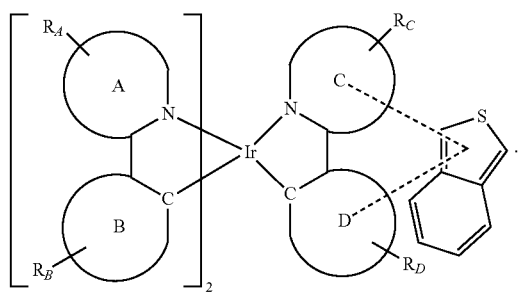
In a certain aspect of the method, the complex
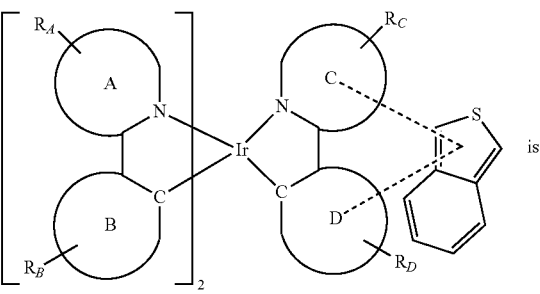
is
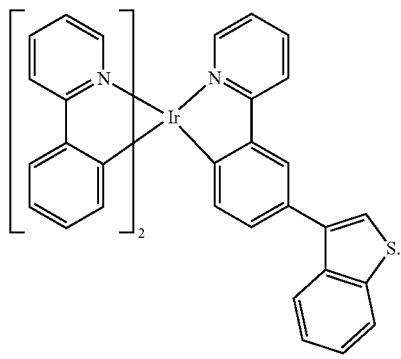
Compound 6

In another aspect, the method further includes reacting

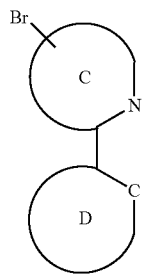

with

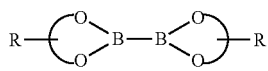

to form

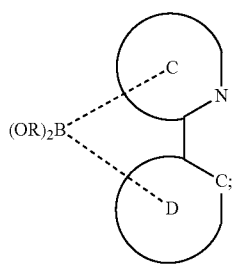

and reacting

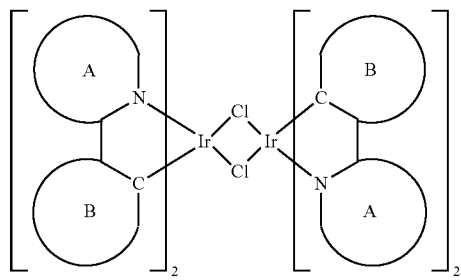

with AgX to form

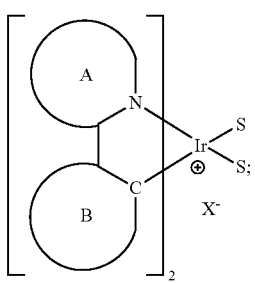

and then reacting

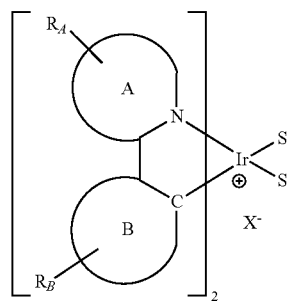

with

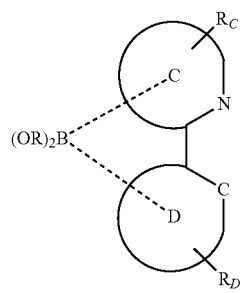

to form

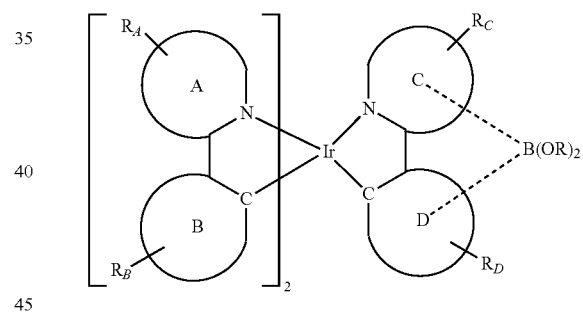

Additionally, phosphorescent emissive compounds are provided. In particular, the compounds are Ir (III) heteroleptic complexes having extended conjugation on the heterocyclic ring which coordinates to the metal through nitrogen. The compounds provided have the formula selected from the group consisting of:

Compound 1

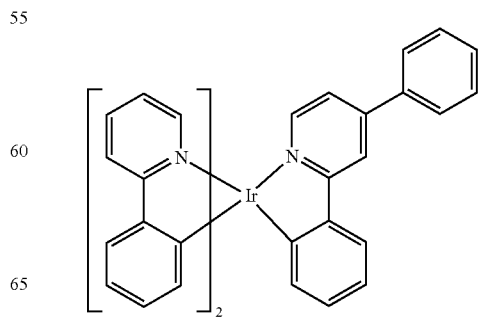

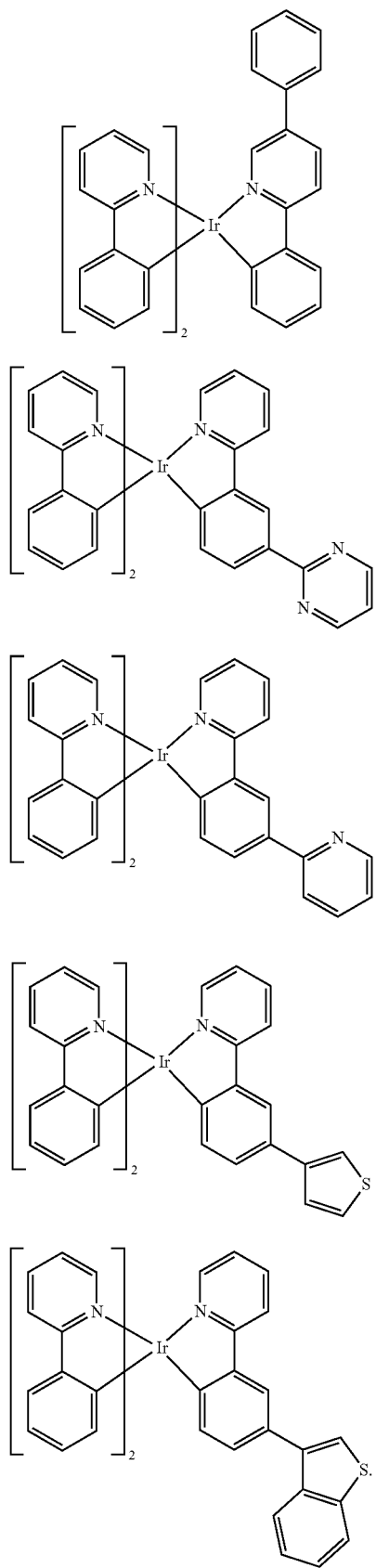

Compound 2

Compound 3

Compound 4

Compound 5

Compound 6

Certain compounds may be particularly beneficial. In one aspect, preferably the compound is Compound 1. In another aspect, preferably the compound is Compound 2.

Heteroleptic iridium compounds are provided, which may be advantageously used in organic light emitting devices. In particular, the compounds may be useful as the emissive dopant of such devices. The heteroleptic compounds are selected from the group consisting of:

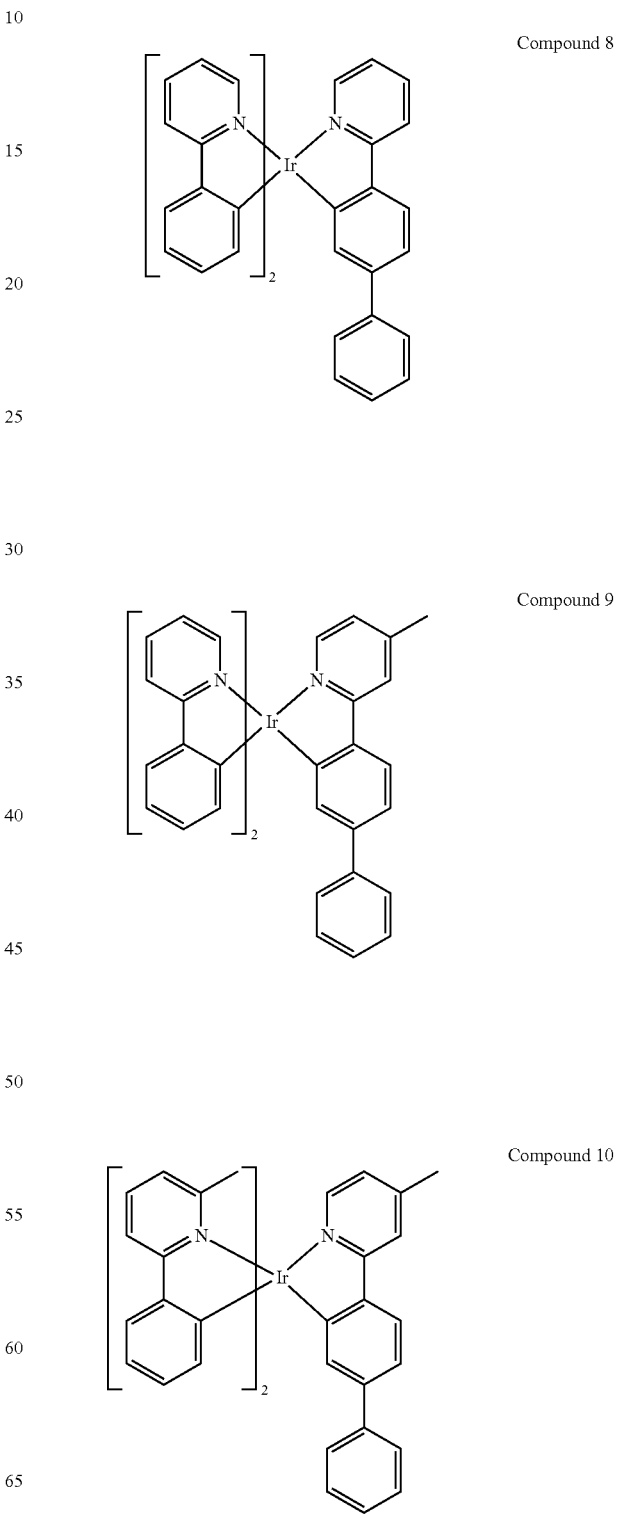

Compound 8

Compound 9

Compound 10

-continued

Compound 11

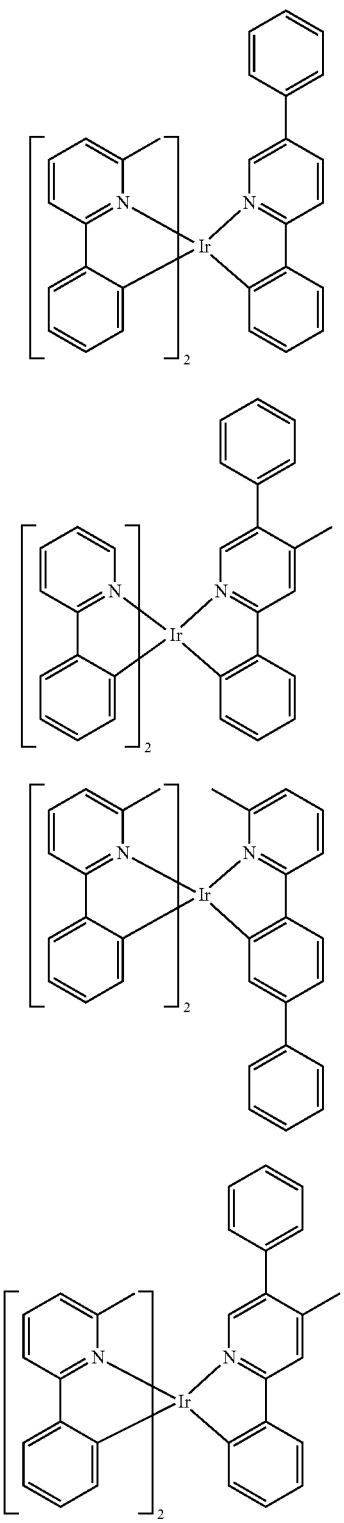

Compound 12

Compound 13

Compound 14

Certain compounds may be particularly beneficial. In one aspect, preferably the compound is Compound 8. In another aspect, preferably the compound is Compound 9. In yet another aspect, preferably the compound is Compound 10. In a further aspect, preferably the compound is Compound 11. In yet another aspect, preferably the compound is Compound 12. In a further aspect, preferably the compound is Compound 13. In yet another aspect, preferably the compound is Compound 14.

Additionally, an organic light emitting device is provided, the device comprising an anode, a cathode, and an organic layer disposed between the anode and the cathode, and the organic layer further comprising a compound selected from the group consisting of:

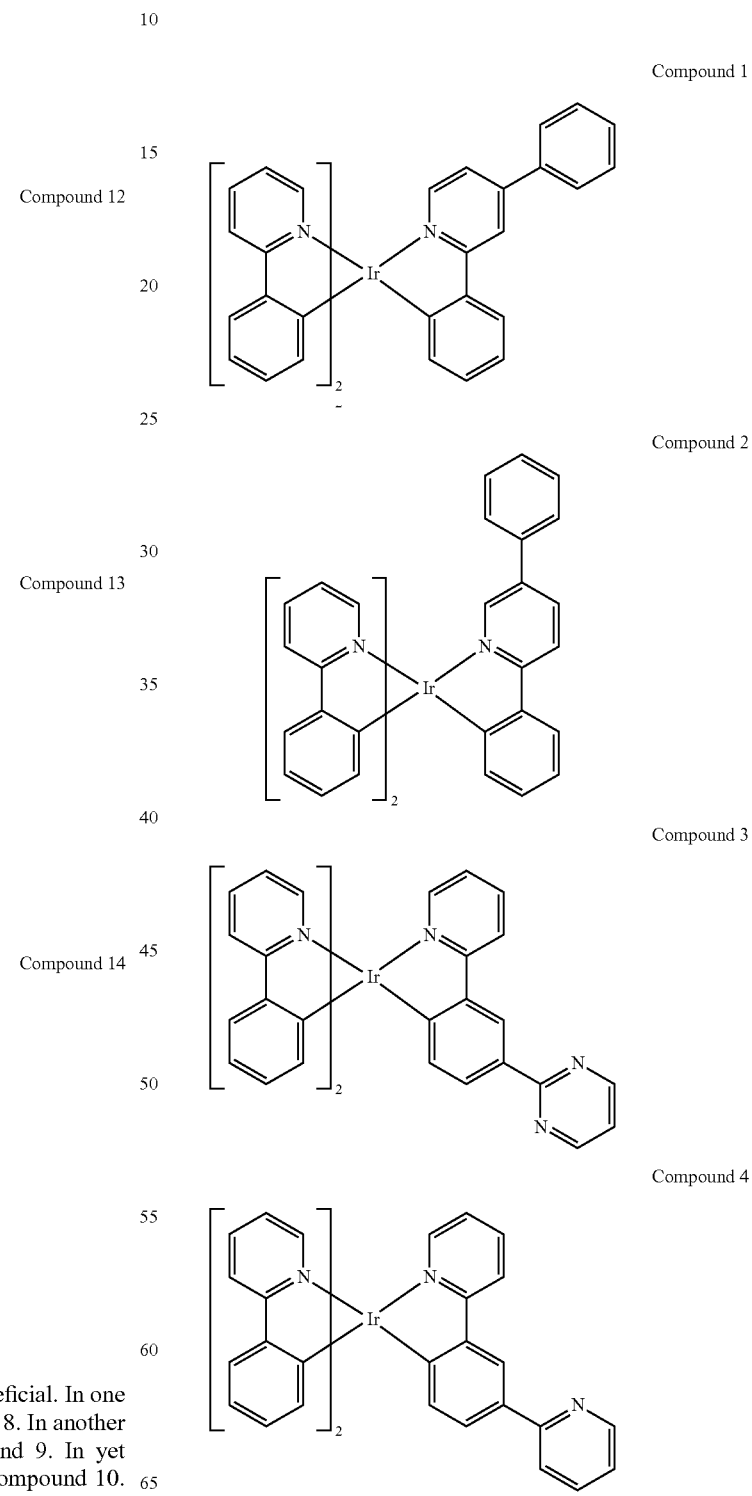

Compound 1

Compound 2

Compound 3

Compound 4

Compound 5

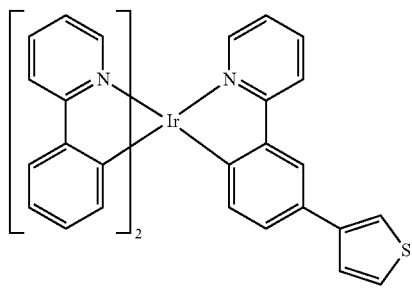

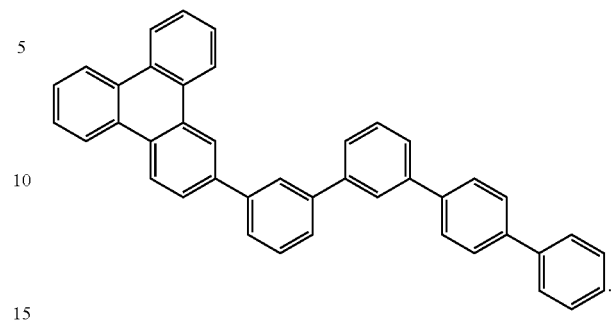
H1

An organic light emitting device is provided, the device comprising an anode, a cathode, and an organic layer disposed between the anode and the cathode. The organic layer further comprises a compound selected from the group consisting of:

Compound 6

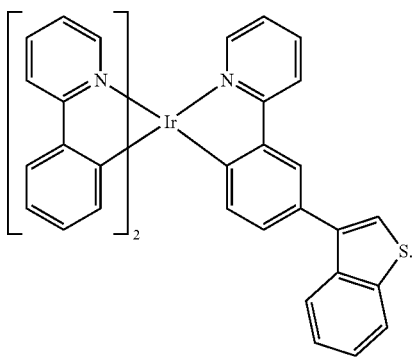

Compound 8

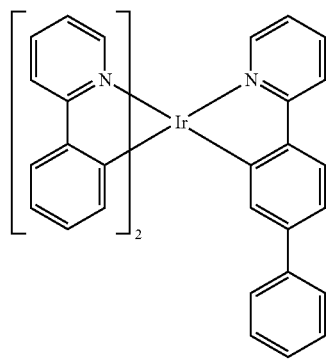

In one aspect, the organic layer of the device further comprises a host. Compounds 1 and 2 have been shown to work particularly well in devices having a host that contains a triphenylene group. In particular, these compounds are advantageously used in devices wherein the host has the formula Compound 9

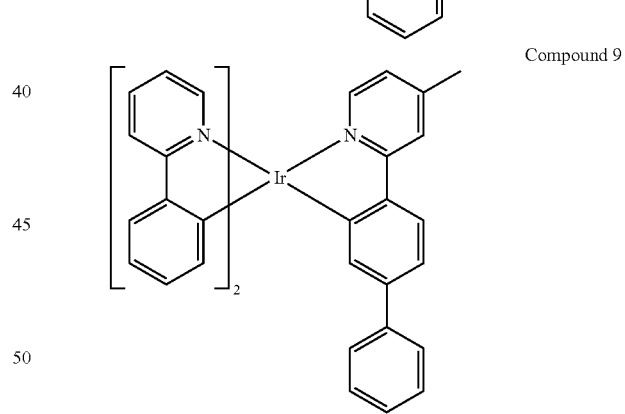

Compound 10

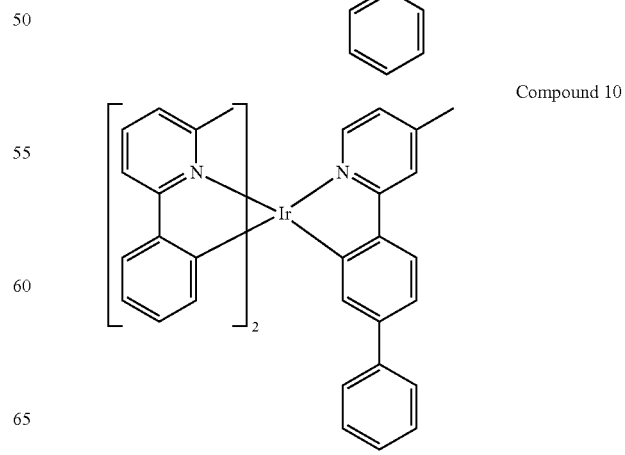

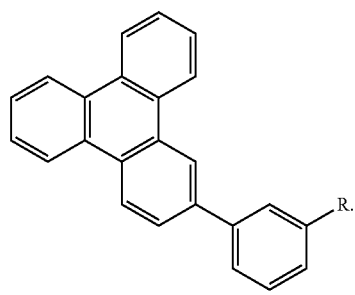

R is aryl or heteroaryl. In a certain aspect, the host compound has the formula where R is terphenyl. Moreover, the inventive compounds may be especially useful in a device wherein the host has the structure Compound 11

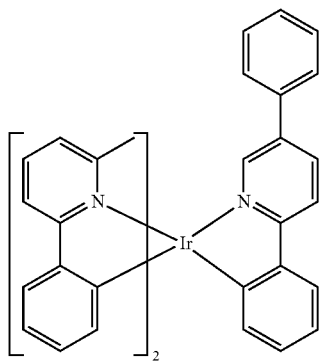

Compound 12

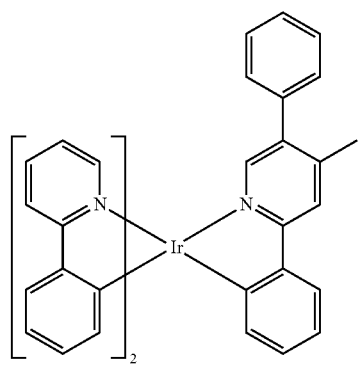

Compound 13

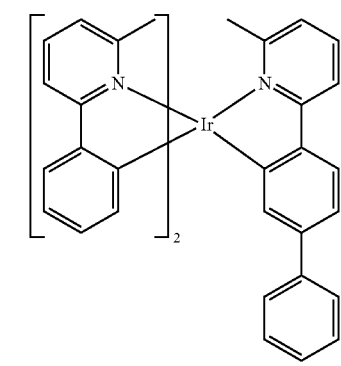

Compound 14

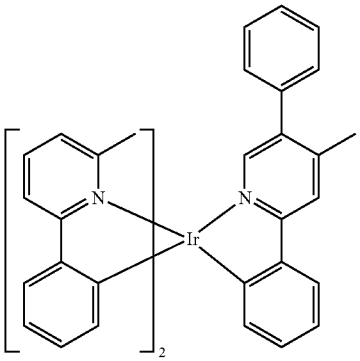

The organic layer of the device may further comprise a host. Compounds 7-12 have been shown to work particularly well in devices having a host that contains a triphenylene group. In particular, the compounds may be used in a device wherein the host has the formula

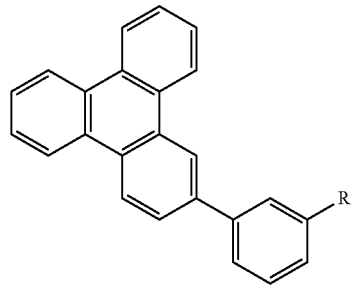

where R is aryl or heteroaryl. In one aspect, the host compound has the formula described above where R is terphenyl. Preferably, the compounds may be used in a device wherein the host has the structure

H1

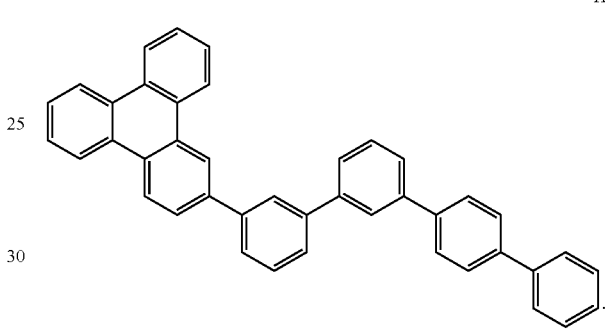

In another aspect, the compounds may be used in a device wherein the host has the formula described above where R is dibenzothiophene. Preferably, the compounds may be used in a device wherein the host has the structure

H2

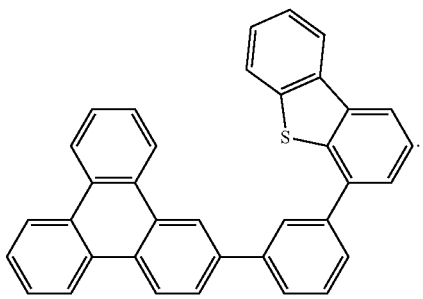

Additionally, a consumer product comprising the device is also provided. The device further comprises an anode, a cathode, and an organic layer disposed between the anode and the cathode. The organic layer contains a compound selected from Compounds 1-6.

A consumer product comprising a device is also provided, wherein the device further comprises an anode, a cathode and an organic layer which is disposed between the anode and the cathode. The organic layer further comprises a compound selected from the group consisting of Compounds 8-14.

As discussed previously, the existing synthetic methods for making heteroleptic iridium complexes may not be practical for the production of many compounds. One commonly used synthetic route involves reacting an iridium triflate intermediate with a second ligand in an organic solvent to produce heteroleptic iridium complexes.

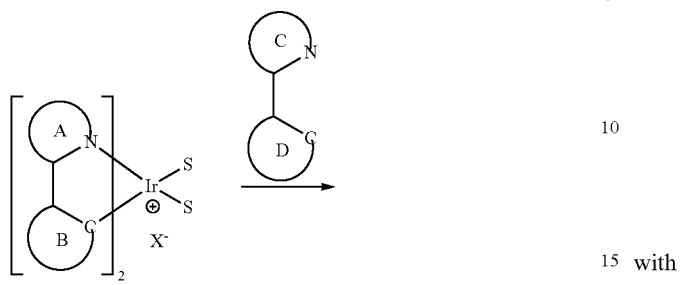

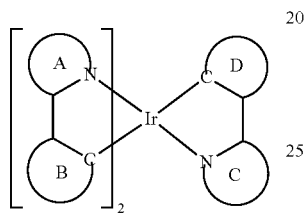

Major product

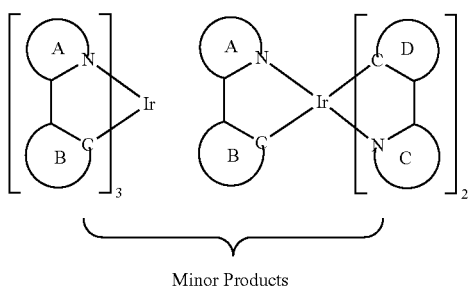

Minor Products

However, this method often produces a mixture of products because of the ligand scrambling during the reaction. Specifically, this method generates both major and minor products in varying yields. The mixture of product compounds can cause problems in purifying the desired product and therefore may limit the practicality of the synthesis.

Of note, several of the heteroleptic iridium compounds provided herein (i.e., Compounds 10, 11 and 14) were generated in high yield and without a significant amount of contaminating minor products using a triflate intermediate synthesis when an alkyl-substituted triflate intermediate (e.g., 6'-methylphenylpyridine) was used. The very low degree of ligand scrambling in the synthesis of Compounds 10, 11 and 14 was unexpected at least in part because the same synthesis failed to provide the same results when used to make other compounds structurally similar to Compound 11 (e.g., Compound 2). See Example 8 and Experimental Section.

Figure 6:
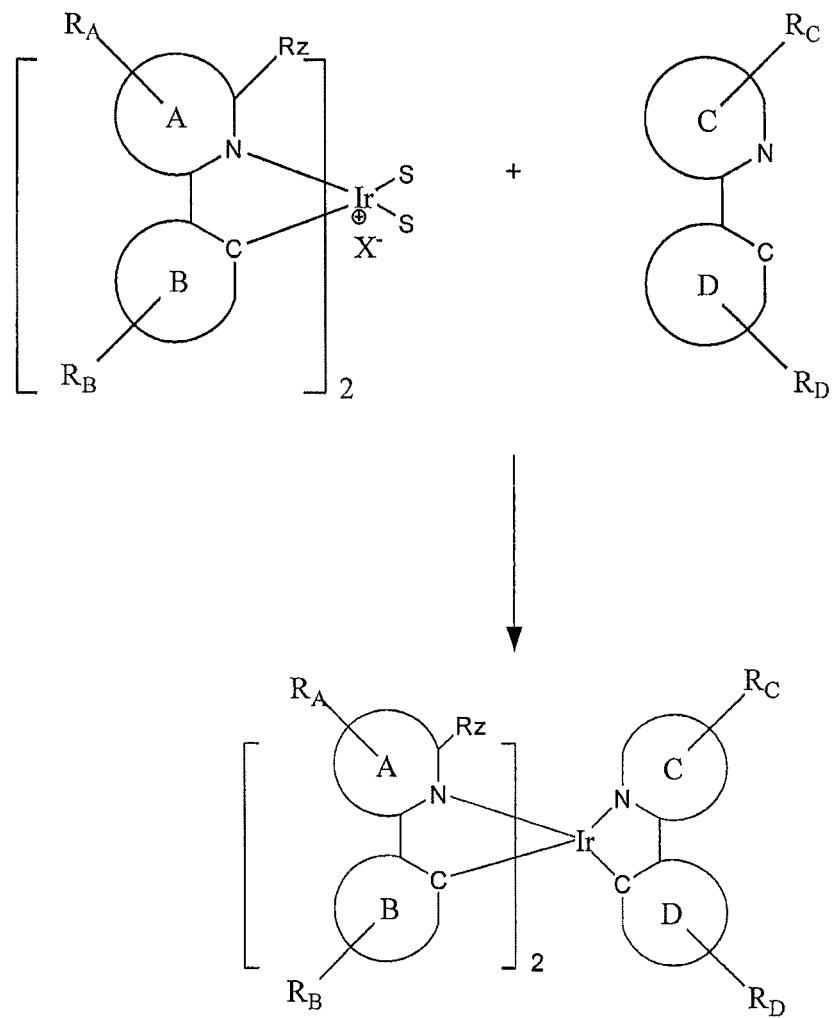
FIG. 6 shows a method for making heteroleptic Ir (III) compounds.

Accordingly, a method for making heteroleptic compounds having extended conjugation is provided herein (illustrated in FIG. 6). The method comprises reacting with to form S is a neutral ligand. X is a counterion. A and B are each independently a 5 or 6-membered aromatic or heteroaromatic ring, and A-B represents a bonded pair of aromatic or heteroaromatic rings coordinated to the iridium via a nitrogen atom on ring A and an $sp^2$ hybridized carbon atom on ring B. C and D are each independently a 5 or 6-membered aromatic or heteroaromatic ring, and C-D represents a bonded pair of aromatic or heteroaromatic rings coordinated to the iridium via a nitrogen ring atom on ring C and an $sp^2$ hybridized carbon atom on ring D. $R_A$, $R_B$, $R_C$, and $R_D$ are each independently selected from the group consisting of no substitution, alkyl, heteroalkyl, aryl, or heteroaryl groups, and each of $R_A$, $R_B$, $R_C$, and $R_D$ represent one or more substituents. $R_Z$ is not H.

Preferably, the counterion X is selected from the group consisting of triflate, tosylate, trifluoroborate, and hexafluorophosphate.

$R_A$, $R_B$, $R_C$, and $R_D$ are preferably selected from the group consisting of benzene, pyrimidine, pyridine, thiophene, thianaphthene, fluorine, carbazole, and dibenzothiophene. Additionally, $R_Z$ is preferably an alkyl and more preferably $R_Z$ is methyl.

In one aspect, the method includes reacting

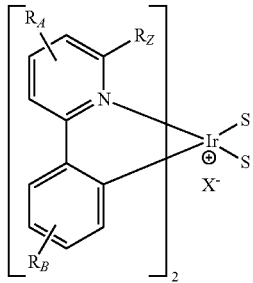

with

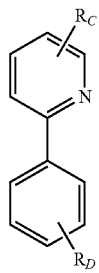

to form

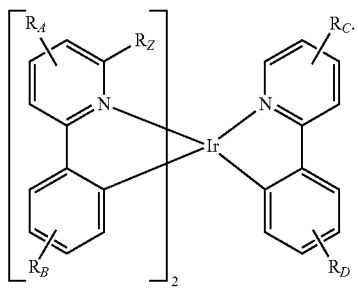

Preferably,

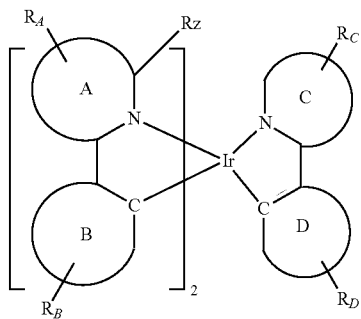

is selected from the group consisting of

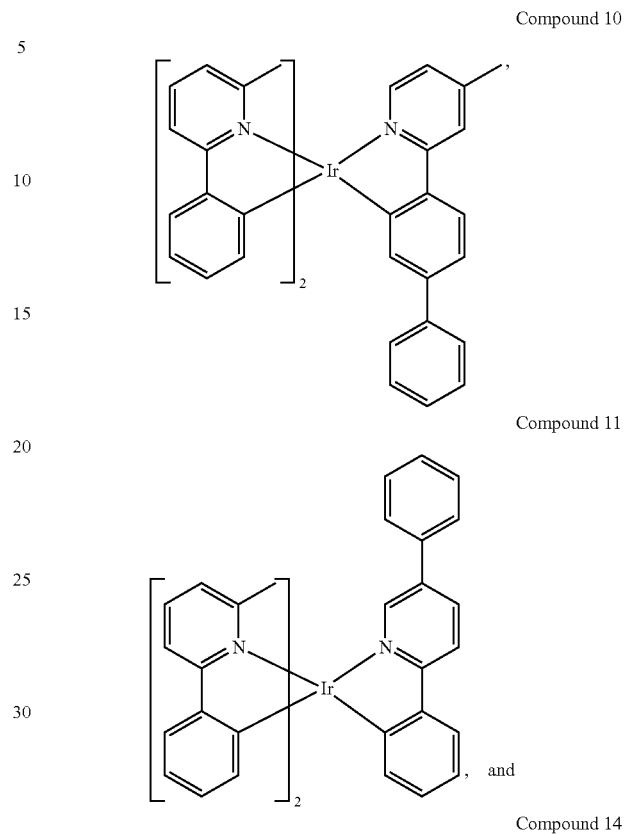

The method comprises an alkyl substituted-phenylpyridine (e.g., 6-methylphenylpyridine), instead of phenylpyridine, as the A-B ligand which when reacted with the C-D ligand may result in no significant scrambling of the reaction products thereby providing an easier to purify product. In particular, the method described above was used to synthesize Compounds 10, 11 and 14 and demonstrated high yield of the desired product with very low contamination with scrambled product. After the reaction was complete, the reaction product was analyzed chromatographically. Specifically, HPLC percentages of the major product for Compounds 10, 11, and 14 were calculated as 99.4%, 99.4 and 99.4%, respectively, whereas the minor products have combined HPLC percentages of 0.3%, 0.5%, and 0.5%, respectively, in the unpurified precipitated product. On the other hand, if the existing triflate intermediate method was used to make heteroleptic compounds, i.e., the 6-position of $L_{A-B}$ is not substituted, significant scrambling of the product can occur. In particular, synthesis of Compounds 2 and 7 using the existing method provided 92% and 91% respectively of the major product, and 8% and 9% respectively of the minor products in the unpurified reaction mixture (as determined by HPLC). Thus, the method using alkyl substituted-phenylpyridine ligands described above provide an improved synthesis for heteroleptic compounds.

Additionally, heteroleptic compounds having the formula $Ir(L_{A-B})_2(L_{C-D})$ are provided. $L_{A-B}$ is

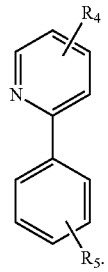

$L_{C-D}$ is selected from the group consisting of:

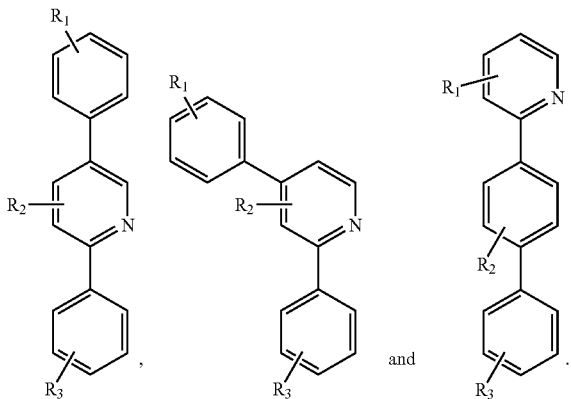

$R_1$, $R_2$, $R_3$, $R_4$ and $R_5$ are each independently selected from the group consisting of hydrogen and alkyl, and each of $R_1$, $R_2$, $R_3$, $R_4$ and $R_5$ may represent mono, di, tri, tetra, or penta substitutions. Preferably, $R_1$, $R_2$, $R_3$, $R_4$ and $R_5$ are each independently selected from hydrogen and methyl.

The ligand $L_{C-D}$ is preferably selected from the group consisting of:

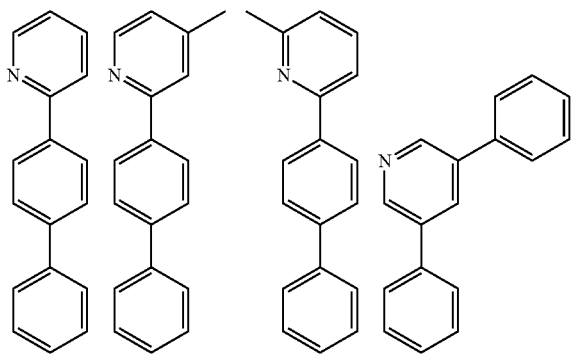

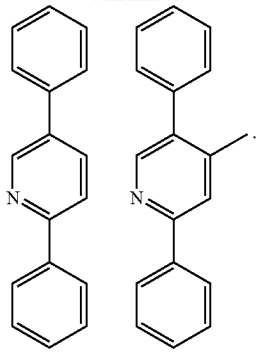

-continued

2-Phenylpyridine and alkyl substituted 2-phenylpyridine ligands may provide beneficial properties. In particular, these ligands bind strongly with iridium (III). Thus, 2-phenylpyridine and alkyl substituted 2-phenylpyridine provide good chemical stability. Additionally, the tris complexes of iridium and 2-phenylpyridine ligands evaporate under high vacuum at low temperatures (i.e., <250° C.). However, the operational stability of PHOLEDs using these complexes as emitters is poor and thus needs to be improved. Aryl substitution on 2-phenylpyridine can improve device stability. Unfortunately, the tris iridium complexes of aryl substituted 2-phenylpyridine can only be evaporated at high temperatures (i.e., >290° C.). High evaporation temperature is not desirable for long term manufacturing due to decomposition. Therefore, the use of such tris aryl substituted 2-phenylpyridine in PHOLEDs may be limited. The heteroleptic compounds provided herein comprise two non-substituted 2-phenylpyridine ligands or alkyl substituted 2-phenylpyridine ligands, and one aryl substituted 2-phenylpyridine ligand. Thus, the heteroleptic compounds provided herein may provide lower evaporation temperature and improve device operational lifetime.

In particular, compound 7, which has two 2-phenylpyridine ligands and one 2-(biphenyl-3-yl)pyridine ligand, demonstrated improved stability in a PHOLED compared with tris(2-phenylpyridine)iridium(III). The emission spectrum of compound 7 was slightly red shifted. However, the emission was blue shifted in comparison to tris(2-(biphenyl-3-yl)pyridine)iridium(III). Taken together, this suggests that both ligands, i.e., 2-phenylpyridine and 2-(biphenyl-3-yl) pyridine, probably contributed to the emission. In addition, the oxidation and reduction properties of compound 7, tris(2-phenylpyridine)iridium(III), and tris(2-(biphenyl-3-yl)pyridine)iridium(III) were measured by cyclic voltammetry and there was no significant difference between the values for the three different compounds. Therefore, the substitution pattern of the compound may not significantly shift the HOMO and LUMO levels of the complexes.

For the heteroleptic compounds $Ir(L_{A-B})_2(L_{C-D})$ provided herein, the combination of the ligand $L_{C-D}$ with the ligand $L_{A-B}$ provided better conjugation to the pyridine ring, where the LUMO locates. Without being bound by theory, it is thought that the LUMO of the provided heteroleptic compounds was reduced significantly as a result of the conjugation and stabilized the pyridine ring. At the same time, the emission spectrum became almost identical to $Ir(L_{C-D})_3$, i.e., tris(2-phenylpyridine)iridium (III) with aryl on the pyridine, suggesting that the emission is dominated by $L_{C-D}$ while $L_{A-B}$ is a non-emitting ligand. The heteroleptic compounds $Ir(L_{A-B})_2(L_{C-D})$ disclosed herein provide high device stability. For the heteroleptic compounds Ir(L$_{A-B}$)(L$_{C-D}$)$_2$ provided herein, the effect is similar.

Figure 4:
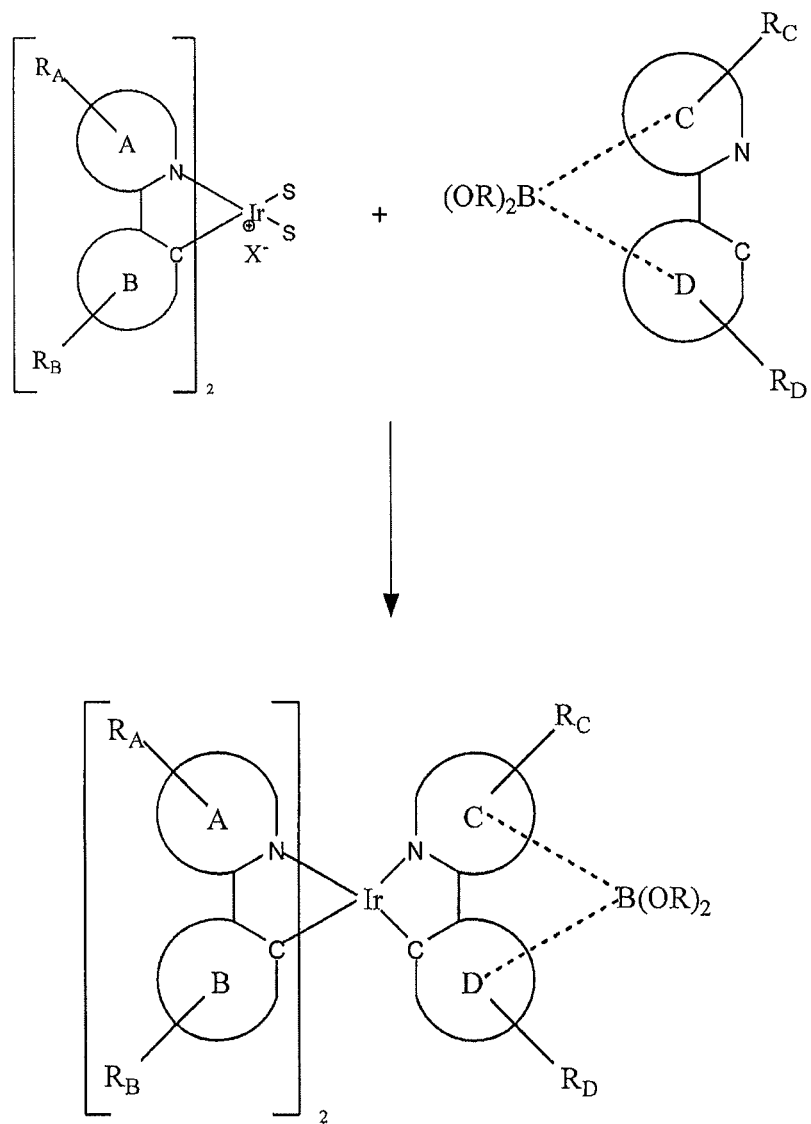
FIG. 4 shows a method of making heteroleptic Ir (III) compounds.
Figure 5:
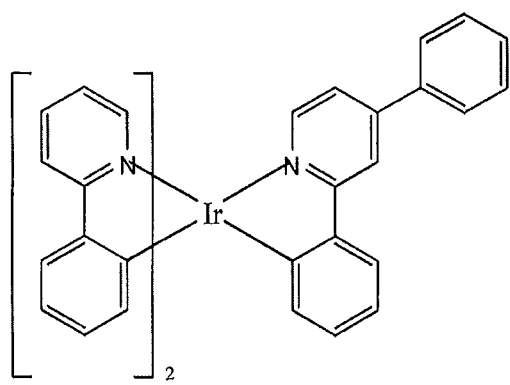
FIG. 5 shows heteroleptic Ir (III) complexes having extended conjugation.
Figure 5:
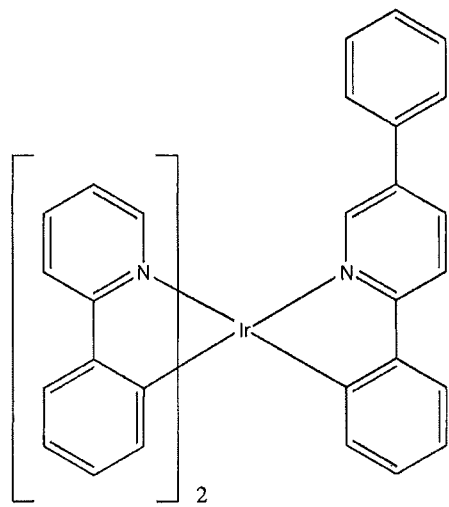

As discussed in previous paragraphs, the synthesis of heteroleptic Ir (III) complexes may be improved by a method wherein a boronic ester functionalized ester is reacted directly with an iridium complex intermediate. The method is also shown in FIG. 4. In particular, the synthesis may be more practical for large scale synthesis of the complexes. The products of the reaction can be separated by column or other methods. In addition, heteroleptic Ir (III) complexes having extended conjugation from the heterocyclic ring may be made according to the method described herein. These compounds are also shown in FIG. 5. The use of these complexes in devices may result in improved device stability and manufacturing.

As discussed above, the synthesis of heteroleptic Ir (III) compounds may be improved by a method wherein a substituted triflate iridium intermediate is reacted with a second ligand. The method is also shown in FIG. 6. In particular, the synthesis may provide improved product purification due to significantly reduced ligand scrambling.

Figure 7:
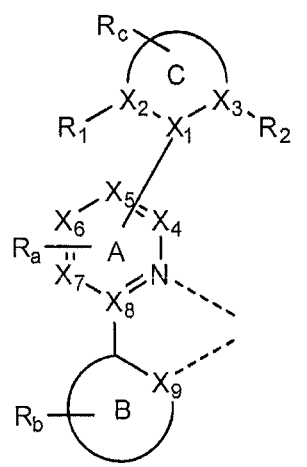
FIG. 7 shows a ligand containing a twisted aryl and a compound comprising a ligand containing a twisted aryl.
Figure 7:
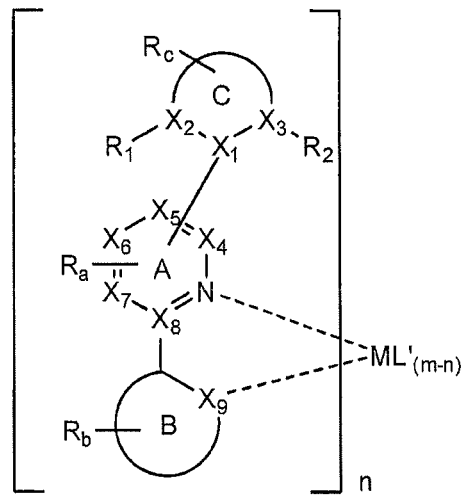
Figure 8:
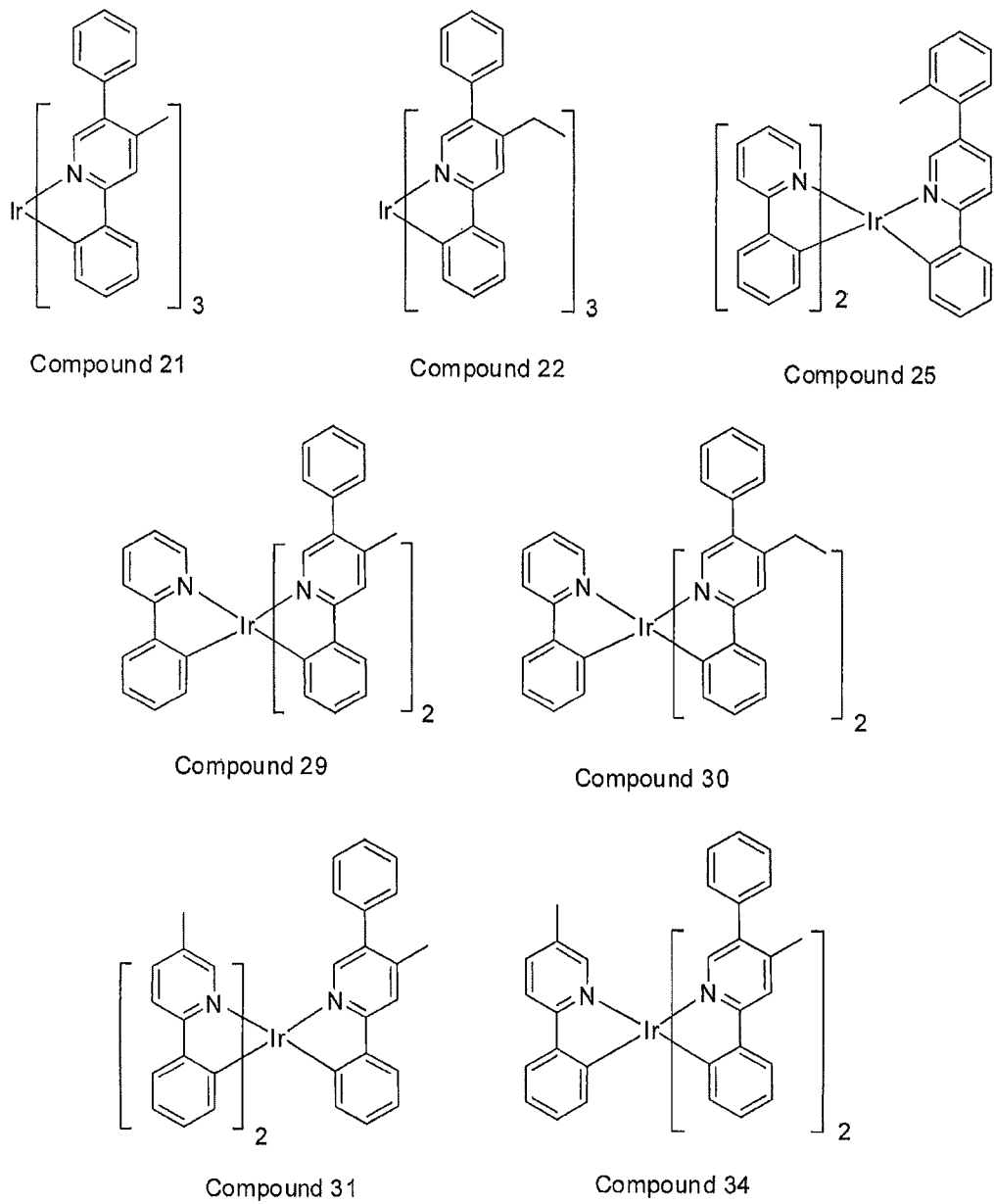
FIG. 8 shows exemplary compounds.

Novel compounds are provided, the compounds comprise at least one ligand containing a twisted aryl (illustrated in FIG. 7). Specific compounds provided include Ir(2-phenylpyridine) type compounds containing a twisted phenyl ring (illustrated in FIG. 8). These twisted aryl compounds may be advantageously used in OLEDs to provide devices having improved efficiency, stability and manufacturing. Preferably, these compounds may be used as an emitting dopant in such devices.

Compounds containing a twisted aryl group have been reported in the literature (see, e.g., US2007/0003789 and US2009/0124805).

While 2-phenylpyridine and alkyl substituted 2-phenylpyridine ligands form iridium(III) compounds with good properties, these compounds may have limited practical use in devices (e.g., poor operational stability). Aryl substitution on 2-phenylpyridine can improve device efficiency, but tris iridium compounds of aryl substituted 2-phenylpyridine can only be evaporated at high temperatures (i.e., above 290° C.) thereby limiting the use of these compounds as well (i.e., decomposition in manufacturing). It was found that 2-phenylpyridine type ligands having particular substitution patterns may be particularly beneficial. In particular, the strategic combination of alkyl and phenyl substitutions on the 2-phenylpyridine type ligand may result in the substituent aryl group twisting out of plane (i.e., twisted aryl) thereby reducing packing and lowering the evaporation temperature. The compounds provided herein comprise at least one ligand with an alkyl and aryl substituent such that the substituent aryl is a twisted aryl. Thus, these compounds may provide lower evaporation temperature, improve device manufacturing and improve device operational lifetime.

Aryl groups substituted on 2-phenylpyridine may also increase the conjugation of the ligand thereby resulting in a red shifted emission. Such compounds having emission at longer wavelengths in the yellow part of the spectrum, such as 540 nm to 580 nm, may have limited use because there emission is limited to the yellow part of the spectrum. Therefore, compounds having emission at a different range, such as a blue shifted range, may be desirable. In particular, compounds with an emission in the target energy range of about 521 nm to about 540 nm may be particularly desirable. It is believed that compounds in which the substituent aryl ring is twisted by the addition of an alkyl group may have limited conjugation and demonstrate a blue shifted emission. In particular, the twisted aryl compounds provided herein may have emission energies that are blue shifted relative to the corresponding compounds containing untwisted aryl substituents. Therefore, these blue shifted compounds may be particularly preferable.

Compounds containing at least one ligand with a twisted aryl are provided. The effect of different twisted aryl substitution patterns on the emissive ligand was studied to establish a structure-property relationship for substituted Ir(2-phenylpyridine) type phosphorescent materials and devices containing such materials. Several aspects of material processability, including evaporation temperature, evaporation stability, and solubility, as well as device characteristics of PHOLEDs using twisted phenyl containing compounds were studied. Strategically positioned substituents present on the compound may lead to the twisting of the substituent aryl ring. For example, substituents present on the aryl group (i.e., ring C) or on the pyridine ring adjacent to the twisted aryl (i.e., ring A) may induce the extra twisting of the aryl group. As a result, the compounds having a twisted aryl moiety may provide (i) reduced conjugation thereby minimizing the red-shifting effect that is usually associated with increased conjugation (i.e., the additional of a phenyl), (ii) reduced stacking thereby lowering evaporation temperatures and increasing long-term thermal stability and processability, and (iii) narrow emission thus resulting in high luminous efficiency (i.e., high LE:EQE).

Compounds containing a twisted aryl and a limited number of substituents (e.g., a single substituent) may provide improved stability while maintaining the benefits of the twisted aryl, such as improved efficiency and manufacturing. Further, certain compounds provided herein may demonstrate particularly narrow emission thus providing devices having especially good luminous efficiency in addition to the other noted improvements. Therefore, the compounds provided herein may be particularly desirable.

Without being bound by theory, it is believed that compounds having only one substituent inducing the twist in the substituent aryl may be especially beneficial. In particular, compounds with a single substituent inducing the twist of the aryl substituent may be more stable than corresponding compounds containing multiple substituents. It is thought that compounds having a single substituent may have a smaller degree of twisting between the substituent aryl and the remainder of the ligand, and thus more conjugation, as compared to compounds with multiple substituents which may have a higher degree of twisting out of plane. Specifically, it is thought that compounds with a single methyl substituent may have improved stability compared to compounds having multiple methyl substituents. For example, Device Example 28 and Comparative Device Example 6 have the same device structure and composition except that Device Example 28 uses Compound 35 as the emitting dopant whereas Comparative Device Example 6 uses E4 as the emitting dopant. Compound 35 and E4 are both tris homoleptic compounds (i.e., IrL$_3$) with a ligand which has a twisted aryl group attached to 5 position of 2-phenylpyridine. Their only difference is that in Compound 35, the aryl is a 2-methylphenyl group whereas in E4, the aryl is a 2,6-dimethylphenyl.

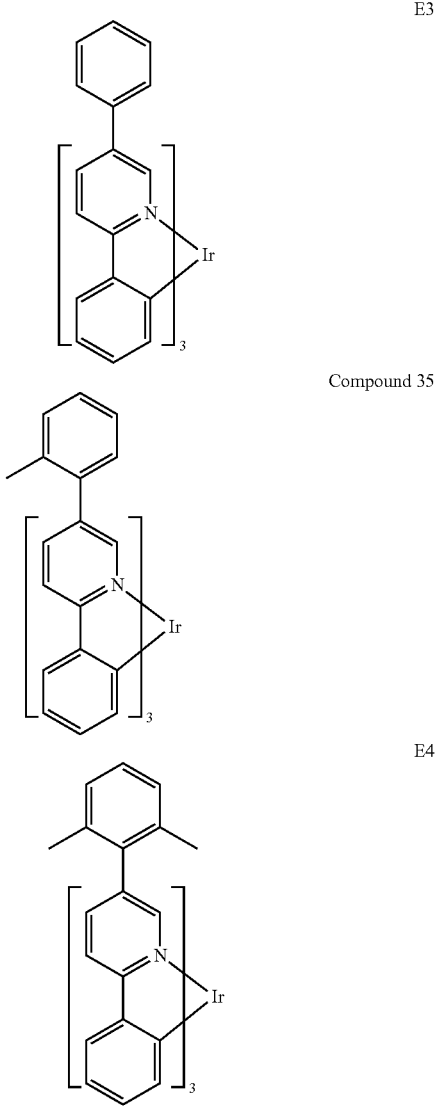

E3

Compound 35

E4

The extra methyl group in E4 makes the twisted aryl twist more than that in Compound 35. The result (Table 8) shows that the device with Compound 35 (Device Example 28, $RT_{80}\%=200$ h) is much more stable than the device with E4 (Comparative Device Example 6, $RT_{80}\%=42$ h). It is believed that a more conjugated ligand can lead to more stable emitting dopant. The conjugation in the series of E3, Compound 35 and E4 decreases as the number of methyl group increases from zero to one to two (i.e., increasing twist between pyridine and the C-ring). It is therefore reasonable to believe a device with E3 as the emitting dopant would be even more stable than a device with Compound 35 as the emitting dopant. However, the increase in conjugation also causes red shift in the emission of the corresponding Ir complexes. Table 7 shows that E3 (Comparative Device Example 5) has a $\lambda_{max}$ of 548 nm and CIE of (0.430, 0.560), whereas Compound 35 (Device Example 28) has a $\lambda_{max}$ of 532 nm and CIE of (0.368, 0.607) and E4 (Comparative Device Example 6) has a $\lambda_{max}$ of 520 nm and CIE of (0.320, 0.632). Therefore, although E3 may be more stable, but the emission is yellow which is not suitable for full color RGB display. Compound 35 has conjugation between E3 and E4, achieving much improved stability over E4 (little conjugation) and better green color over E3 (too much conjugation).

Compounds are provided, comprising a ligand L having an alkyl substituent and an aryl substituent such that the substituent aryl is twisted and having the structure:

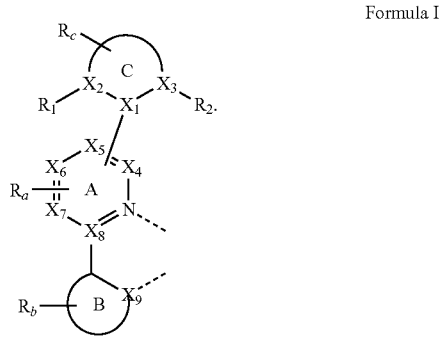

Formula I

B and C are each independently a 5 or 6-membered carbocyclic or heterocyclic ring. A-B represents a bonded pair of carbocyclic or heterocyclic rings coordinated to a metal M via a nitrogen atom in ring A and an $sp^2$ hybridized carbon atom in ring B. A-C represents a bonded pair of carbocyclic and heterocyclic rings. $R_a$, $R_b$, and $R_c$ may represent mono, di, tri, or tetra substitutions. $R_a$, $R_b$, and $R_c$ are independently selected from the group consisting of hydrogen, alkyl, alkoxy, amino, alkenyl, alkynyl, arylkyl, aryl, and heteroaryl. $X_1$, $X_2$, $X_3$, $X_4$, $X_5$, $X_6$, $X_7$, $X_8$, and $X_9$ are independently selected from carbon and nitrogen. Preferably, A is pyridine. $R_1$ and $R_2$ are independently selected from the group consisting of hydrogen, alkyl, alkoxy, amino, alkenyl, alkynyl, arylkyl, aryl, and heteroaryl. At least one of $R_1$, $R_2$, and the $R_a$ substituents adjacent to C is not hydrogen. Preferably, only one of $R_1$, $R_2$, and the $R_a$ substituents adjacent to C is not hydrogen. Preferably, only one of $R_1$, $R_2$, and the $R_a$ substituents adjacent to C is alkyl. More preferably, only one of $R_1$, $R_2$, and the $R_a$ substituents adjacent to C is ethyl. Most preferably, only one of $R_1$, $R_2$, and the $R_a$ substituents adjacent to C is methyl. The ligand L is coordinated to the metal M having an atomic number greater than 40. Preferably, the metal M is Ir.

Particular compounds are provided having the structure:

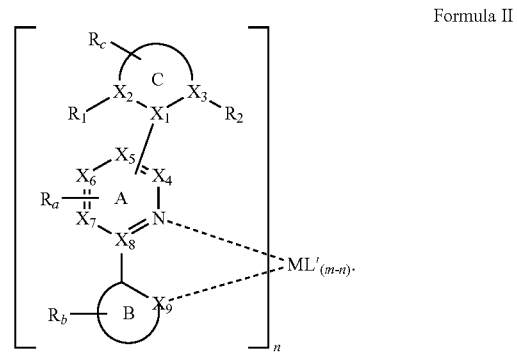

Formula II m is the oxidation state of the metal M. n is at least 1. L' is a monoanionic bidentate ligand. Preferably, only one of $R_1$, $R_2$, and the $R_a$ substituents adjacent to C is not hydrogen. Preferably, only one of $R_1$, $R_2$, and the $R_a$ substituents adjacent to C is alkyl. More preferably, only one of $R_1$, $R_2$, and the $R_a$ substituents adjacent to C is ethyl. Most preferably, only one of $R_1$, $R_2$, and the $R_a$ substituents adjacent to C is methyl. Preferably, A is pyridine.

Particular examples of compounds having Formula II are provided. The compound is selected from the group consisting of:

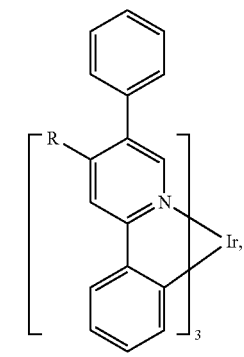

Compound 15

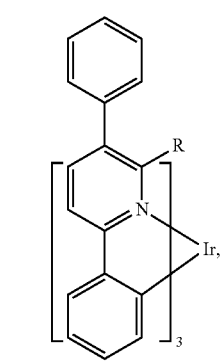

Compound 16

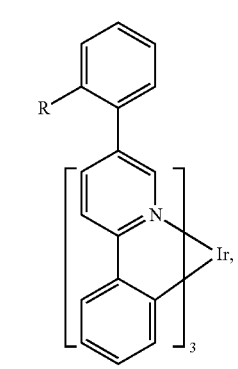

Compound 17

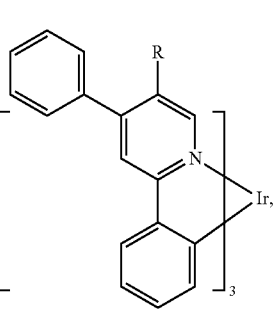

Compound 18

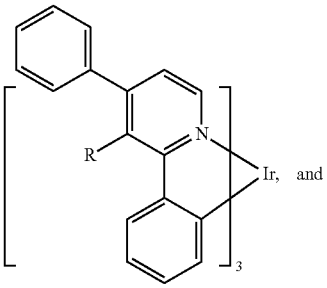

Compound 19

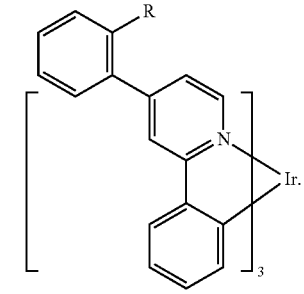

Compound 20

R is not hydrogen. Preferably, R is alkyl.

Specific examples of compounds having Formula II are provided. In one aspect, the compound is selected from the group consisting of:

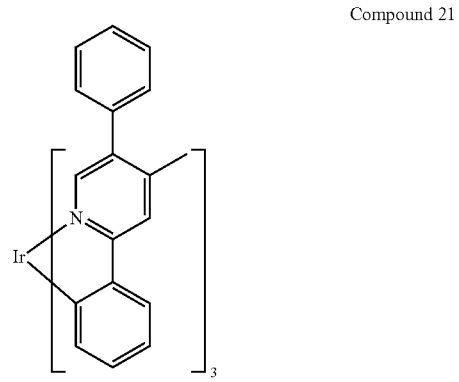

Compound 21

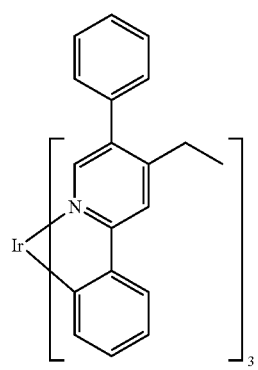

Compound 22

Compound 23
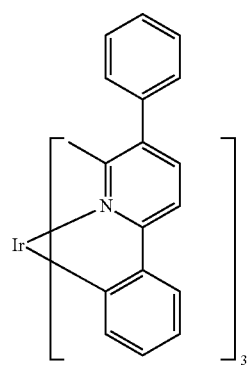
Compound 24
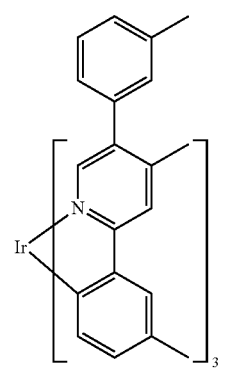
Compound 25
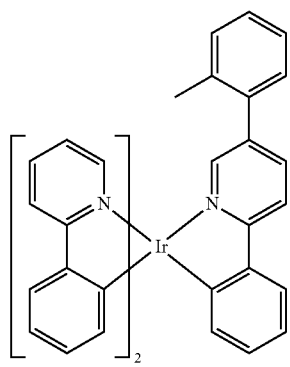
Compound 26
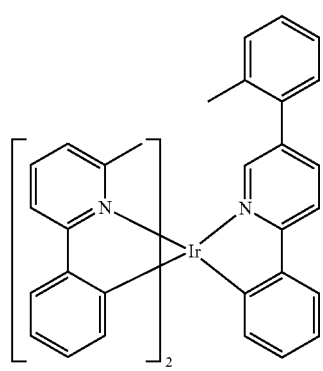
Compound 27
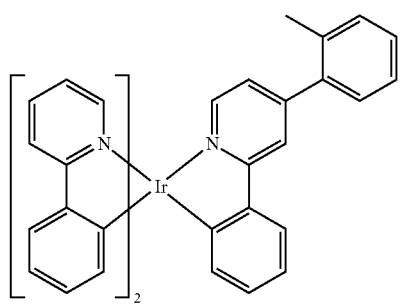
Compound 28
Compound 29
Compound 30
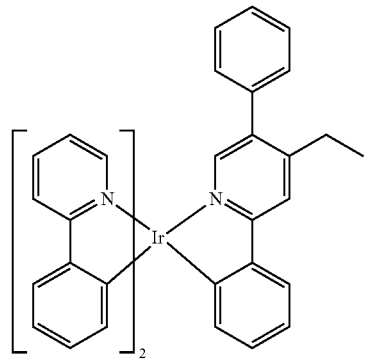

Compound 31
Compound 32
Compound 33
Compound 34
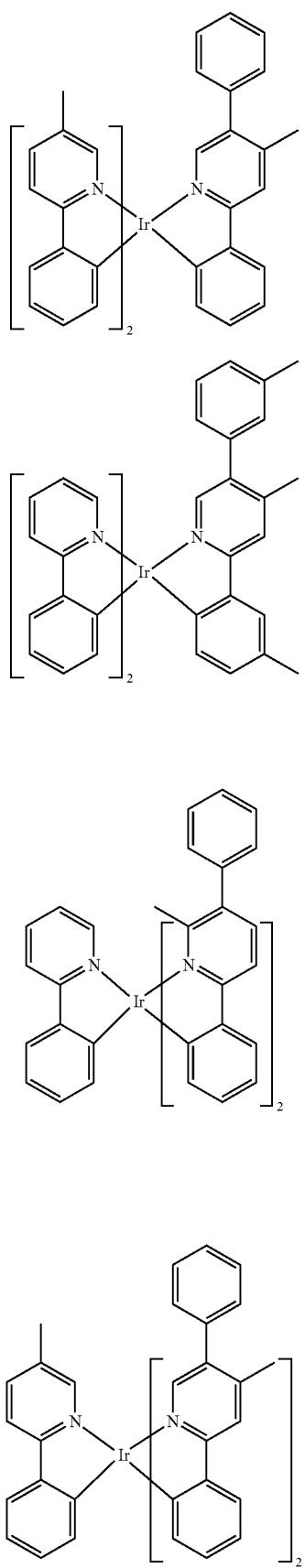
Compound 35
Compound 36
Compound 37
Preferably, the compound is selected from the group consisting of Compound 21, Compound 22, Compound 25, Compound 29, Compound 30, Compound 31 and Compound 34.
In one aspect, compounds are provided wherein the compound is selected from the group consisting of:

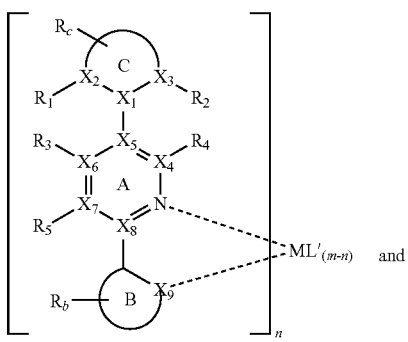

Formula III

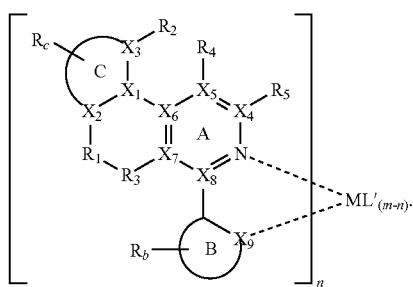

Formula IV

At least one of $R_1$, $R_2$, $R_3$, and $R_4$ are not hydrogen. $R_5$ is selected from the group consisting of hydrogen, alkyl, alkoxy, amino, alkenyl, alkynyl, arylkyl, aryl, and heteroaryl.

As discussed above, the position of the twist inducing substituent adjacent to the substituent aryl ring (i.e., C ring) results in the twisting of the C ring out of plane thereby reducing packing and offering a wide range of tunability in terms of evaporation temperature, solubility, energy levels, device efficiency and narrowness of the emission spectrum. In addition, the substituents can be stable functional groups chemically as well as in device operation.

In one aspect, $R_1$ and $R_2$ are hydrogen and one of $R_3$ and $R_4$ is alkyl. Exemplary compounds may include Compounds 21-24 and 29-34, 36 and 37. In another aspect, one of $R_1$ and $R_2$ is alkyl and $R_3$ and $R_4$ are hydrogen. Exemplary compounds may include Compounds 25-28 and 35.

In another aspect, the compound is selected from the group consisting of:

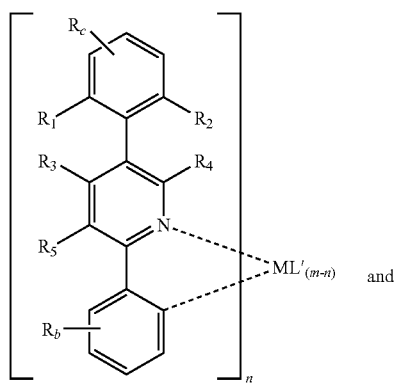

Formula V

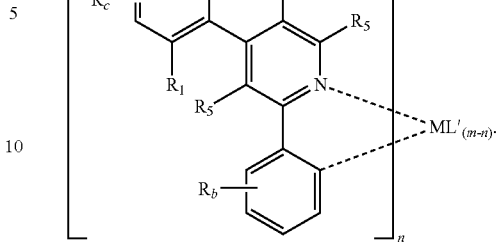

Formula VI

The compounds having Formula II include homoleptic compounds and heteroleptic compounds. Non-limiting examples of homoleptic compound include Compounds 21-24 and 35. Non-limiting examples of heteroleptic compounds include Compounds 25-34, 36 and 37.

Particular heteroleptic compounds are provided where the compound has a ligand L' selected from the group consisting of:

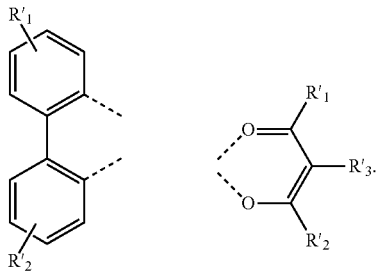

$R'_1$, $R'_2$ and $R'_3$ are independently selected from the group consisting of hydrogen, alkyl, alkoxy, amino, alkenyl, alkynyl, arylkyl, aryl, and heteroaryl.

Twisted aryl containing compounds having an alkyl substituent present on the pyridine ring of the 2-phenylpyridine ligand also having the aryl substituent may be preferred. In particular, preferred compounds are provided wherein the compound selected from the group consisting of Compound 21-Compound 23, Compound 29-Compound 31, Compound 34, Compound 36 and Compound 37. Even more preferred compounds are Compound 21, Compound 22, Compound 29-31, Compound 34, Compound 36 and Compound 37 which has the alkyl group at the 4-position of the 2-phenylpyridine ligand (i.e., para to the pyridine nitrogen). It is because such substitution can provide the twist and also a slight blue shifting effect to make the compound emit in a deeper green emission. For example, Device Example 13 has $\lambda_{max}$ of 525 nm and CIE of (0.342, 0.612) whereas Device Example 19 has $\lambda_{max}$ of 532 nm and CIE of (0.372, 0.599). Example 13 uses Compound 12 as the emitting dopant which has a methyl group at the 4-position of the 2-phenylpyridine ligand whereas Example 19 uses Compound 25 as the emitting dopant which has a methyl group at the 2-position of the twist phenyl. Although the twist induced structurally in both cases is believed to be similar, the methyl para to the pyridine nitrogen provides electron donating effect, raising the LUMO energy level of complex and also the triplet energy, resulting in a blue shift in emission.

An organic light emitting device is also provided. The device has an anode, a cathode, and an organic layer disposed between the anode and the cathode, where the organic layer comprises a compound having Formula I, as described above. Selections for the substituents described as preferred for the compounds having Formula I are also preferred for use in a device that comprises a compound having Formula I. These selections include those described for the metal M; the formulas II-VI; R, $R_1$, $R_2$, and $R_a$ substituents adjacent to C; the position of ring C; and rings A, B, and C.

In one aspect, the device comprises a compound having Formula II, as described above. Preferably, the metal M is Ir. Preferably, A is pyridine. In another aspect, the device comprises a compound having Formula III or Formula IV, as described above. Devices containing a compound wherein only one of $R_1$, $R_2$, and the $R_a$ substituents adjacent to C is alkyl may also be preferred. In another aspect, the device comprises a compound having Formula V or Formula VI, as described above. Certain devices are provided wherein the device contains a compound selected from the group consisting of Compound 21-Compound 37. Preferably, the device contains Compound 21, Compound 22, Compound 25, Compound 29, Compound 30, Compound 31 or Compound 34.

In one aspect, devices are provided wherein the organic layer is an emissive layer and the compound having the formula of Formula I is an emitting dopant. Moreover, the organic layer may further comprise a host. Preferably, the host has the formula:

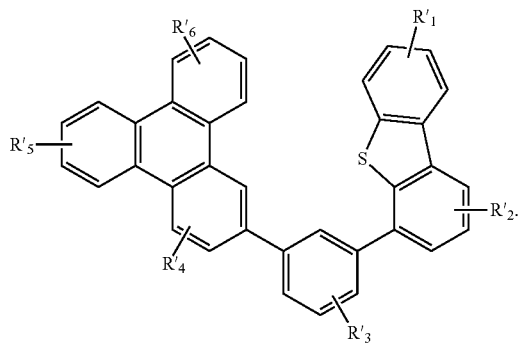

$R'_1$, $R'_2$, $R'_3$, $R'_4$, $R'_5$, and $R'_6$ are independently selected from the group consisting of hydrogen, alkyl, alkoxy, amino, alkenyl, alkynyl, arylkyl, aryl, and heteroaryl.

A consumer product comprising a device is also provided. The device comprises an anode, a cathode, and an organic layer disposed between the anode and the cathode, where the organic layer comprises a compound having Formula I, as described above. Selections for the substituents described as preferred for the compounds having Formula I are also preferred for use in a consumer product containing a device that comprises a compound having Formula I. These selections include those described for the metal M; the formulas II-VI; R, $R_1$, $R_2$, and $R_A$ substituents adjacent to C; the position of ring C; and rings A, B, and C.

Figure 9:
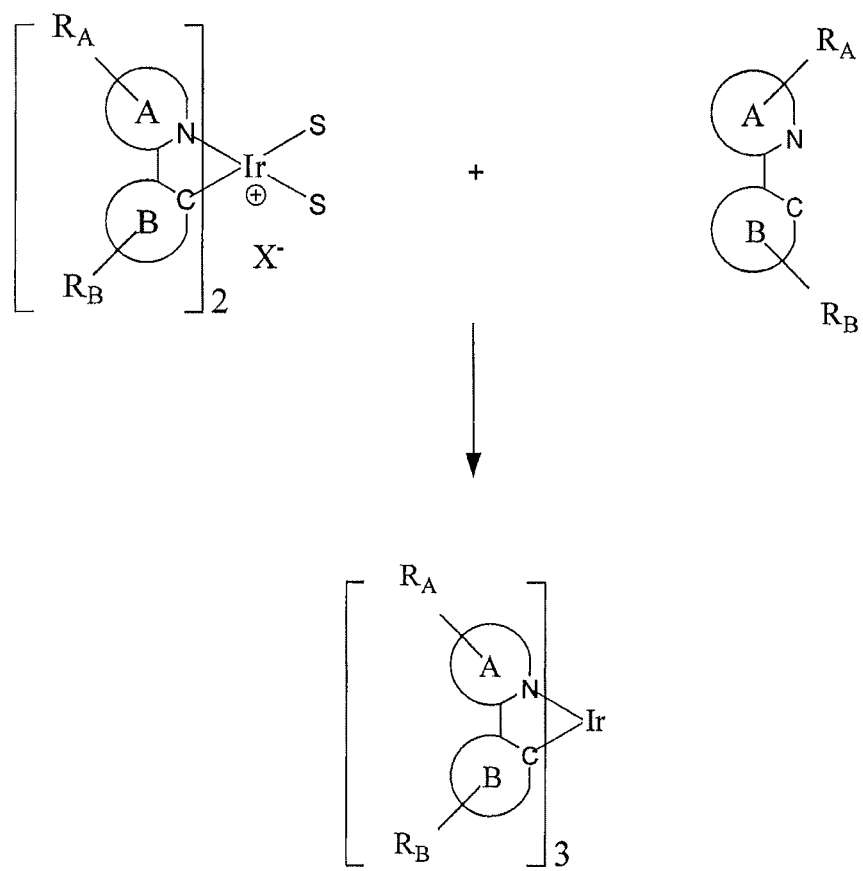
FIG. 9 shows a method for making homoleptic Ir (III) compounds.

Additionally, novel methods are provided for making homoleptic Ir (III) compounds (illustrated in FIG. 9). A commonly used method of making homoleptic Ir (III) compounds involves heating a mixture of Ir(acac)$_3$ with the ligand at refluxing glycerol (~180° C.) or without solvent at >230° C. Such high temperature of reaction can cause problems such as thermal degradation of the ligand and the resulting complex. Therefore, it is highly desirable to provide a new method for making homoleptic Ir (III) compounds at lower temperatures. The methods, as described herein, can be used to make homoleptic Ir (III) compounds that may be advantageously used in OLEDs. In particular, a first method for making a homoleptic Ir (III) compound having is provided. The first method may be used to synthesize compounds having an alkyl group which is not adjacent to the nitrogen in the heteroleptic ring of the ligand. Compounds 21, 22, and 24, for example, may be synthesized using the first method provided. A second method for making homoleptic Ir (III) compounds is also provided. The second method may be used to make compounds having an alkyl group which is adjacent to the nitrogen in the heterocyclic ring of the ligand. Compound 23, for example, may be synthesized using the second method provided.

A first method for making a homoleptic Ir(III) complex is provided. The first method comprising:

reacting

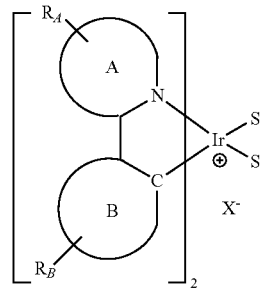

with

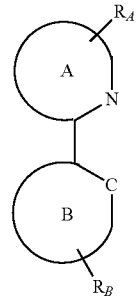

in the presence of a low boiling alcohol to form

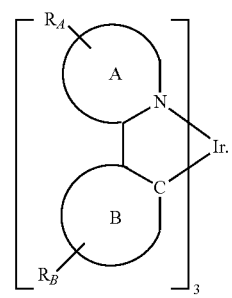

At least one of $R_A$ and $R_B$ is an alkyl group and the alkyl group is not adjacent to the nitrogen on the pyridine ring. S is a neutral ligand. X is a counterion. Preferably, X is triflate. A and B are each independently a 5 or 6-membered carbocyclic or heterocyclic ring. A-B represents a bonded pair of carbocyclic or heterocyclic rings coordinated to the iridium via a nitrogen atom on ring A and an sp² hybridized carbon atom on ring B. Each of $R_A$ and $R_B$ may represent mono, di, tri, or tetra substitutions. $R_A$ and $R_B$ are each independently selected from the group consisting of hydrogen, alkyl, alkoxy, amino, alkenyl, alkynyl, arylkyl, aryl, and heteroaryl.

Low boiling alcohols may include any alcohol which has a boiling temperature equal to or less than 108° C. In one aspect, the low boiling alcohol is selected from the group consisting of methanol, ethanol, n-propanol, isopropanol, n-butanol, a 1:1 ratio of ethanol and methanol, 2-methoxyethanol, and 2-ethoxyethanol. Preferably, the low boiling alcohol is selected from the group consisting of isopropanol which boils at 108° C., ethanol which boils at 78° C., and a 1:1 ratio of ethanol and methanol which boils between 64° C. and 78° C. More preferably, the low boiling alcohol is ethanol or a 1:1 ratio of ethanol and methanol. Most preferably, the low boiling alcohol is a 1:1 ratio of ethanol and methanol.

Preferably, A is:

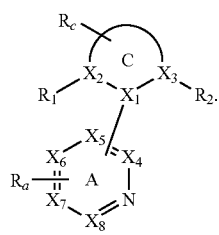

C is a 5 or 6-membered carbocyclic or heterocyclic ring. A-C represents a bonded pair of carbocyclic or heterocyclic rings. $R_A$ and $R_C$ may represent mono, di, tri, or tetra substitutions. $R_A$ and $R_C$ are independently selected from the group consisting of hydrogen, alkyl, alkoxy, amino, alkenyl, alkynyl, arylkyl, aryl, and heteroaryl. $X_1$, $X_2$, $X_3$, $X_4$, $X_5$, $X_6$, $X_7$, $X_8$, and $X_9$ are independently selected from carbon and nitrogen. $R_1$ and $R_2$ are independently selected from the group consisting of hydrogen, alkyl, alkoxy, amino, alkenyl, alkynyl, arylkyl, aryl, and heteroaryl. At least one of $R_1$, $R_2$, and the $R_a$ substituents adjacent to C is not hydrogen.

In one aspect, the first method comprises reacting

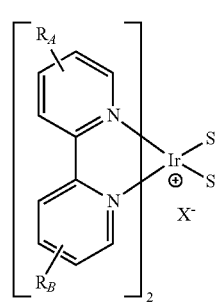

with

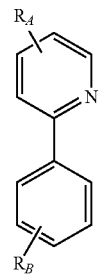

in the presence of a low boiling alcohol to form

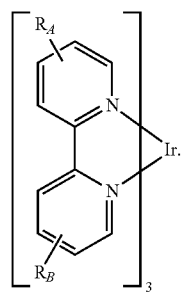

Specific compounds, including Compounds 21, 22, and 24, may be formed using this method.

A second method for making homoleptic Ir (III) compounds is provided. The second method comprises:
reacting

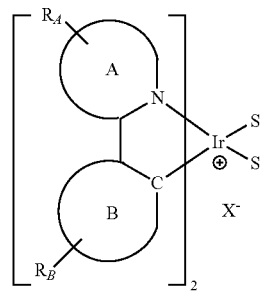

with

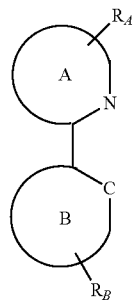

in the absence of solvent to form

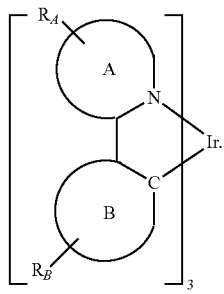

At least one of $R_A$ and $R_B$ is an alkyl group and the alkyl group is adjacent to the nitrogen on the pyridine ring. S is a neutral ligand. X is a counterion. Preferably, X is triflate. A and B are each independently a 5 or 6-membered carbocyclic or heterocyclic ring. A-B represents a bonded pair of carbocyclic or heterocyclic rings coordinated to the iridium via a nitrogen atom on ring A and an sp$^2$ hybridized carbon atom on ring B. Each of $R_A$ and $R_B$ may represent mono, di, tri, or tetra substitutions. $R_A$ and $R_B$ are each independently selected from the group consisting of hydrogen, alkyl, alkoxy, amino, alkenyl, alkynyl, arylkyl, aryl, and heteroaryl.

Preferably, A is:

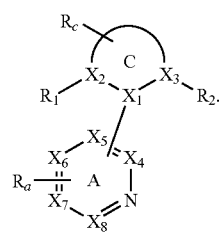

C is a 5 or 6-membered carbocyclic or heterocyclic ring. A-C represents a bonded pair of carbocyclic or heterocyclic rings. $R_A$ and $R_C$ may represent mono, di, tri, or tetra substitutions. $R_A$ and $R_C$ are independently selected from the group consisting of hydrogen, alkyl, alkoxy, amino, alkenyl, alkynyl, arylkyl, aryl, and heteroaryl. $X_1$, $X_2$, $X_3$, $X_4$, $X_5$, $X_6$, $X_7$, $X_8$, and $X_9$ are independently selected from carbon and nitrogen. $R_1$ and $R_2$ are independently selected from the group consisting of hydrogen, alkyl, alkoxy, amino, alkenyl, alkynyl, arylkyl, aryl, and heteroaryl. At least one of $R_1$, $R_2$, and the $R_a$ substituents adjacent to C is not hydrogen.

In one aspect, the second method comprises:
reacting

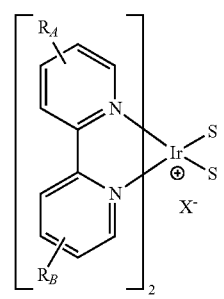

with

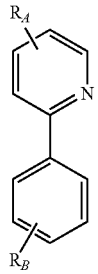

in the absence of solvent to form

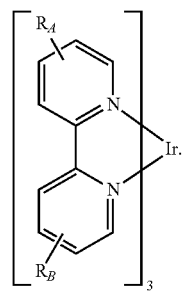

Specific compounds, including Compound 23, may be formed using this method. In particular, Compound 23 can be made using the synthetic method, as follows:

reacting

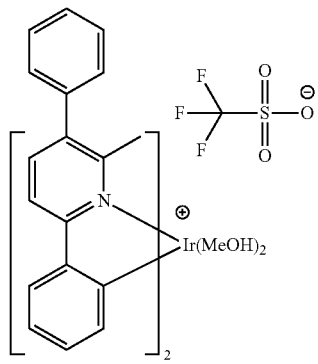

with

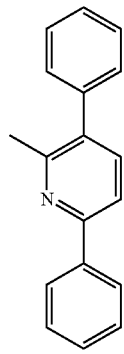 [SMILES: Cc1nc(-c2ccccc2)ccc1-c1ccccc1]

in the absence solvent for 16 h at 130° C. to form

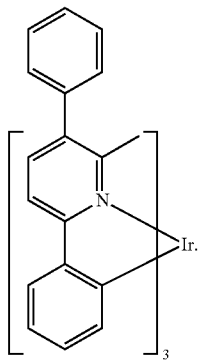

Compound 23

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| | Hole injection materials | |
| Phthalocyanine and porphryin compounds | | Appl. Phys. Lett. 69, 2160 (1996) |

TABLE 1-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | | Synth. Met. 87, 171 (1997) |
| Arylamines complexed with metal oxides such as molybdenum and tungsten oxides | + $MoO_x$ | SID Symposium Digest, 37, 923 (2006) |
| Hole transporting materials | | |
| Triarylamines (e.g., TPD, α-NPD) | | Appl. Phys. Lett. 51, 913 (1987) |
| | | U.S. Pat. No. 5,061,569 |

TABLE 1-continued
| MATERIAL | EXAMPLES OF MATERIAL | PUBLICATIONS |
|---|---|---|
| | 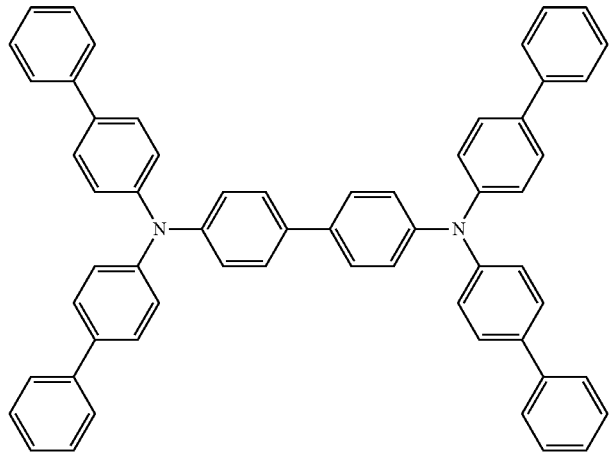 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 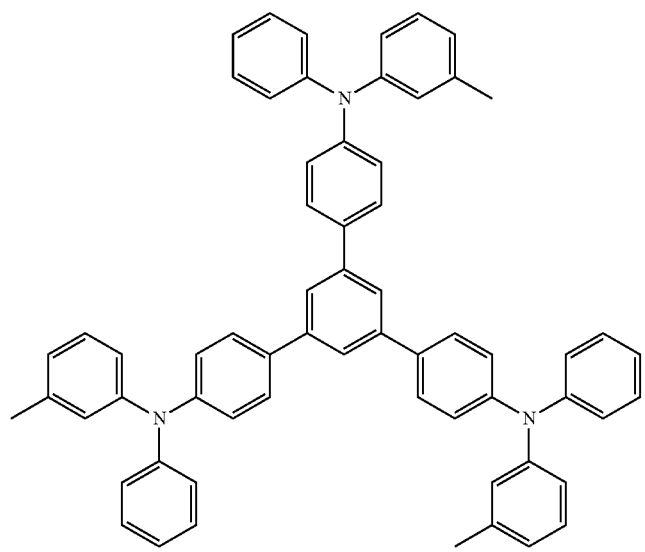 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 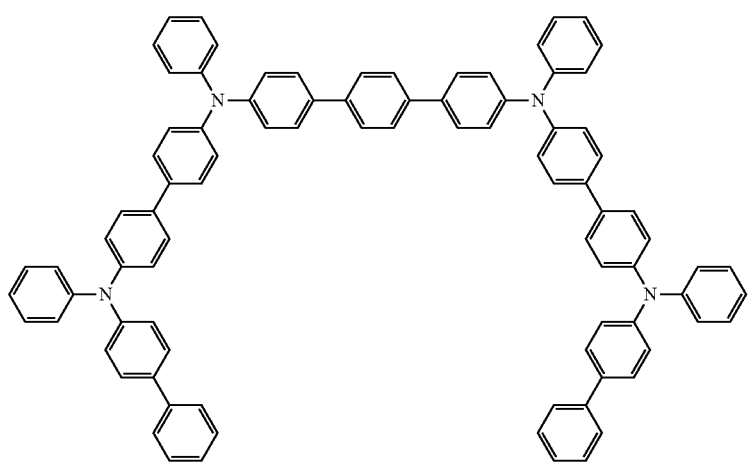 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued

| MATERIAL | EXAMPLES OF MATERIAL | PUBLICATIONS |
| --- | --- | --- |
|  |  | Appl. Phys. Lett. 90, 183503 (2007) |
| Triarylamine on spirofluorene core |  | Synth. Met. 91, 209 (1997) |
| Arylamine carbazole compounds |  | Adv. Mater. 6, 677 (1994) |
| Indolocarbazoles |  | Synth. Met. 111, 421 (2000) |

TABLE 1-continued

| MATERIAL | EXAMPLES OF MATERIAL | PUBLICATIONS |
| --- | --- | --- |
| Isoindole compounds | | Chem. Mater. 15, 3148 (2003) |

Phosphorescent OLED host materials

Red hosts

| | | |
| --- | --- | --- |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |

TABLE 1-continued

| MATERIAL | EXAMPLES OF MATERIAL | PUBLICATIONS |
| --- | --- | --- |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Green hosts | | |
| Arylcarbazoles | | Appl. Phys. Lett. 78, 1622 (2001) |
| | | US2003175553 |
| | | WO2001039234 |
| Aryltriphenylene compounds | | US20060280965 |

TABLE 1-continued

| MATERIAL | EXAMPLES OF MATERIAL | PUBLICATIONS |
|---|---|---|
| | | US20060280965 |
| Polymers (e.g., PVK) | | Appl. Phys. Lett. 77, 2280 (2000) |
| Spirofluorene compounds | | WO2004093207 |
| Metal phenoxybenzooxazole compounds | | WO05089025 |
| | | WO06132173 |

TABLE 1-continued

| MATERIAL | EXAMPLES OF MATERIAL | PUBLICATIONS |
|---|---|---|
| | | JP200511610 |
| Spirofluorene-carbazole compounds | | JP2007254297 |
| | | JP2007254297 |
| Indolocabazoles | | WO07063796 |

TABLE 1-continued
| MATERIAL | EXAMPLES OF MATERIAL | PUBLICATIONS |
|---|---|---|
| | 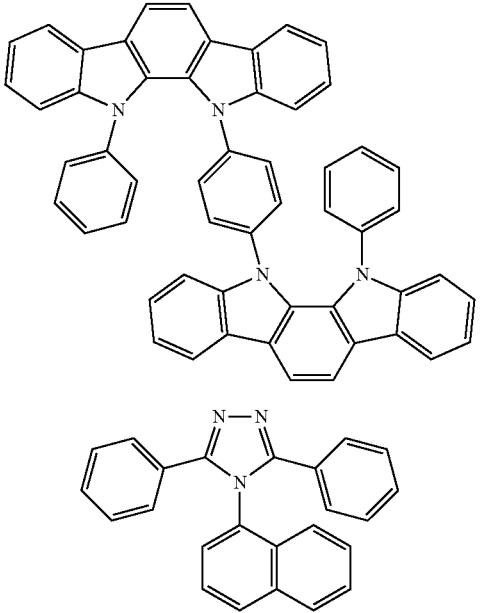 | WO07063754 |
| 5-member ring electron deficient heterocycles (e.g., triazole, oxadiazole) | 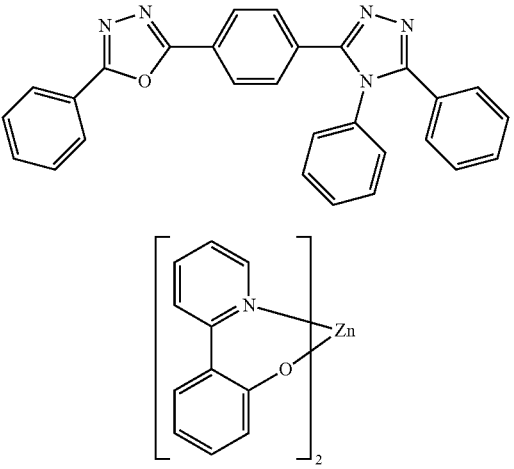 | J. Appl. Phys. 90, 5048 (2001) |
| | | WO04107822 |
| Metal phenoxypyridine compounds | 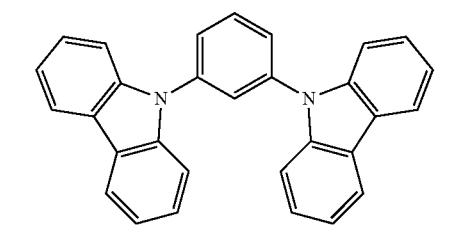 [SMILES: c1cc(-n2c3ccccc3c3ccccc32)cc(-n2c3ccccc3c3ccccc32)c1] | WO05030900 |
| Blue hosts | | |
| Arylcarbazoles | | Appl, Phys. Lett, 82, 2422 (2003) |
| | 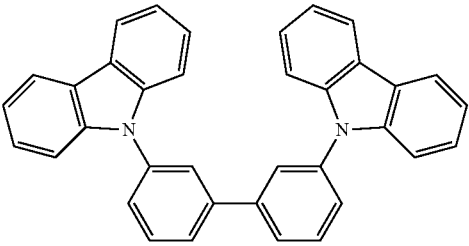 [SMILES: c1cc(-c2cccc(-n3c4ccccc4c4ccccc43)c2)cc(-n2c3ccccc3c3ccccc32)c1] | US20070190359 |

TABLE 1-continued
| MATERIAL | EXAMPLES OF MATERIAL | PUBLICATIONS |
| --- | --- | --- |
| Dibenzothiophene-carbazole compounds | 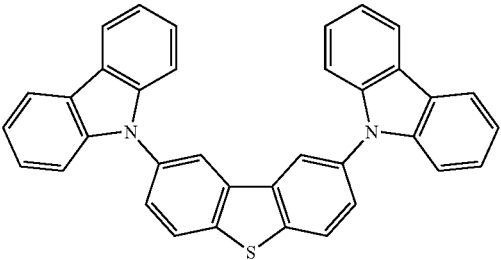 [SMILES: c1ccc2c(c1)c1ccccc1n2-c1ccc2sc3ccc(-n4c5ccccc5c5ccccc54)cc3c2c1] | WO2006114966 |
Phosphorescent dopants
Red dopants
| | | |
| --- | --- | --- |
| Heavy metal porphyrins (e.g., PtOEP) | 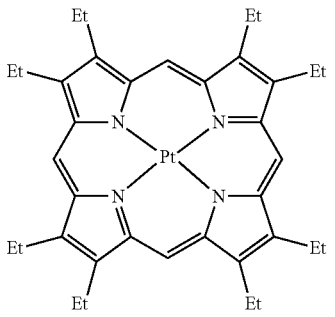 | Nature 395, 151 (1998) |
| Iridium(III) organometallic complexes | 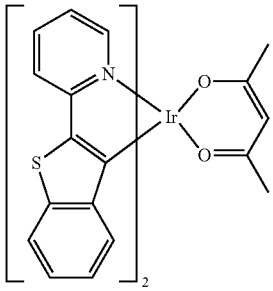 | Appl. Phys. Lett. 78, 1622 (2001) |
| | 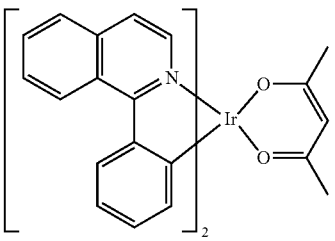 | U.S. Pat. No. 06,835,469 |
| | 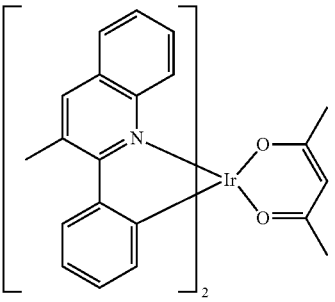 | U.S. Pat. No. 06,835,469 |

TABLE 1-continued

| MATERIAL | EXAMPLES OF MATERIAL | PUBLICATIONS |
|---|---|---|
| | | US20060202194 |
| | | US20060202194 |
| | | U.S. Pat. No. 07,087,321 |
| | | U.S. Pat. No. 07,087,321 |
| | | Adv. Mater. 19, 739 (2007) |

TABLE 1-continued

| MATERIAL | EXAMPLES OF MATERIAL | PUBLICATIONS |
| --- | --- | --- |
| Platinum(II) organometallic complexes | | WO2003040257 |
| Osmium(III) complexes | | Chem, Mater. 17, 3532 (2005) |
| Ruthenium(II) complexes | | Adv. Mater. 17, 1059 (2005) |

Green dopants

| | | |
| --- | --- | --- |
| Iridium(III) organometallic complexes | and its derivatives | Inorg. Chem. 40, 1704 (2001) |
| | | US2002034656 |

TABLE 1-continued

| MATERIAL | EXAMPLES OF MATERIAL | PUBLICATIONS |
|---|---|---|
| | | U.S. Pat. No. 06,687,266 |
| | | Chem. Mater. 16, 2480 (2004) |
| | | US2007190359 |
| | | US2006008670 JP2007123392 |
| | | Adv. Mater. 16, 2003 (2004) |

TABLE 1-continued

| MATERIAL | EXAMPLES OF MATERIAL | PUBLICATIONS |
|---|---|---|
| | | Angew. Chem. Int. Ed. 2006, 45, 7800 |
| Pt(II) organometallic complexes | | Appl. Phys. Lett. 86, 153505 (2005) |
| | | Appl. Phys. Lett. 86, 153505 (2005) |
| | | Chem. Lett. 34, 592 (2005) |

TABLE 1-continued
| MATERIAL | EXAMPLES OF MATERIAL | PUBLICATIONS |
|---|---|---|
| Gold complexes | 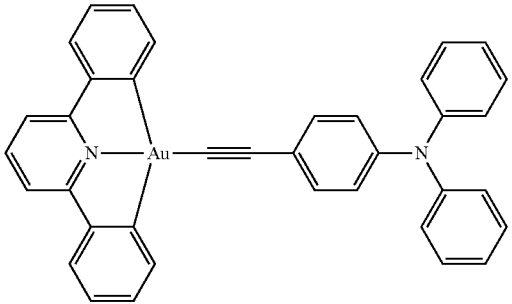 | Chem. Commun. 2906 (2005) |
| Rhenium(III) complexes | 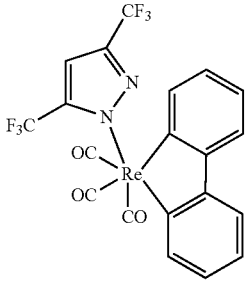 | Inorg. Chem. 42, 1248 (2003) |
| Blue dopants | | |
| Iridium(III) organometallic Complexes | 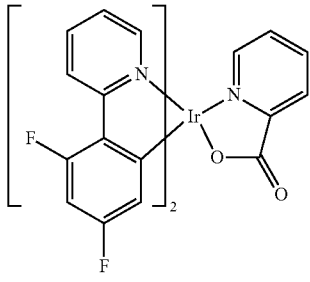 | WO2002002714 |
| | 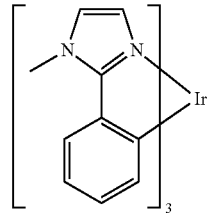 | WO2006009024 |
| | 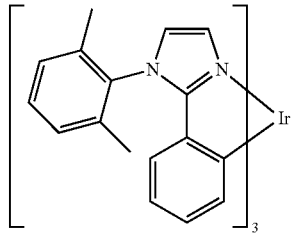 | US2006251923 |

TABLE 1-continued
| MATERIAL | EXAMPLES OF MATERIAL | PUBLICATIONS |
|---|---|---|
| | 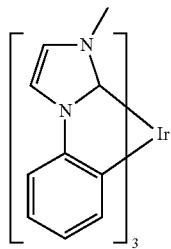 | WO2006056418, US2005260441 |
| | 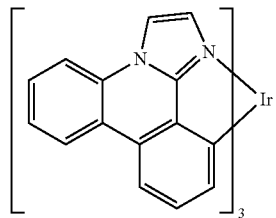 | US2007190359 |
| | 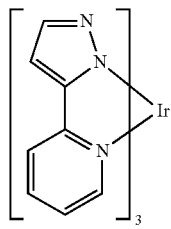 | US2002134984 |
| | 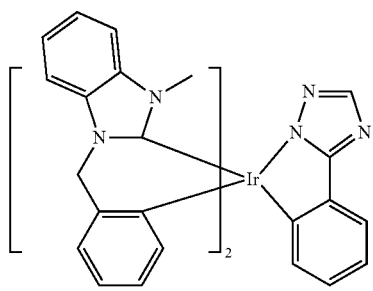 | Angew. Chem. Int. Ed. 47, 1 (2008) |
| | 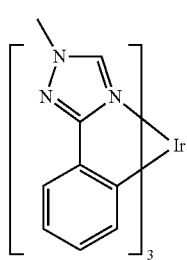 | Chem. Mater. 18, 5119 (2006) |
| | 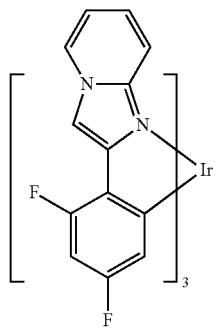 | Inorg. Chem. 46, 4308 (2007) |

TABLE 1-continued
| MATERIAL | EXAMPLES OF MATERIAL | PUBLICATIONS |
|---|---|---|
| | 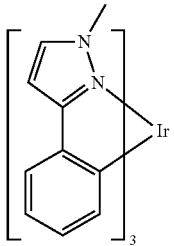 | WO05123873 |
| | 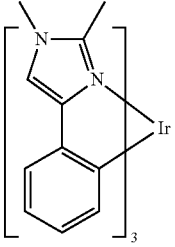 | WO05123873 |
| | 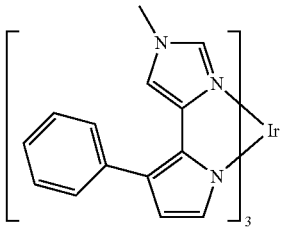 | WO07004380 |
| | 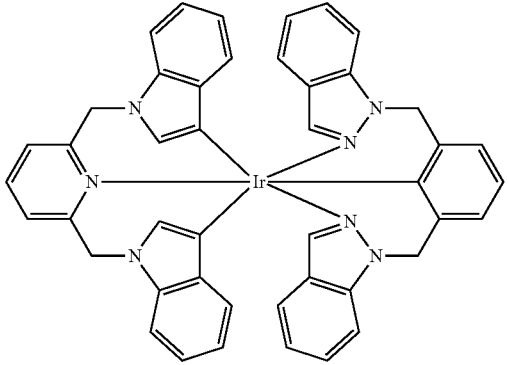 | WO06082742 |
| Osmium(II) complexes | 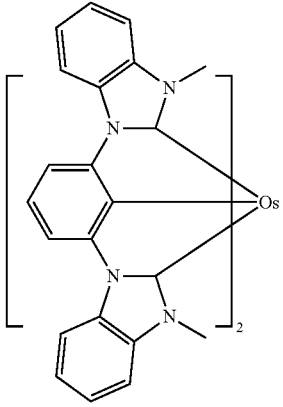 | US2005260449 |

TABLE 1-continued

| MATERIAL | EXAMPLES OF MATERIAL | PUBLICATIONS |
| --- | --- | --- |
| | [Os(PPh₃) complex structure]₂ | Organometallics 23, 3745 (2004) |
| Gold complexes | Ph₂P–PPh₂ / Cl–Au  Au–Cl | Appl. Phys. Lett. 74, 1361 (1999) |
| Platinum(II) complexes | [Pt complex with thiophene and pyrazolylborate structure] | WO06098120, WO06103874 |

Exciton/hole blocking layer materials

| MATERIAL | EXAMPLES OF MATERIAL | PUBLICATIONS |
| --- | --- | --- |
| Bathocuprine compounds (e.g., BCP, BPhen) | [BCP structure] | Appl. Phys. Lett. 75, 4 (1999) |
| | [BPhen structure] | Appl. Phys. Lett. 79, 449 (2001) |
| Metal 8-hydroxyquinolates (e.g., BAlq) | [BAlq structure] | Appl. Phys. Lett. 81, 162 (2002) |

TABLE 1-continued

| MATERIAL | EXAMPLES OF MATERIAL | PUBLICATIONS |
|---|---|---|
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 1-continued

| MATERIAL | EXAMPLES OF MATERIAL | PUBLICATIONS |
| --- | --- | --- |

Electron transporting materials

| | | |
| --- | --- | --- |
| Anthracene-benzoimidazole compounds | | WO03060956 |
| Anthracene-benzothiazole compounds | | Appl. Phys. Lett. 89, 063504 (2006) |
| Metal 8-hydroxyquinolates (e.g., $Alq_3$) | | Appl. Phys. Lett. 51, 913 (1987) |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |

TABLE 1-continued

| MATERIAL | EXAMPLES OF MATERIAL | PUBLICATIONS |
|---|---|---|
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |

| MATERIAL | EXAMPLES OF MATERIAL | PUBLICATIONS |
|---|---|---|
| Fluorinated aromatic compounds | 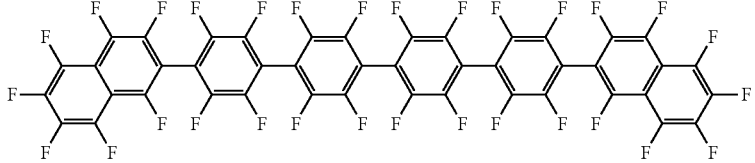 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

EXPERIMENTAL

Compound Examples

Some heteroleptic Ir (III) complexes were synthesized as follows:

Example 1. Synthesis of Compound 1

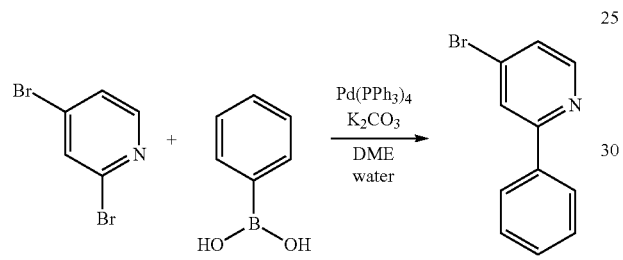

Synthesis of 2-phenyl-4-bromopyridine

A mixture was prepared of 2,4-dibromopyridine (10 g, 42.21 mmol), phenylboronic acid (5.1 g, 42.21 mmol), and potassium carbonate (11.7 g, 84.42 mmol) in 100 mL dimethoxyethane and 40 mL of water. Nitrogen was bubbled directly into the mixture for 30 minutes. Next, tetrakis (triphenylphosphine)palladium(0) was added (244 mg, 2.11 mmol) and the mixture was heated to reflux under nitrogen overnight. The mixture was cooled and diluted with ethyl acetate and water. The layers were separated and the aqueous layer was extracted with ethyl acetate. The organic layers were washed with brine, dried over magnesium sulfate, filtered, and evaporated to a residue. The residue was purified by column chromatography eluting with 0, 2, and 5% ethyl acetate/hexanes. Obtained 4.28 g of a yellow liquid (43%).

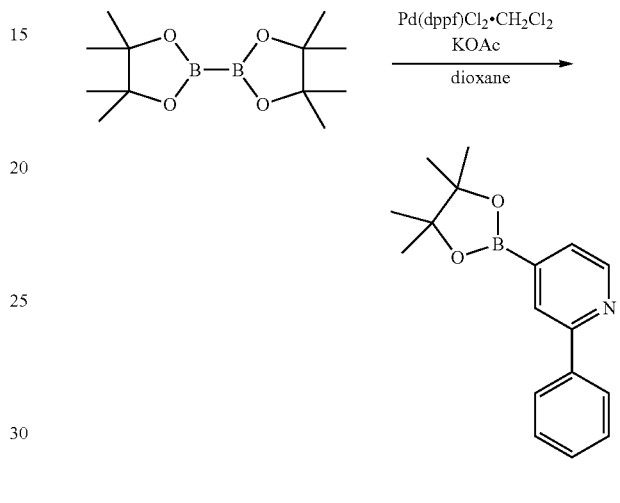

Synthesis of 2-phenyl-4(4,4,5,5-tetramethyl-1,3,2-dioxaborolan-2yl)pyridine

A mixture was prepared of 2-phenyl-4-bromopyridine (4.28 g, 18.28 mmol), bis(pinacolato)diboron (9.29 g, 36.57 mmol), and potassium acetate (5.38 g, 54.84 mmol) in 100 mL of dioxane. Nitrogen was bubbled directly into the mixture for 30 minutes. Dichloro[1,1'-ferrocenylbis(diphenylphosphine)]palladium(II) dichloromethane (448 mg, 0.55 mmol) was added, and nitrogen bubbled for another 15 minutes. The reaction mixture was heated to 90° C. internally. After 1 h the reaction was complete, and the heat was shut off. The solvent was evaporated to an oil. The oil was purified by Kugelrohr at 200° C. to remove excess bis (pinacolato)diboron. The residue left in the boiling pot was dissolved in ethyl acetate and filtered through magnesium sulfate, rinsed with ethyl acetate, and the filtrate was evaporated. Used as described in the next step. Yield was approximately 4 g of product.

Synthesis of PPY Dimer

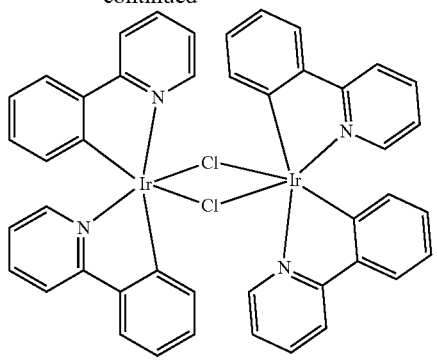

14.7 g (0.04 mol) of iridium chloride and 26.0 g (0.17 mol) of 2-phenylpyridine was placed in a 1 L round bottomed flask. 300 ml of 2-ethocyethanol and 100 ml of water was added. The mixture was refluxed under nitrogen atmosphere overnight. After having cooled to room temperature, the precipitate was filtered and washed with methanol. After drying, 22 g of dimer was obtained. (99% yield).

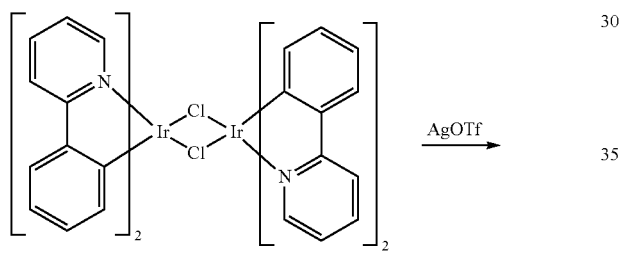

Synthesis of Triflate

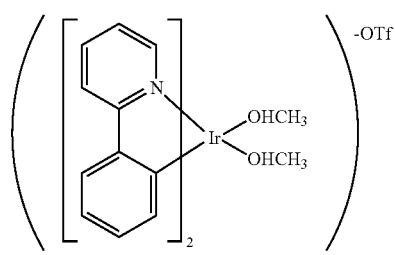

22 g of dimer was dissolved in 1 L of dichloromethane. 10.5 g (0.04 mol) of silver triflate was added to the solution. 25 ml of methanol was then added. The solution was stirred for 5 h. The silver chloride was filtered off. The solvent was evaporated. 26 g of product was obtained. The solid was used for next step without further purification.

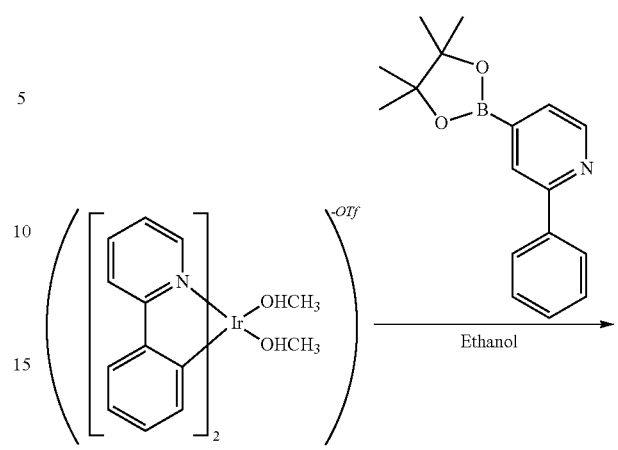

Synthesis of Boronic Ester Precursor

A mixture was prepared of the triflate (4.6 g, 7.11 mmol) and 2-phenyl-4(4,4,5,5-tetramethyl-1,3,2-dioxaborolan-2yl) pyridine (~4 g, ~14.23 mmol) in 100 mL of ethanol. The mixture was heated at reflux for 6 h under nitrogen. The solvent was evaporated and hexanes was added. A sold was filtered off which was washed with hexanes. The solid was purified by column chromatography eluting with dichloromethane and later some methanol was added. Obtained 0.92 g of an orange solid (approximately 17%).

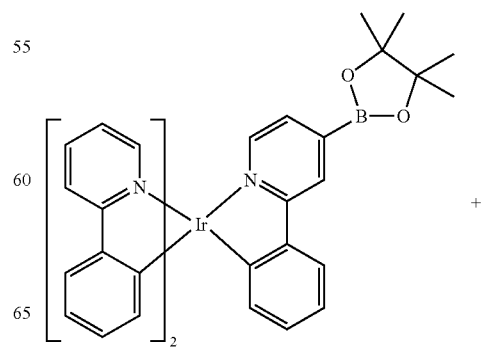

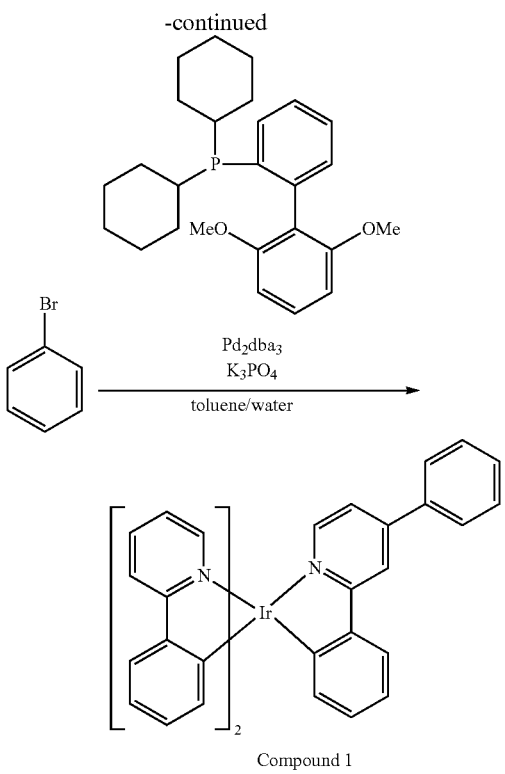

Compound 1

Synthesis of Compound 1

Mixed the boronic ester precursor (0.92 g, 1.18 mmol), bromobenzene (0.6 g, 3.54 mmol), 2-dicyclohexylphosphino-2', 6'-dimethoxybiphenyl (19 mg, 0.047 mmol), and potassium phosphate tribasic (0.82 g, 3.54 mmol) in 50 mL of tolune and 5 mL of water. Bubbled nitrogen directly into the mixture for 30 minutes after which tris(dibenzylideneacetone)dipalladium(0) (11 mg, 0.0118 mmol) was added. Nitrogen was bubbled for another 5 minutes then the reaction mixture was heated to reflux for 1 h under nitrogen. The mixture was cooled and an orange solid precipitated out. The solid was filtered off and washed with hexanes followed by methanol. Some solid was seen in filtrate so the filtrate was evaporated and methanol was added. More orange solid was filtered off. All the solid was purified by column chromatography eluting with 50% dichloromethane/hexanes. The solid was sublimed at 280° C. Obtained 0.53 g (62%).

Example 2. Synthesis of Compound 2

The following synthesis could be used to make Compound 2.

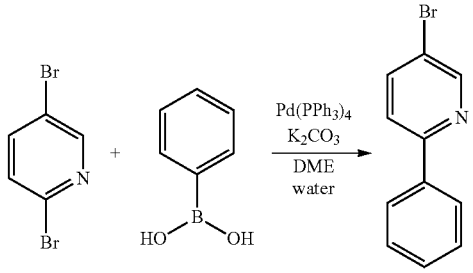 [SMILES: Brc1ccc(Br)nc1 ; OB(O)c1ccccc1 ; Brc1ccc(-c2ccccc2)nc1]

Synthesis of 2-phenyl-5-bromopyridine

A mixture is prepared of 2,5-dibromopyridine (10 g, 42.21 mmol), phenylboronic acid (5.1 g, 42.21 mmol), and potassium carbonate (11.7 g, 84.42 mmol) in 100 mL dimethoxyethane and 40 mL of water. Nitrogen is bubbled directly into the mixture for 30 minutes. Next, tetrakis(triphenylphosphine)palladium(0) was added (244 mg, 2.11 mmol) and the mixture is heated to reflux under nitrogen overnight. The mixture is cooled and diluted with ethyl acetate and water. The layers are separated and the aqueous layer is extracted with ethyl acetate. The organic layers are washed with brine, dried over magnesium sulfate, filtered, and evaporated to a residue. The residue is purified by column chromatography eluting with 0, 2, and 5% ethyl acetate/hexanes.

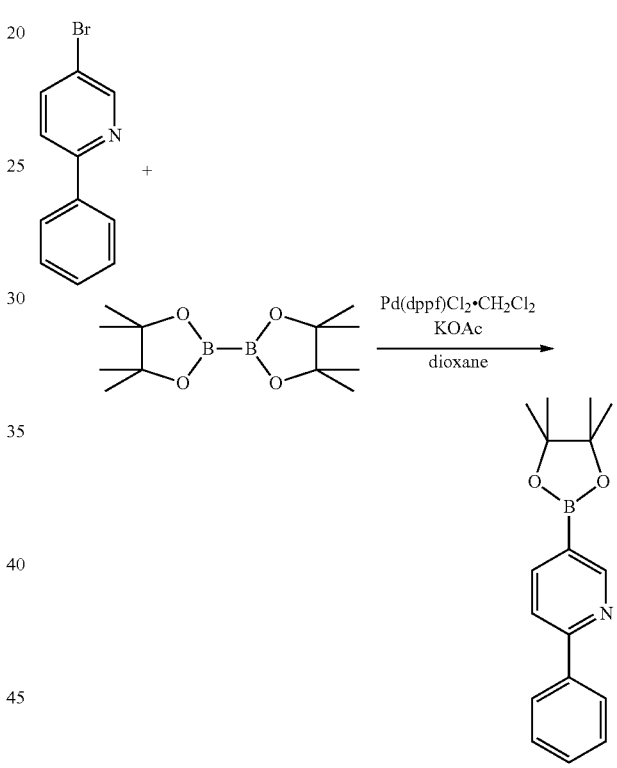

Synthesis of 2-phenyl-5-(4,4,5,5-tetramethyl-1,3,2-dioxaborolan-2-yl)pyridine

A mixture is prepared of 2-phenyl-4-bromopyridine (4.28 g, 18.28 mmol), bis(pinacolato)diboron (9.29 g, 36.57 mmol), and potassium acetate (5.38 g, 54.84 mmol) in 100 mL of dioxane. Nitrogen is bubbled directly into the mixture for 30 minutes. Dichloro[1,1'-ferrocenylbis(diphenylphosphine)]palladium(II) dichloromethane (448 mg, 0.55 mmol) is added. The reaction mixture is heated to 90° C. internally for 3 h. The solvent is evaporated to an oil. The oil was purified by Kugelrohr to remove excess bis(pinacolato)diboron. The residue left in the boiling pot is dissolved in ethyl acetate and filtered through magnesium sulfate, rinsed with ethyl acetate, and the filtrate is evaporated. The product can be used without purification in the next step.

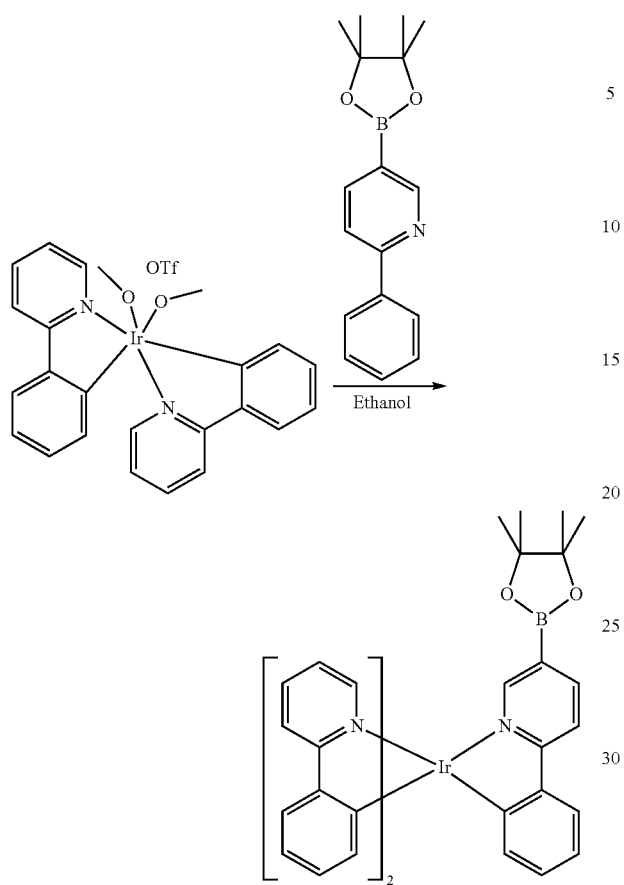

Synthesis of Boronic Ester Precursor

A mixture is prepared of the triflate (4.6 g, 7.11 mmol) and 2-phenyl-5-(4,4,5,5-tetramethyl-1,3,2-dioxaborolan-2yl) pyridine (~4 g, ~14.23 mmol) in 100 mL of ethanol. The mixture is heated at reflux for 24 h under nitrogen. The solvent is evaporated and hexanes is added. A sold is filtered off which is washed with hexanes. The solid is purified by column chromatography eluting with dichloromethane and later some methanol is added.

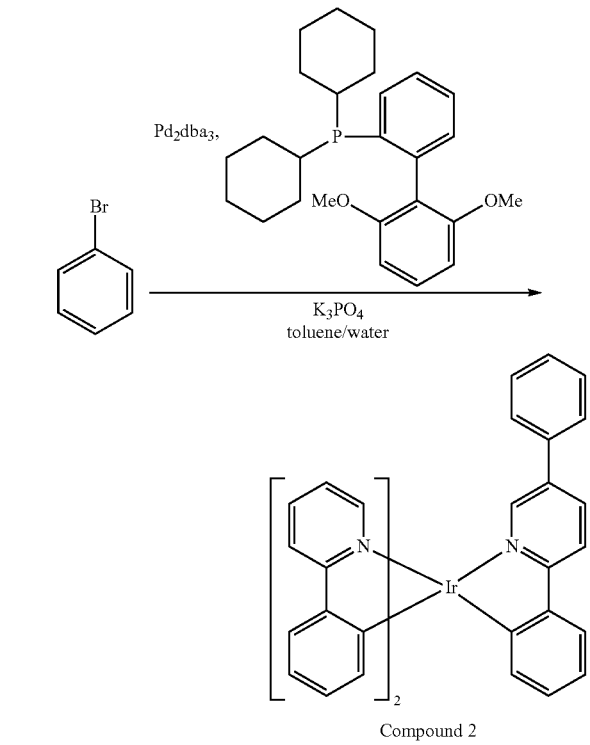

Synthesis of Compound 2

The boronic ester precursor (0.92 g, 1.18 mmol), bromobenzene (0.6 g, 3.54 mmol), 2-dicyclohexylphosphino-2',6'-dimethoxybiphenyl (19 mg, 0.047 mmol), and potassium phosphate tribasic (0.82 g, 3.54 mmol) are mixed in 50 mL of tolune and 5 mL of water. Nitrogen is bubbled directly into the mixture for 30 minutes after which tris(dibenzylideneacetone)dipalladium(0) (11 mg, 0.0118 mmol) is added. Nitrogen is bubbled for another 5 minutes then the reaction mixture is heated to reflux for 1 h under nitrogen. The mixture is cooled and an orange solid formed. The solid is filtered off and washed with hexanes followed by methanol. The solid is purified by column chromatography eluting with 50% dichloromethane/hexanes.

Example 3. Synthesis of Compound 3

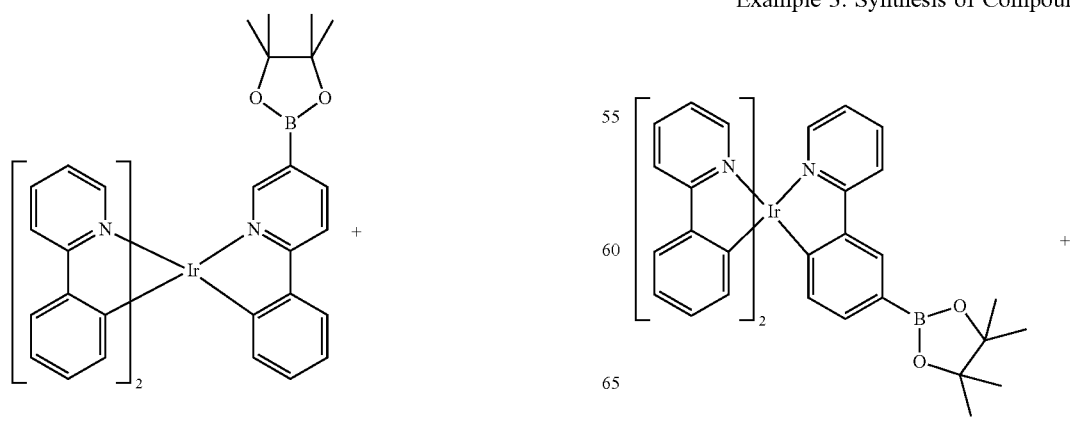

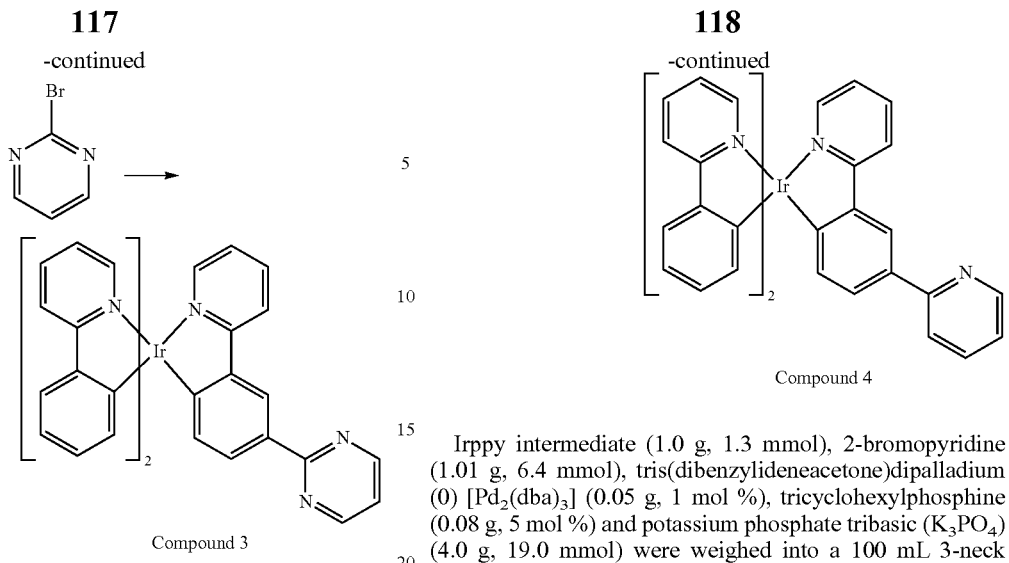

Compound 3

Irppy intermediate (0.70 g, 0.90 mmol), 2-bromopyrimidine (0.71 g, 4.5 mmol), tris(dibenzylideneacetone)dipalladium(0) [$Pd_2(dba)_3$] (0.01 g, 1 mol %), tricyclohexylphosphine (0.05 g, 0.18 mmol) and potassium phosphate tribasic ($K_3PO_4$) (0.7 g, 3.3 mmol) were weighed into a 100 mL 3-neck round bottom flask. 40 mL toluene and 10 mL water were added to the reaction vessel. The reaction mixture was degassed by bubbling nitrogen directly in the mixture for an hour. The solution was heated to reflux for 2 h. After cooling, the product was filtered, dissolved in methylene chloride and chromatographed using silica gel with methylene chloride:hexanes (50:50) as the mobile phase. The solvent was removed using the rotary evaporator and the product dried under vacuum to give 0.6 g of product (90% yield).

Example 4. Synthesis of Compound 4

Compound 4

Irppy intermediate (1.0 g, 1.3 mmol), 2-bromopyridine (1.01 g, 6.4 mmol), tris(dibenzylideneacetone)dipalladium(0) [$Pd_2(dba)_3$] (0.05 g, 1 mol %), tricyclohexylphosphine (0.08 g, 5 mol %) and potassium phosphate tribasic ($K_3PO_4$) (4.0 g, 19.0 mmol) were weighed into a 100 mL 3-neck round bottom flask. 50 mL dioxane and 10 mL water were added to the reaction vessel. The reaction mixture was degassed by bubbling nitrogen directly in the mixture for an hour. The solution was heated to reflux for 2 h. After cooling, the product was filtered, dissolved in methylene chloride and chromatographed using silica gel with methylene chloride:hexanes (50:50) as the mobile phase. The solvent was removed using the rotary evaporator and the product dried under vacuum to give 0.8 g of product (86% yield).

Example 5. Synthesis of Compound 5

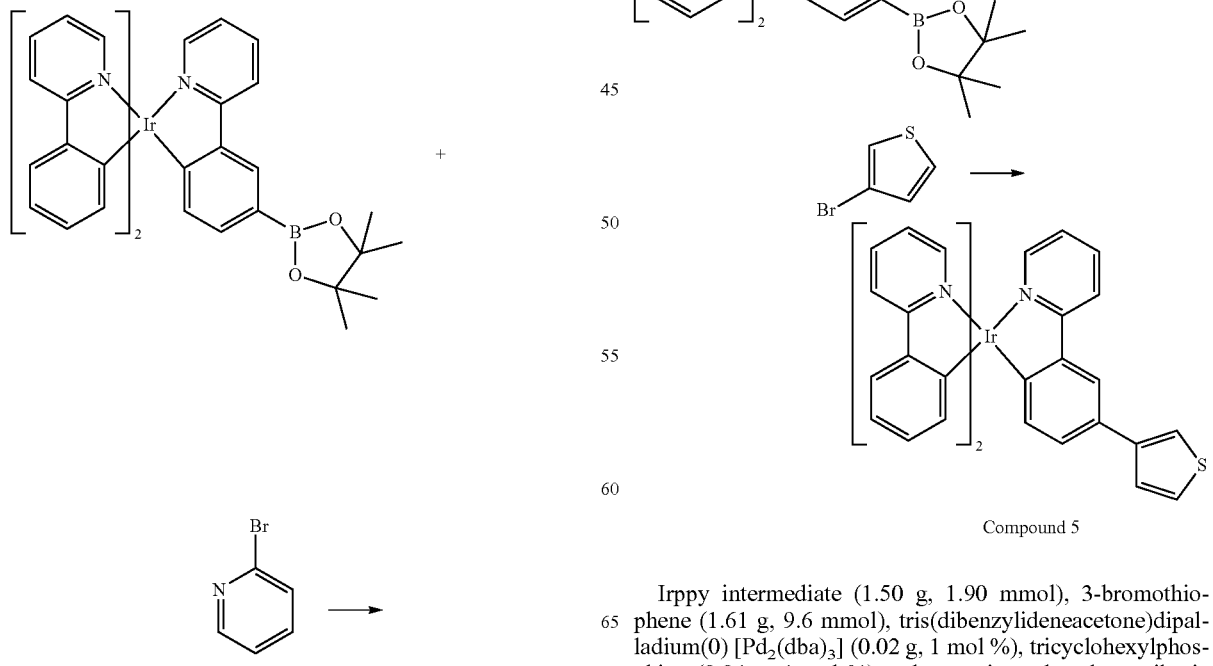

Compound 5

Irppy intermediate (1.50 g, 1.90 mmol), 3-bromothiophene (1.61 g, 9.6 mmol), tris(dibenzylideneacetone)dipalladium(0) [$Pd_2(dba)_3$] (0.02 g, 1 mol %), tricyclohexylphosphine (0.04 g, 4 mol %) and potassium phosphate tribasic ($K_3PO_4$) (1.2 g, 5.6 mmol) were weighed into a 250 mL 3-neck round bottom flask. 100 mL toluene and 10 mL water were added to the reaction vessel. The reaction mixture was degassed by bubbling nitrogen directly in the mixture for an hour. The solution was heated to reflux for 2 h. After cooling, the product was filtered, dissolved in methylene chloride and chromatographed using silica gel with methylene chloride:hexanes (50:50) as the mobile phase. The solvent was removed using the rotary evaporator and the product dried under vacuum to give 1.0 g of product (74% yield).

Example 6. Synthesis of Compound 6

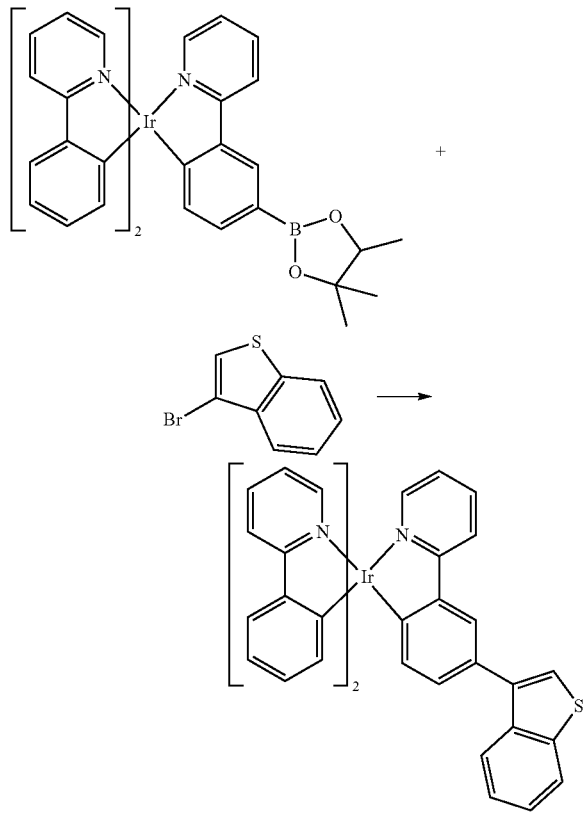

Compound 6

Irppy intermediate (1.50 g, 1.90 mmol), 3-bromothianaphthene (2.0 g, 9.6 mmol), tris(dibenzylideneacetone)dipalladium(0) [$Pd_2(dba)_3$] (0.08 g, 1 mol %), tricyclohexylphosphine (0.2 g, 0.5 mmol) and potassium phosphate tribasic ($K_3PO_4$) (1.2 g, 5.6 mmol) were weighed into a 250 mL 3-neck round bottom flask. 100 mL toluene and 10 mL water were added to the reaction vessel. The reaction mixture was degassed by bubbling nitrogen directly in the mixture for an hour. The solution was heated to reflux for 2 h. After cooling, the product was filtered, dissolved in methylene chloride and chromatographed using silica gel with methylene chloride:hexanes (50:50) as the mobile phase. The solvent was removed using the rotary evaporator and the product dried under vacuum to give 1.2 g of product (80% yield).

Example 7. Synthesis of Compound 7

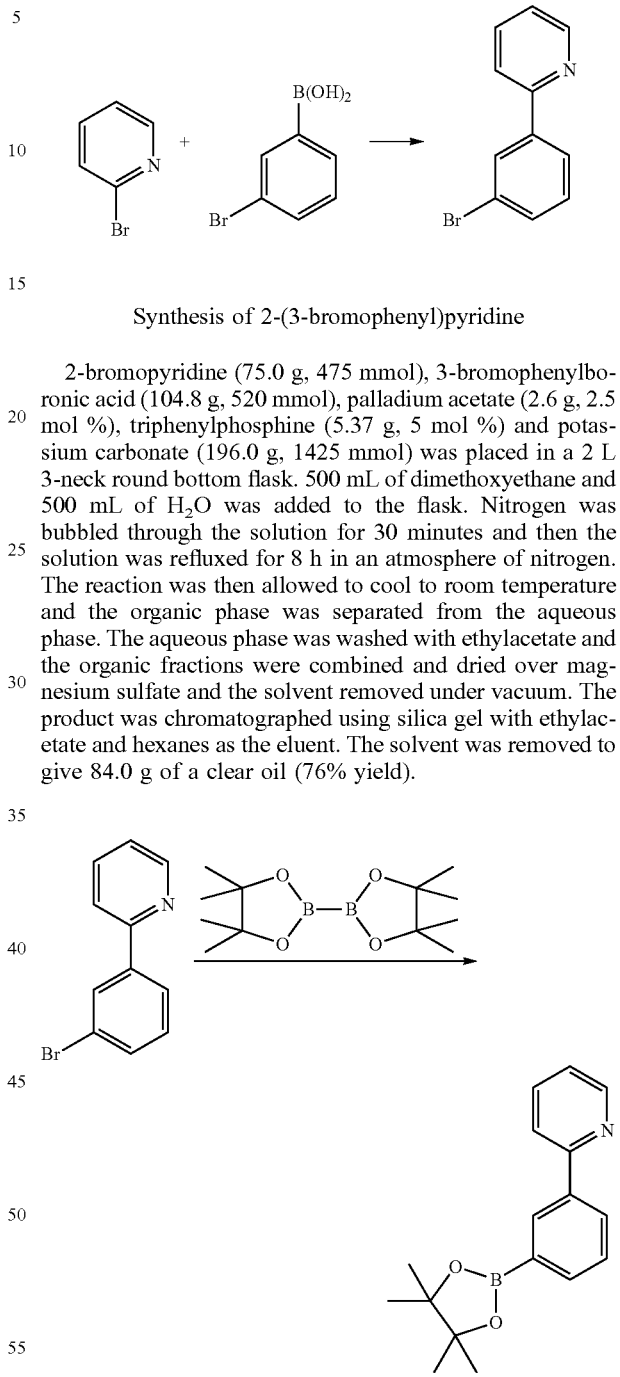

Synthesis of 2-(3-bromophenyl)pyridine 2-bromopyridine (75.0 g, 475 mmol), 3-bromophenylboronic acid (104.8 g, 520 mmol), palladium acetate (2.6 g, 2.5 mol %), triphenylphosphine (5.37 g, 5 mol %) and potassium carbonate (196.0 g, 1425 mmol) was placed in a 2 L 3-neck round bottom flask. 500 mL of dimethoxyethane and 500 mL of $H_2O$ was added to the flask. Nitrogen was bubbled through the solution for 30 minutes and then the solution was refluxed for 8 h in an atmosphere of nitrogen. The reaction was then allowed to cool to room temperature and the organic phase was separated from the aqueous phase. The aqueous phase was washed with ethylacetate and the organic fractions were combined and dried over magnesium sulfate and the solvent removed under vacuum. The product was chromatographed using silica gel with ethylacetate and hexanes as the eluent. The solvent was removed to give 84.0 g of a clear oil (76% yield).

Synthesis of 2-(3-(4,4,5,5-tetramethyl-1,3,2-dioxaborolan-2-yl)phenyl)pyridine 2-(3-bromophenyl)pyridine (25.0 g, 107 mmol), bis(pinacolato)diboron (54.2 g, 214 mmol), $Pd(dppf)_2Cl_2$ (1.0 g, 10 mol %), and potassium acetate (31.5 g, 321 mmol) were placed in 1 L round bottom flask. 600 mL of dioxane was then added to the flask. Nitrogen was bubbled into the reaction mixture for 1 h and then the flask was heated to 90°

C. for 12 h in an atmosphere of nitrogen. The dioxane was removed under reduced pressure by a rotary evaporator. The dark solid was dissolved in 400 mL of dichloromethane and passed through a 2 inch thick silica gel plug. The dichloromethane was removed under reduced pressure by a rotary evaporator to leave a yellow oil. The product was then distilled using a Kuglerohr apparatus to give 23 g of a white solid (77% yield).

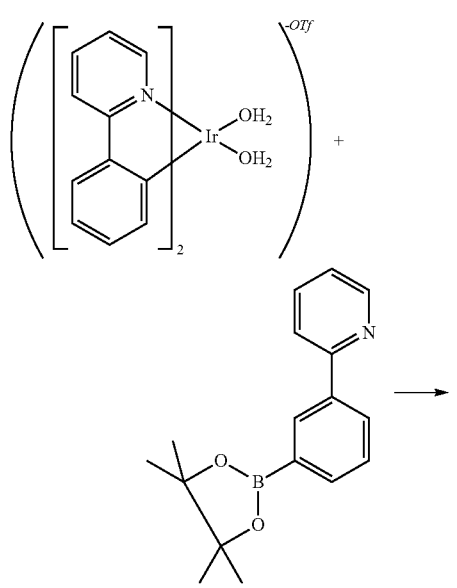

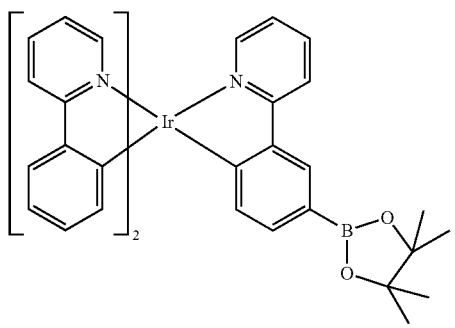

Synthesis of Irppy Intermediate

Irppy triflate (17.5 g, 25 mmol) and 3 molar equivalent 2-(3-(4,4,5,5-tetramethyl-1,3,2-dioxaborolan-2-yl)phenyl) pyridine (21.50 g, 117 mmol) was placed in a 2 L 3 neck round bottomed flask. 600 mL of alcohol was added to the reaction mixture. The reaction mixture was degassed by bubbling nitrogen directly in the mixture for an hour. The reaction mixture was then refluxed (internal temp of the reaction mixture was 78 degrees) for overnight. After about 18 h the product had already precipitated from the hot reaction mixture. After cooling to room temperature 200 mL isopropanol was added to precipitate any more product from the reaction mixture. The reaction mixture was then filtered and the product/residue was washed with isopropanol (to remove excess ligand) and then air dried to give 12 g of product (60% yield).

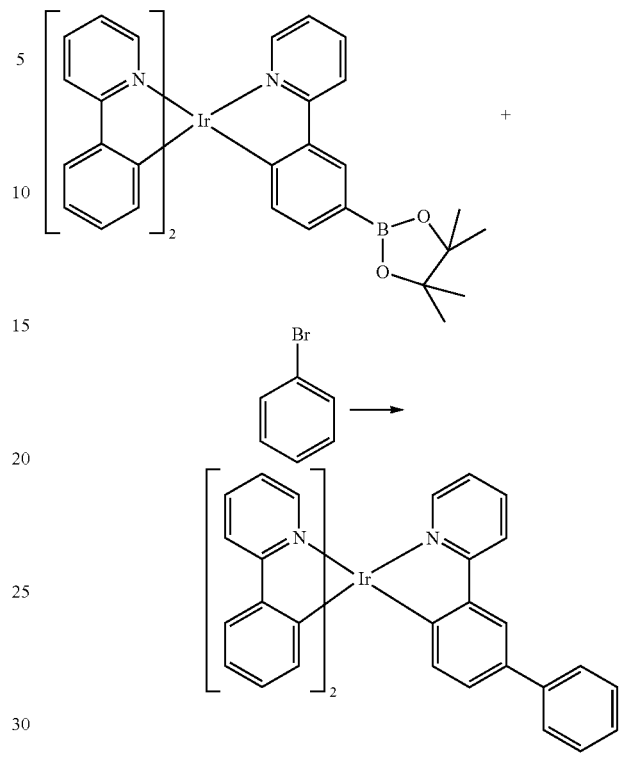

Synthesis of Compound 7

Irppy intermediate (0.50 g, 0.64 mmol), bromobenzene (0.5 g, 3.2 mmol), tris(dibenzylideneacetone)dipalladium(0) [Pd$_2$(dba)$_3$] (0.006 g, 0.0064 mmol), 2-dicyclohexylphosphino-2', 6'-dimethoxybiphenyl (0.10 g, 0.025 mmol) and potassium phosphate tribasic (K$_3$PO$_4$) (0.4 g, 1.92 mmol) were weighed into a 100 mL 3 neck round bottom flask. 40 mL toluene and 10 mL water were added to the reaction vessel. The reaction mixture was degassed by bubbling nitrogen directly in the mixture for an hour. The solution was heated to reflux for 2 h. After cooling, the product was filtered, dissolved in methylene chloride and chromatographed using silica gel with methylene chloride:hexanes (50:50) as the mobile phase. The solvent was removed using the rotary evaporator and the product dried under vacuum to give 0.5 g of product (95% yield).

Example 8. Synthesis of Compound 2

This following alternate synthesis was used to make Compound 2.

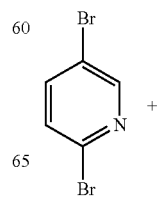

123
-continued

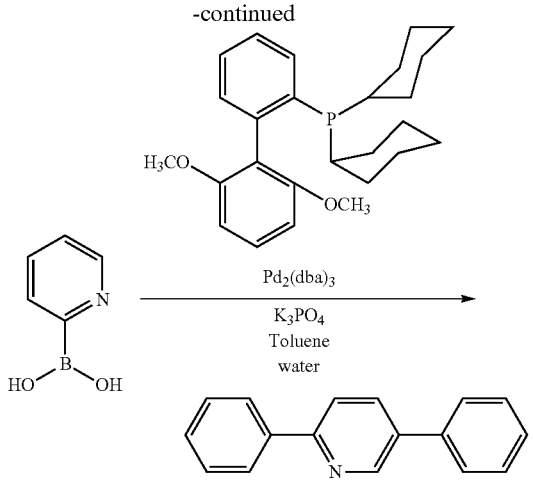

Synthesis of 2, 5-diphenylpyridine 2,5-dibromopyridine (10 g, 42 mmol), phenylboronic acid (13.4 g, 110 mmol), dicyclohexyl(2', 6'-dimethoxybiphenyl-2-yl)phosphine (S-Phos) (0.7 g, 1.6 mmol), and potassium phosphate (22 g, 105 mmol) were mixed in 200 mL of toluene and 20 mL of water. Nitrogen is bubbled directly into the mixture for 30 minutes. Next, $Pd_2(dba)_3$ was added (0.38 g, 0.4 mmol) and the mixture was heated to reflux under nitrogen for 2 h. The mixture was cooled and the organic layer was separated. The organic layers are washed with brine, dried over magnesium sulfate, filtered, and evaporated to a residue. The residue was purified by column chromatography eluting with 10% ethyl acetate/hexanes. 7 g of desired product was obtained after purification. (91.8% yield)

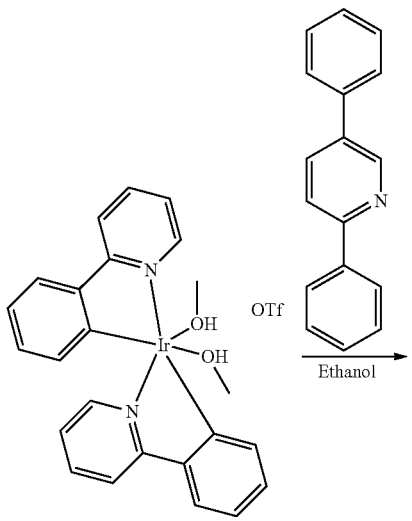

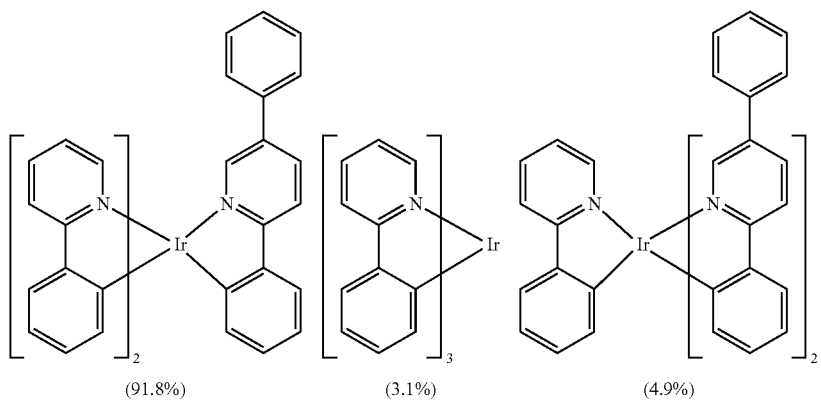

(91.8%)     (3.1%)     (4.9%)

Compound 2

Synthesis of Compound 2

The iridium triflate precursor (2.5 g, 3.5 mmol) and 2,5-diphenylpyridine (2.4 g, 11 mmol) were mixed in 200 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.2 g of pure product was obtained after the column purification. (HPLC purity: 99.8%)

Example 9. Alternate Synthesis of Compound 7

The following alternate synthesis was used to make Compound 2.

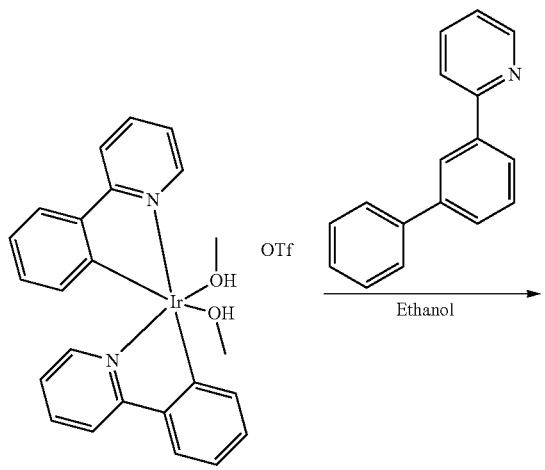

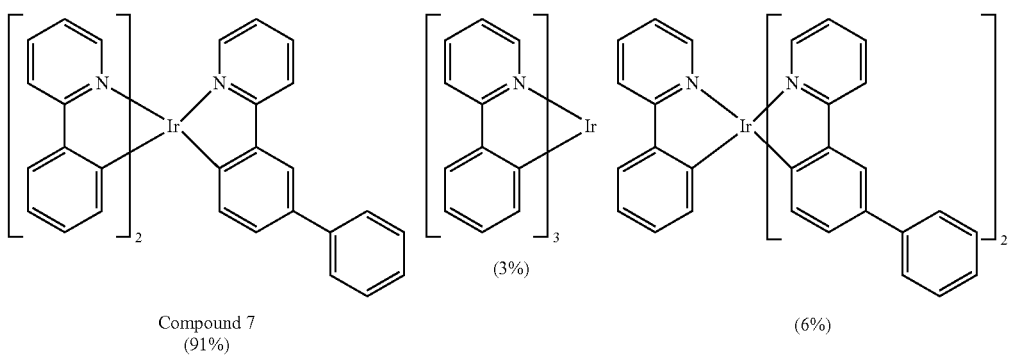

Compound 7 (91%)

(3%)

(6%)

The iridium triflate precursor (2.5 g, 3.5 mmol) and 2-(biphenyl-3-yl)pyridine (2.4 g, 11 mmol) were mixed in 200 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.5 g of pure product was obtained after the column purification, (HPLC purity: 99.6%)

Example 10. Synthesis of Compound 8

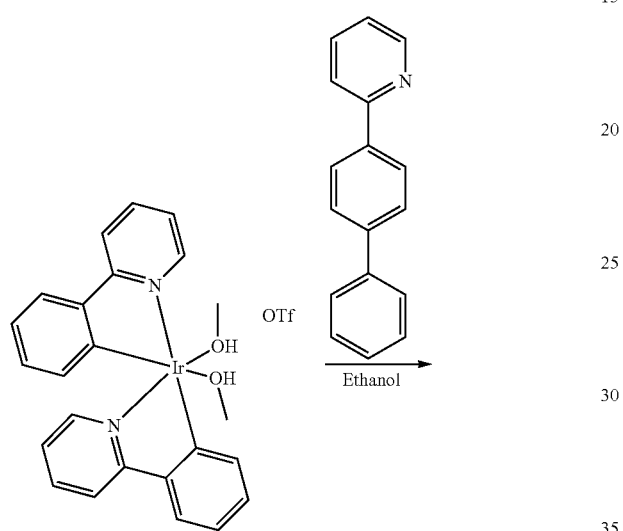

Example 11. Synthesis of Compound 9

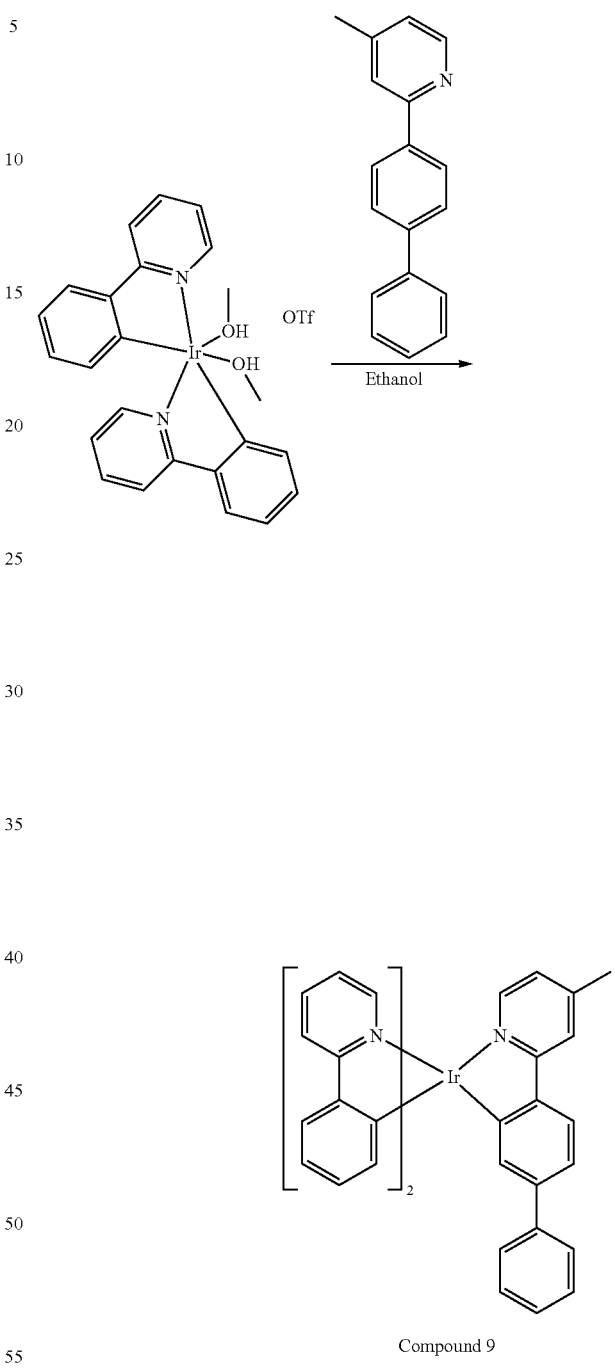

Compound 8

The iridium triflate precursor (2.5 g, 3.5 mmol) and 2-(biphenyl-4-yl)pyridine (2.4 g, 11 mmol) were mixed in 100 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.2 g of pure product was obtained after the column purification. (HPLC purity: 99.8%)

The iridium triflate precursor (2.5 g, 3.5 mmol) and 2-(biphenyl-4-yl)-4-methylpyridine (2.6 g, 11 mmol) were mixed in 100 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.3 g of pure product was obtained after the column purification. (HPLC purity: 99.9%)

Example 12. Synthesis of Compound 10

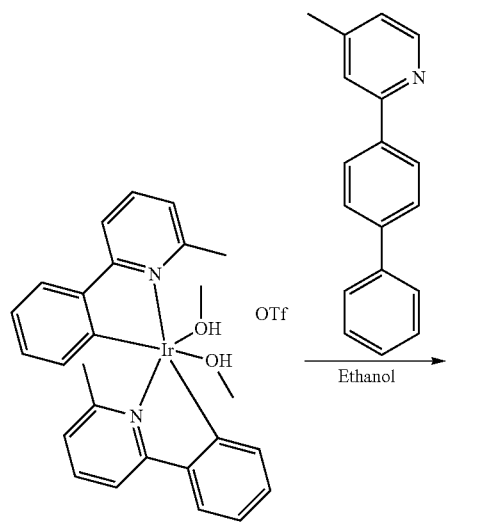

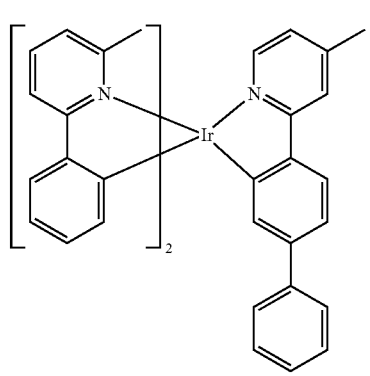

Compound 10

The iridium triflate precursor (2.0 g, 2.7 mmol) and 2-(biphenyl-4-yl)-4-methylpyridine (2.0 g, 8.2 mmol) were mixed in 60 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.6 g of pure product was obtained after the column purification. (HPLC purity: 99.4%)

Example 13. Synthesis of Compound 11

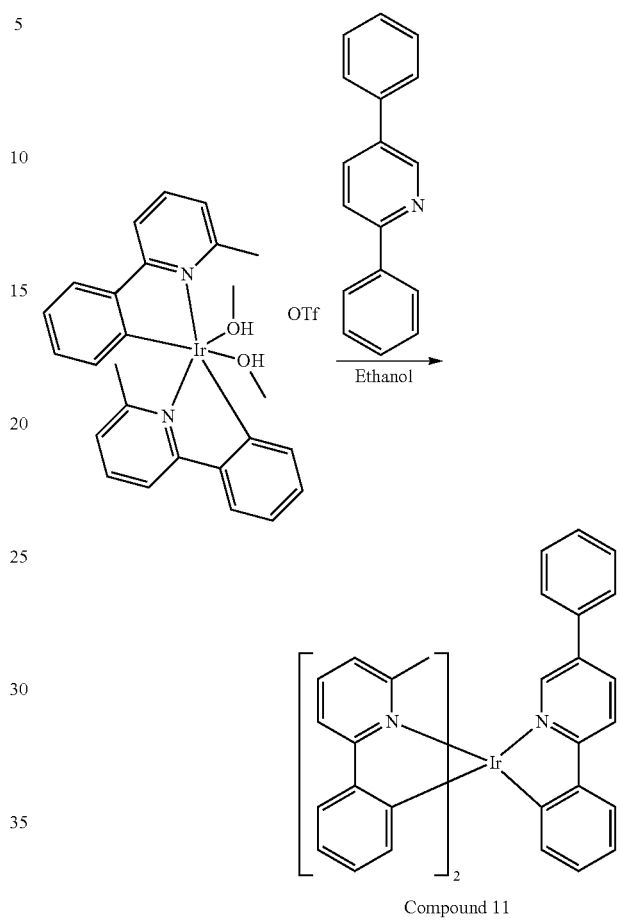

Compound 11

The iridium triflate precursor (1.2 g, 1.6 mmol) and 2,5-diphenylpyridine (1.2 g, 4.8 mmol) were mixed in 50 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.0 g of pure product was obtained after the column purification. (HPLC purity: 99.3%)

The reaction of the iridium triflate intermediate with the second ligand in an organic solvent, as shown for Compound 11, often produces a mixture because of the ligand scrambling during the reaction. Interestingly, during the synthesis of Compound 11, no significant scrambling occurred.

However, the synthesis of Compound 7 using this method resulted in significant scrambling despite the structural similarity between Compounds 11 and 7 (i.e., Compound 7 is identical to Compound 7 except for a methyl group on the phenyl pyridine ligand). In particular, the iridium triflate intermediate was reacted with 2,5-diphenylpyridine in ethanol under reflux condition. The product was a mixture of Compound 7 and other two scrambled products as shown below. Due to the similarity of polarity of the compounds, it is very difficult to separate these impurities from Compound 7 using normal phase silica gel chromatography.

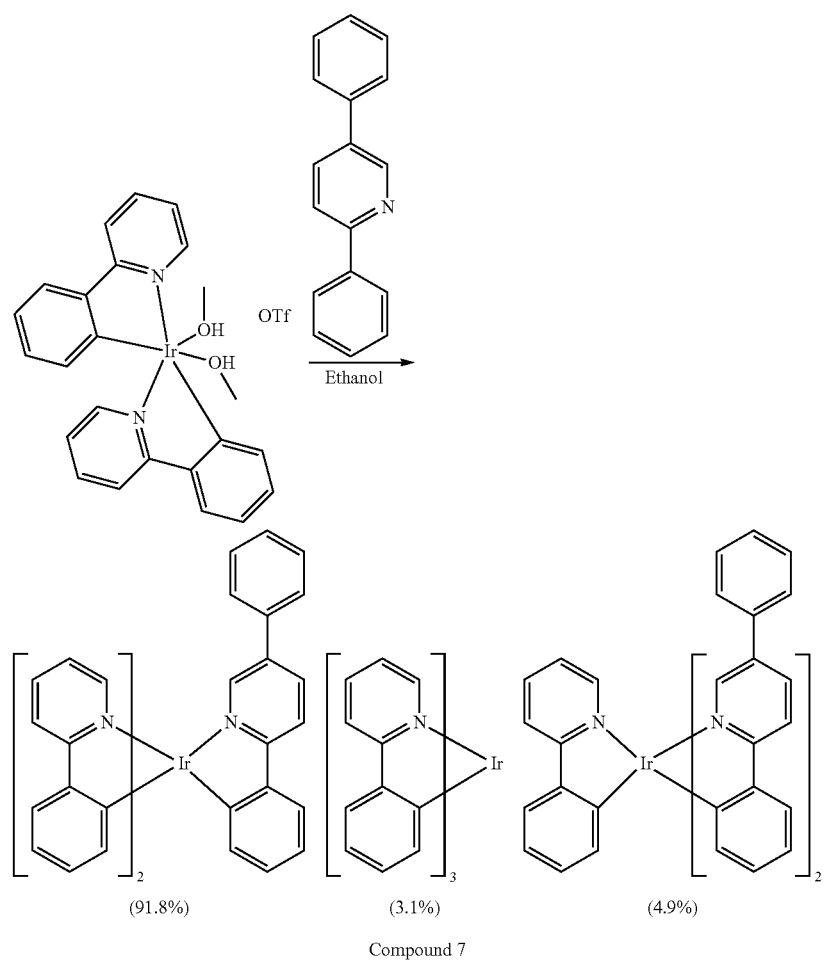

Compound 7

Example 14. Synthesis of Compound 12

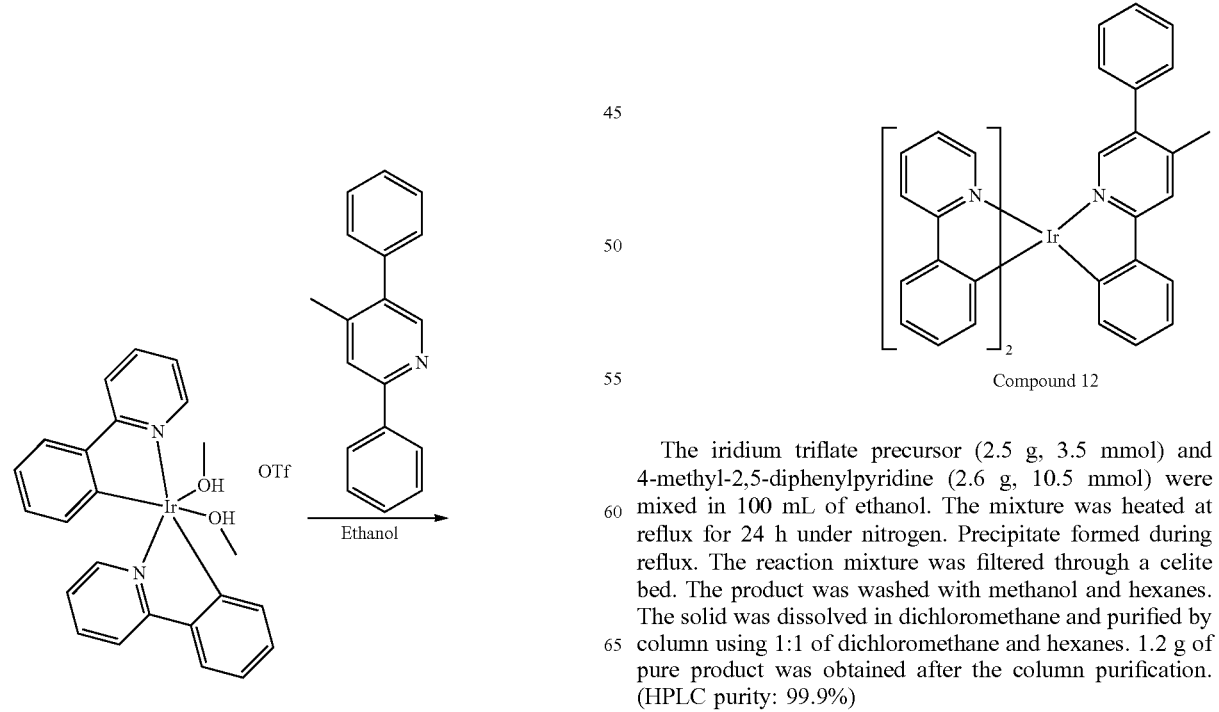

Compound 12

The iridium triflate precursor (2.5 g, 3.5 mmol) and 4-methyl-2,5-diphenylpyridine (2.6 g, 10.5 mmol) were mixed in 100 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 1.2 g of pure product was obtained after the column purification. (HPLC purity: 99.9%)

Example 15. Synthesis of Compound 13

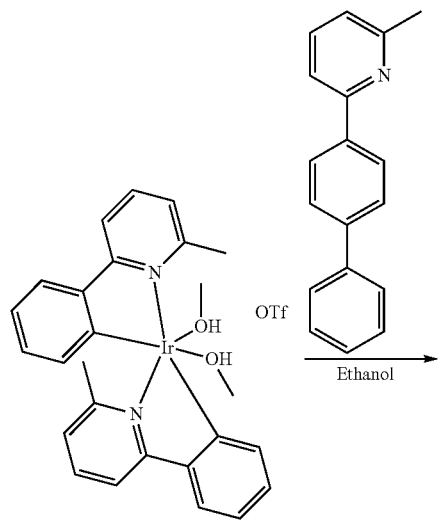

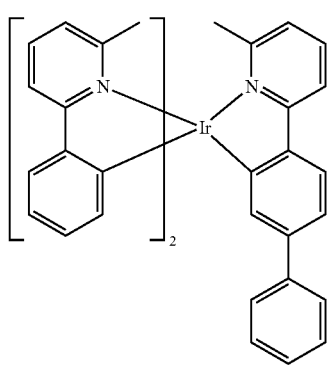

Compound 13

The iridium triflate precursor (2.5 g, 2.7 mmol) and 2-(biphenyl-4-yl)-6-methylpyridine (2.0 g, 8.1 mmol) were put into a 20 mL reaction tube. The reaction tube was evacuated and then refilled with nitrogen. The process was repeated three times. The mixture was heated at 130° C. for 24 h under nitrogen. The reaction mixture was dissolved in dichloromethane and purified by column using 1:1 of dichloromethane and hexanes. 0.98 g of pure product was obtained after the column purification. (HPLC purity: 99.8%)

Example 16. Synthesis of Compound 14

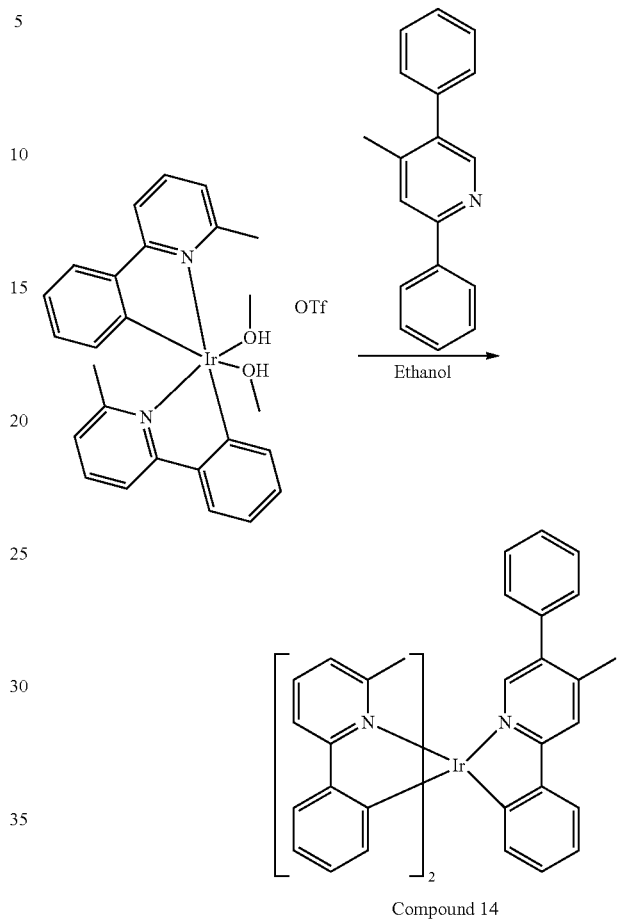

Compound 14

The iridium triflate precursor (0.86 g, 1.15 mmol) and 4-methyl-2,5-diphenylpyridine (0.85 g, 3.46 mmol) were mixed in 30 mL of ethanol. The mixture was heated at reflux for 24 h under nitrogen. Precipitate formed during reflux. The reaction mixture was filtered through a celite bed. The product was washed with methanol and hexanes. The solid was dissolved in dichloromethane and purified by column using 1:1 of dichloromethane and hexanes. 0.7 g of pure product was obtained after the column purification. (HPLC purity: 99.5%)

The reaction of the iridium triflate intermediate with the second ligand in an organic solvent, as shown for Compound 11, often produces a mixture of products because of ligand scrambling during the reaction. Interestingly, during the synthesis of Compounds 10, 11, and 14, no significant scrambling occurred. The content of the desired product in the precipitate was higher than 99% in all cases.

In particular, the synthesis of Compound 7 using this method resulted in significant scrambling despite the structural similarity between Compounds 11 and 7 (i.e., Compound 7 is identical to Compound 7 except for a methyl group on the phenyl pyridine ligand). In particular, the iridium triflate intermediate was reacted with 2,5-diphenylpyridine in ethanol under reflux condition. The product was a mixture of Compound 7 and other two scrambled products as shown below. Due to the similarity of polarity of the compounds, it is very difficult to separate these impurities from Compound 7 using normal phase silica gel chromatography.

Example 17. Synthesis of Compound 21

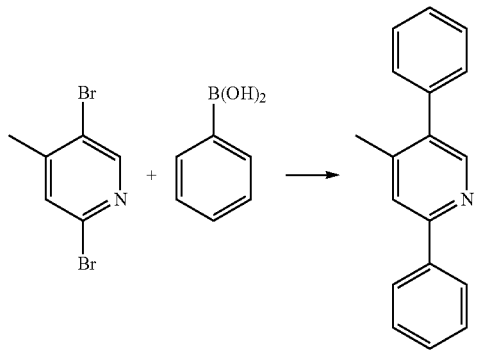

Synthesis of 2,5-diphenyl-4-methylpyridine

Phenylboronic acid (72.9 g, 598 mmol), 2,5-dibromo-4-methypyridine (50 g, 199 mmol), 2-dicyclohexylphosphino-2', 6'-dimethoxybiphenyl (3.3 g, 8 mmol), potassium phosphate tribasic monohydrate (137 g, 595 mmol), 650 mL of toluene and 150 mL of water were placed in a 2 L round-bottom flask. Nitrogen was bubbled directly into the reaction mixture for 30 min after which tris(dibenzylideneacetone) dipalladium(0) (1.79 g, 1.96 mmol) was added. Nitrogen was bubbled into the reaction mixture for another 15 min before the reaction mixture was heated to reflux for 16 h under nitrogen. After the reaction was completed the mixture was cooled and the organic layer was separated from the aqueous layer. The organic layer was washed with a saturated brine solution and then dried over magnesium sulfate. The solution was filtered, and the solvent was removed under vacuum to give a yellow solid as the crude. The crude was purified by column chromatography using silica gel as the stationary phase and 10% ethyl acetate in hexanes as the mobile phase. The product was further purified by recrystallization from hexanes. 42.6 g of desired product was obtained after purification (87.2% yield).

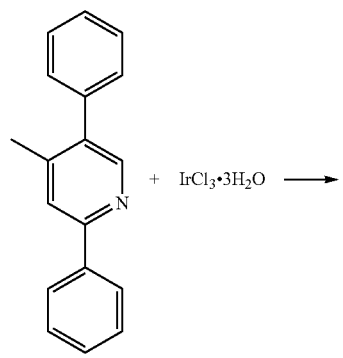

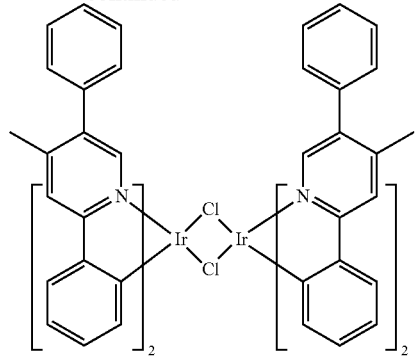

Synthesis of Ir Dimer

IrCl$_3$·3H$_2$O (7.54 g, 20.4 mol) and 2,5-diphenyl-4-methylpyridine (15.0 g, 61 mol) were placed in a 1 L round bottomed flask. 100 mL of 2-ethoxyethanol and 35 mL of water were then added. The mixture was refluxed under nitrogen atmosphere for 16 h. The reaction mixture was cooled to room temperature and the precipitate was filtered and washed with methanol followed by hexanes. 13.6 g of the iridium dimer was obtained (99% yield)

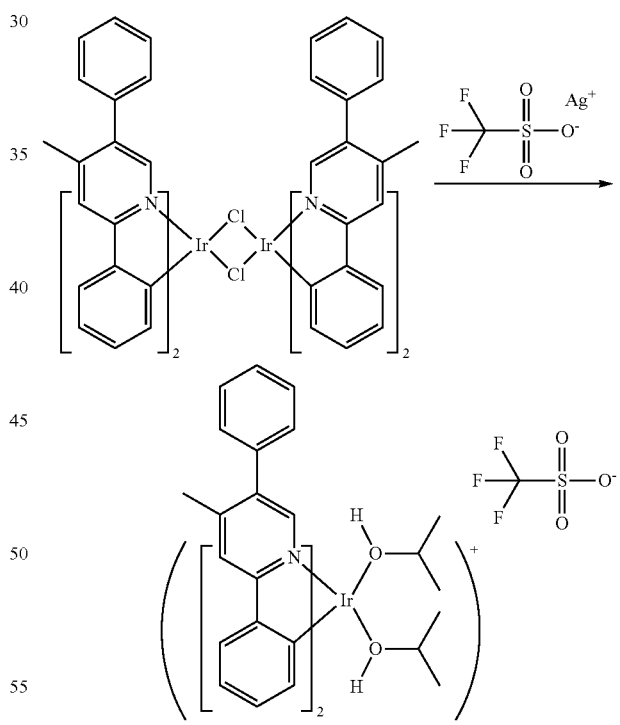

Synthesis of Ir Triflate 13.3 g of the iridium dimer was dissolved in 1.5 L of dichloromethane. Silver triflate (5.11 g, 19.9 mmol) was dissolved in 500 mL of isopropanol and added to the iridium dimer solution. The resulting mixture was stirred for 18 h at room temperature. The solution was then poured through a celite plug to remove silver chloride and the solvent was evaporated under vacuum to give 17.0 g of the iridium triflate. The solid was used for the next step without further purification.

Compound 21

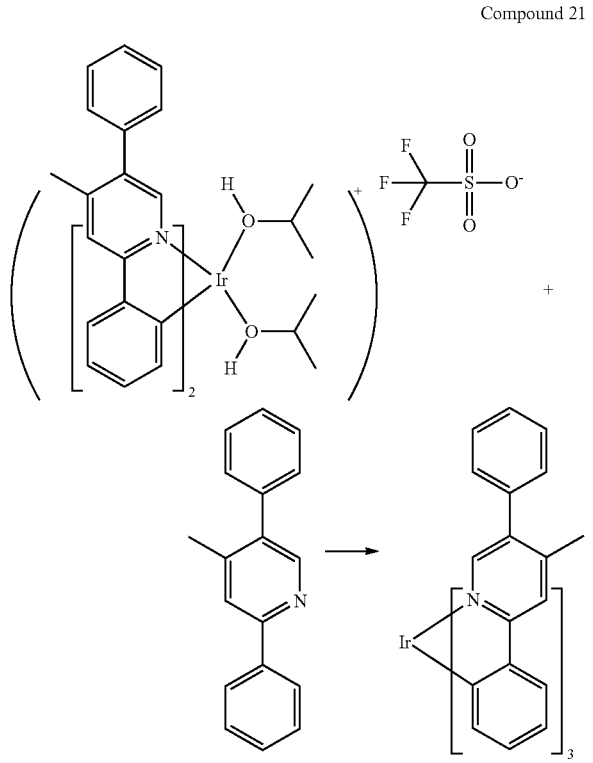

Synthesis of Compound 21

The iridium triflate (17.0 g, 17.9 mmol) and a 3 molar equivalent of 2,5-diphenyl-4-methylpyridine (13.1 g, 53.7 mmol) were placed in a 1 L round bottom flask. 150 mL of ethanol was added and the reaction mixture was refluxed for 16 h. Celite was added to the cooled solution and the mixture was poured onto a 2 inch bed of silica gel. The silica bed was then washed twice with ethanol (2×50 mL), followed by hexanes (2×50 mL). The product was then eluted through a silica gel plug with dichloromethane. Most of the dichloromethane was removed under vacuum and the product was precipitated with 2-propanol and filtered, washed with hexanes and dried to give 9.69 g product (90.6% yield).

Example 18. Synthesis of Compound 22

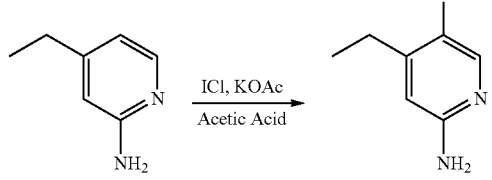

Synthesis of 2-amino-4-ethyl-5-iodopyridine 4-ethyl-2-aminopyridine (10.0 g, 81.9 mmol) and potassium acetate (8.00 g, 81.9 mmol) were dissolved in 100 mL of acetic acid and heated to 80° C. with continuous stirring. In a separate flask, iodomonochloride (13.2 g, 81.9 mmol) was dissolved in 30 mL of acetic acid and added to the above reaction mixture drop wise. Once the addition was completed, the reaction mixture was heated for an additional 4 h. Progress of the reaction was monitored by gas chromatography and HPLC. When the reaction was completed, the reaction mixture was cooled to room temperature and quenched with an aqueous solution of saturated sodium bisulfate (10 mL). Acetic acid was removed under vacuum and the residue was dissolved in ethyl acetate and neutralized with saturated NaHCO$_3$. The organic layer was separated from the aqueous layer and the solvent was removed under vacuum. The crude was purified by silica gel column chromatography eluting with 25% ethyl acetate/hexanes. 15 g of desired product was obtained (74% yield).

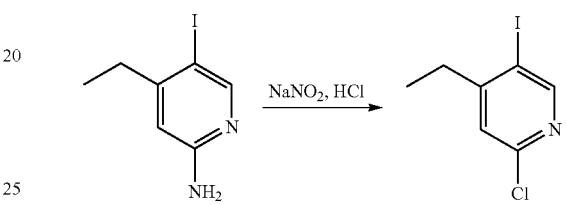

Synthesis of 2-chloro-4-ethyl-5-iodopyridine 4-ethyl-5-iodopyridin-2-amine (15.0 g, 60.48 mmol) was dissolved in 140 mL conc. HCl. NaNO$_2$ was dissolved in 40 mL of water and added drop wise to the above solution at 0° C. Care was taken to prevent the temperature of the reaction mixture from rising above 0° C. When all of the NaNO$_2$ solution was added, the reaction mixture was allowed to warm up to room temperature and was stirred for a further 2 h at room temperature. Progress of the reaction was monitored by GC and HPLC. The reaction mixture was then re-cooled to 0° C. and the pH was adjusted to 01=12 by the addition of sat. NaOH. The mixture was extracted with dichloromethane (2×200 mL) and the solvent removed under vacuum. The crude was purified by silica gel column chromatography eluting with 5% ethyl acetate/hexanes. 8.0 g of desired product was obtained after purification (49% yield).

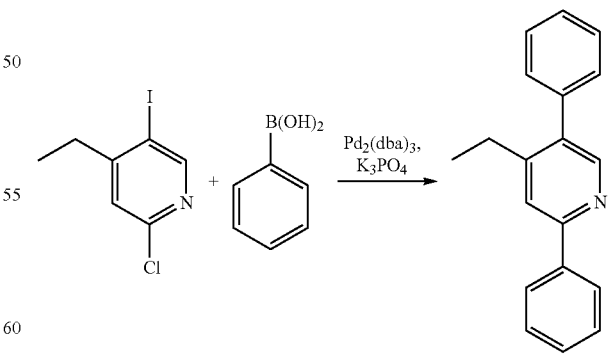

Synthesis of 2,5-diphenyl-4-ethylpyridine

Phenylboronic acid (11.0 g, 90 mmol), 2-chloro-4-ethyl-5-iodopyridine (8.00 g, 30 mmol), 2-dicyclohexylphosphino-2', 6'-dimethoxybiphenyl (492 mg, 1.2 mmol), and potassium phosphate tribasic (20.7 g, 90 mmol), 250 mL of toluene and 25 mL of water were placed in a 1 L round-bottom flask. Nitrogen was bubbled directly into the mixture for 30 min after which tris(dibenzylideneacetone)dipalladium(0) (275 mg, 0.3 mmol) was added. Nitrogen was bubbled for another 15 min, then the reaction mixture was heated to reflux for 16 h under nitrogen. After the reaction was completed the mixture was cooled and the organic layer was separated from the aqueous layer. The organic layer was washed with saturated brine solution and dried over magnesium sulfate. The solution was filtered and the solvent was removed under vacuum to give a off-white solid. This crude was purified by silica gel column chromatography eluting with 10% ethyl acetate/hexanes. 7.0 g of desired product was obtained after purification (90.9% yield).

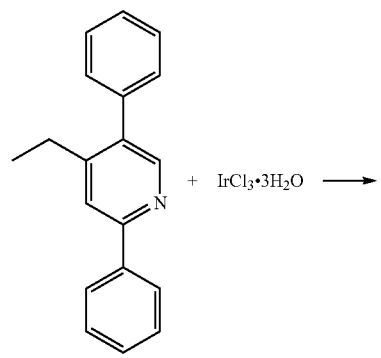

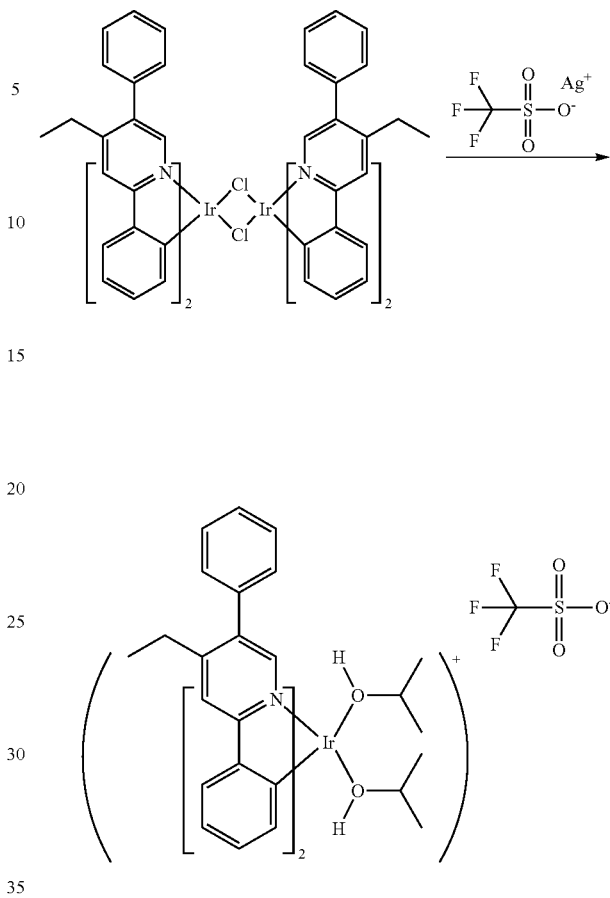

Synthesis of Ir Triflate

The iridium dimer (2.57 g, 1.725 mmol) was dissolved in 250 mL of dichloromethane. Silver triflate (1.0 g, 3.8 mmol) was dissolved in 150 mL of 2-propanol and added to the dimer solution. The resulting mixture was stirred for 5 h. The solution was then poured through a celite plug to remove silver chloride. The solvent was evaporated under vacuum to give 3.2 g of the iridium triflate. The solid was used for next step without further purification.

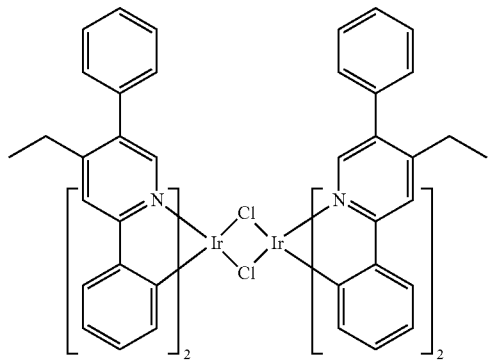

Synthesis of Ir Dimer

IrCl$_3$·3H$_2$O (1.5 g, 4.41 mmol) and 2,5-diphenyl-4-ethyl-pyridine (4.0 g, 15.44 mmol) was placed in a 250 mL round bottomed flask. 30 mL of 2-ethoxyethanol and 10 mL of water was added. The mixture was refluxed under nitrogen atmosphere for 16 h. The reaction mixture was then allowed to cool to room temperature and the precipitate was filtered and washed with methanol followed by hexanes. After drying, 2.57 g of the iridium dimer was obtained (81% yield).

Compound 22

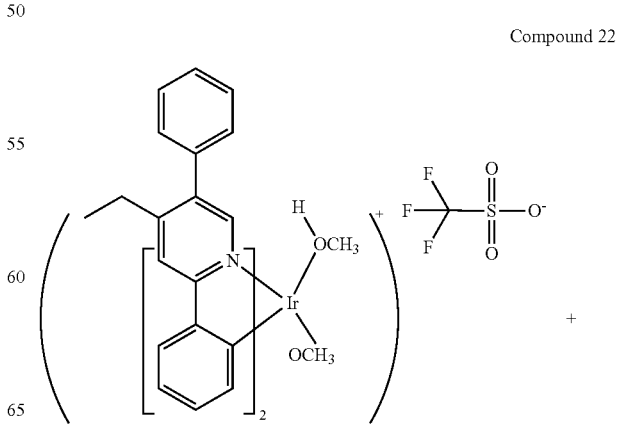

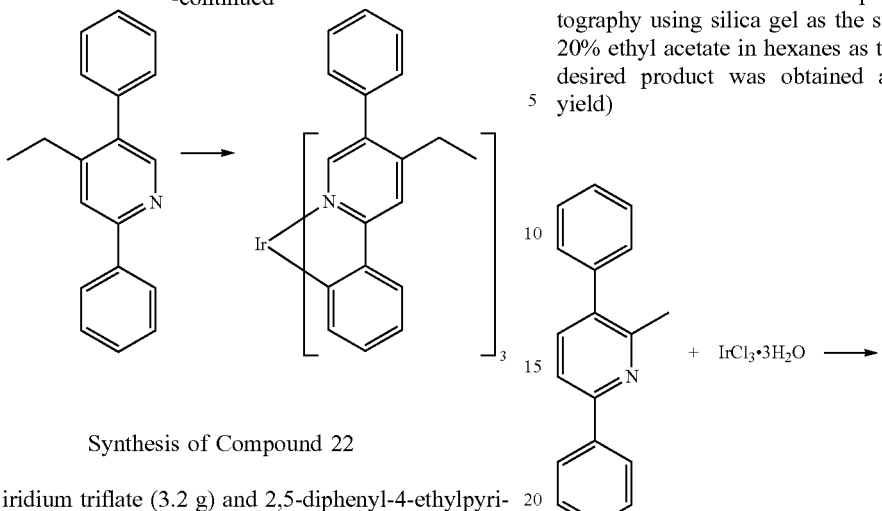

Synthesis of Compound 22

The iridium triflate (3.2 g) and 2,5-diphenyl-4-ethylpyridine (3.2 g) were placed in a 250 mL round bottom flask. 50 mL of ethanol was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. Most of the dichloromethane was removed under vacuum and the product was precipitated with 2-propanol and filtered, washed with hexanes and dried to give 1.67 g of product (52.8% yield).

Example 19. Synthesis of Compound 23

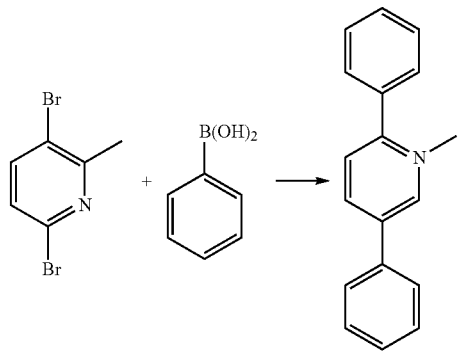

Synthesis of 2,5-diphenyl-6-methylpyridine

Phenylboronic acid (24.3 g, 199.25 mmol), 2,5-dibromo-6-methypyridine (10 g, 39.85 mmol), 2-dicyclohexylphosphino-2', 6'-dimethoxybiphenyl (654 mg, 1.5 mmol), and potassium phosphate tribasic (27.5 g, 119.5 mmol), 300 mL of toluene and 30 mL of water were placed in a 1 L round-bottom flask. Nitrogen was bubbled directly into the mixture for 30 min after which tris(dibenzylideneacetone) dipalladium(0) (364 mg, 0.398 mmol) was added. Nitrogen was bubbled for another 15 min then the reaction mixture was heated to reflux for 16 h under nitrogen. After the reaction was completed, the mixture was cooled and the organic layer was separated. The organic layer was washed with a saturated brine solution and dried over magnesium sulfate. The solution was filtered and the solvent removed under vacuum. The crude was purified by column chromatography using silica gel as the stationary phase and 10%-20% ethyl acetate in hexanes as the mobile phase. 9.0 g of desired product was obtained after purification (92.7% yield)

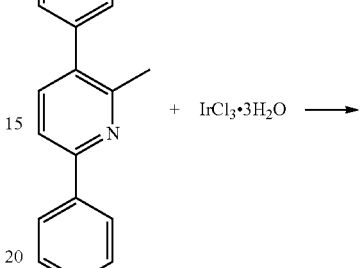

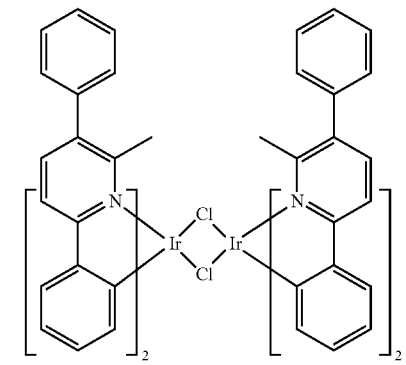

Synthesis of Ir Dimer

IrCl$_3$.3H$_2$O (1.6 g, 4.66 mmol) and 2,5-diphenyl-6-methylpyridine (4.0 g, 16.31 mmol) was placed in a 250 mL round bottomed flask. 45 mL of 2-ethoxyethanol and 15 mL of water were added. The mixture was refluxed under nitrogen for 16 h. The reaction mixture was then allowed to cool to room temperature. The precipitate was filtered and washed with methanol followed by hexanes. After drying, 2.75 g of dimer was obtained (84.6% yield).

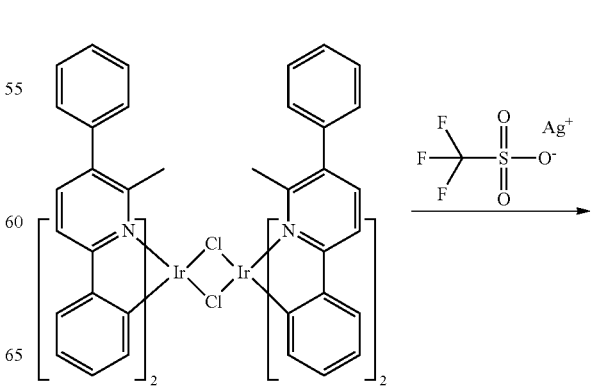

Synthesis of Ir Triflate

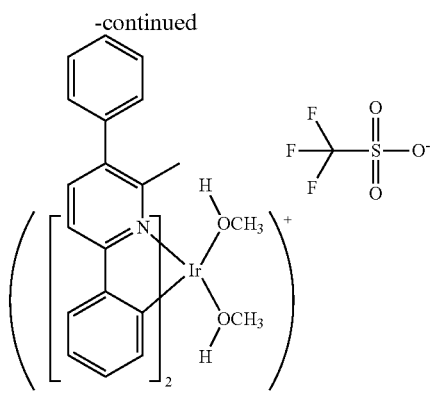

The iridium dimer (2.75 g, 2.2 mmol) was dissolved in 200 mL of dichloromethane. Silver triflate (1.19 g, 4.6 mmol) was dissolved in 100 mL of methanol and added to the iridium dimer solution. The resulting mixture was stirred for 5 h. The solution was then passed through a celite plug to remove silver chloride. The solvent was evaporated under vacuum to give 3.5 g of the iridium triflate. The solid was used for next step without further purification.

Compound 23

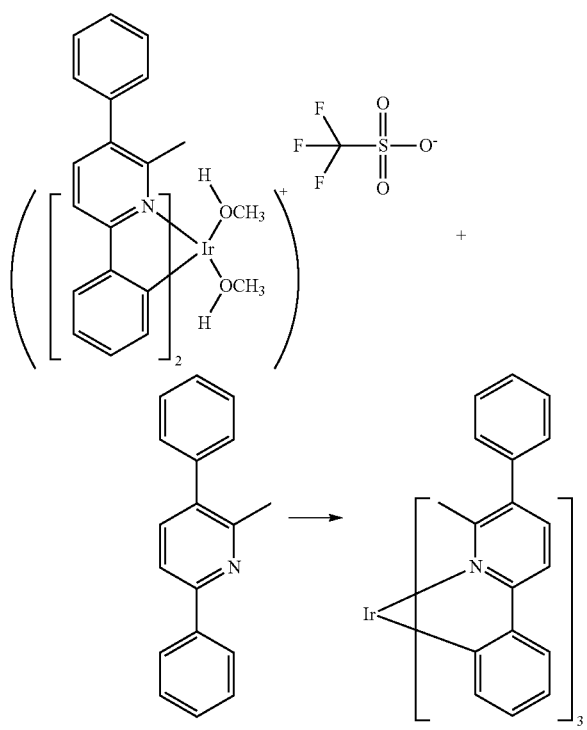

Synthesis of Compound 23

The iridium triflate (3.0 g) and 2,5-diphenyl-6-methylpyridine (3.0 g) was placed in a 100 mL round bottom flask. The solid mixture was heated to 130° C. for 16 h. After cooling the reaction mixture was dissolved in 200 mL of dichloromethane. The solution was then passed through a 2 inch silica gel plug. The solvent was removed under vacuum and the residue was chromatographed using silica gel with dichloromethane as the mobile phase. Most of the solvent was evaporated and the product was precipitated with 2-propanol and filtered, washed with hexanes and then dried to give 2.65 g of product (71% yield).

Example 20. Synthesis of Compound 24

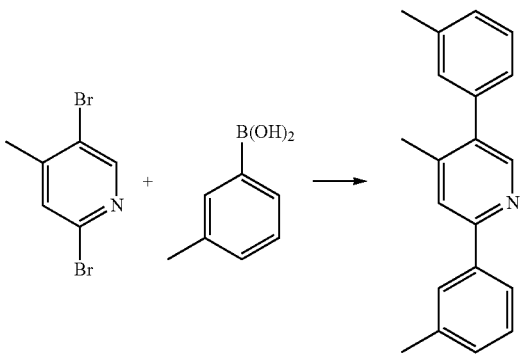

Synthesis of 2,5-(m-tolyl)-4-methylpyridine m-tolylboronic ester (17.9 g, 132 mmol), 2,5-dibromo-4-methypyridine (11.0 g, 44.0 mmol), 2-dicyclohexylphosphino-2', 6'-dimethoxybiphenyl (726 mg, 1.77 mmol), and potassium phosphate tribasic monohydrate (30 g, 130 mmol), 143 mL of toluene and 33 mL of water were placed in a 500 mL round-bottom flask. Nitrogen was bubbled directly into the mixture for 30 min after which tris(dibenzylideneacetone)dipalladium(0) (394 mg, 43 mmol) was added. Nitrogen was bubbled for another 15 min then the reaction mixture was heated to reflux for 16 h under nitrogen. The mixture was allowed to cool to room temperature and the organic layer was separated from the aqueous layer. The organic layer was washed with a saturated brine solution and dried over magnesium sulfate. The solution was filtered and the solvent removed under vacuum to give an off white product. The crude was purified by column chromatography using silica gel as the stationary phase and 10% ethyl acetate in hexanes as the mobile phase. 11.2 g of desired product was obtained after purification. (93.3% yield)

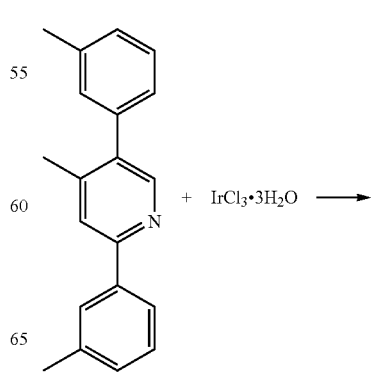

-continued

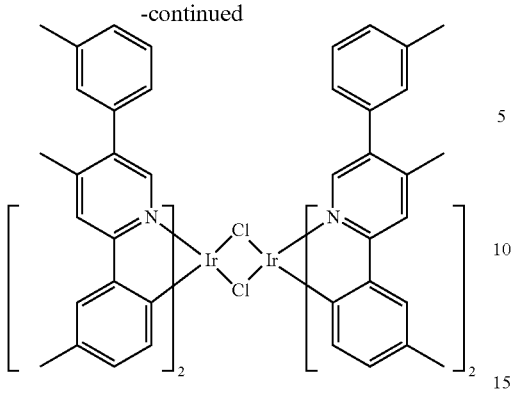

Synthesis of Ir Dimer

IrCl$_3$·3H$_2$O (1.8 g, 4.86 mmol) and 2,5-ditolyl-4-methyl-pyridine (4.0 g, 14.6 mmol) was placed in a 100 mL round bottomed flask. 24 mL of 2-ethoxyethanol and 8 mL of water were added. The mixture was refluxed under nitrogen atmosphere for 16 h. The reaction mixture was then allowed to cool to room temperature. The precipitate was filtered and washed with methanol followed by hexanes. After drying, 3.0 g of the iridium dimer was obtained (79.6% yield).

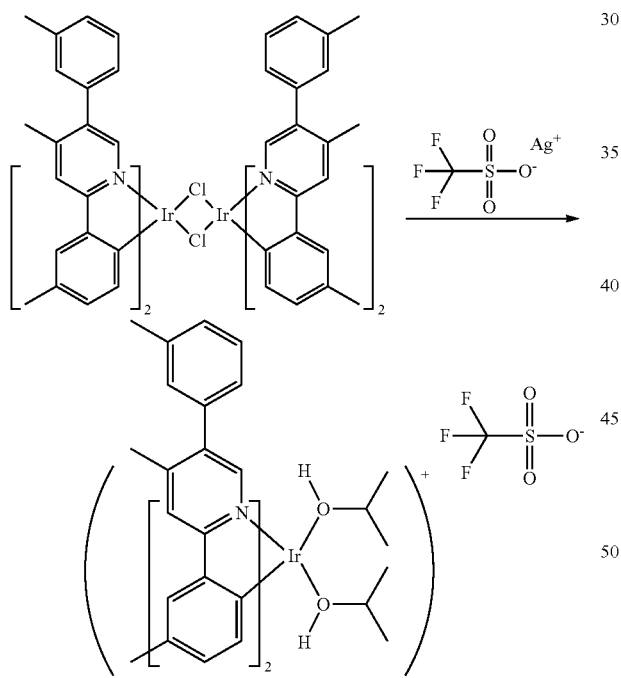

Synthesis of Ir Triflate 3.0 g of the iridium dimer was dissolved in 380 mL of dichloromethane. Silver triflate (1.0 g, 4.08 mmol) was dissolved in 20 mL of isopropanol and added to the iridium dimer solution. The resulting mixture was stirred for 5 h. The solution was then poured through a celite plug to remove silver chloride. The solvent was evaporated under vacuum to give 2.7 g of the iridium triflate. The solid was used for next step without further purification.

Compound 24

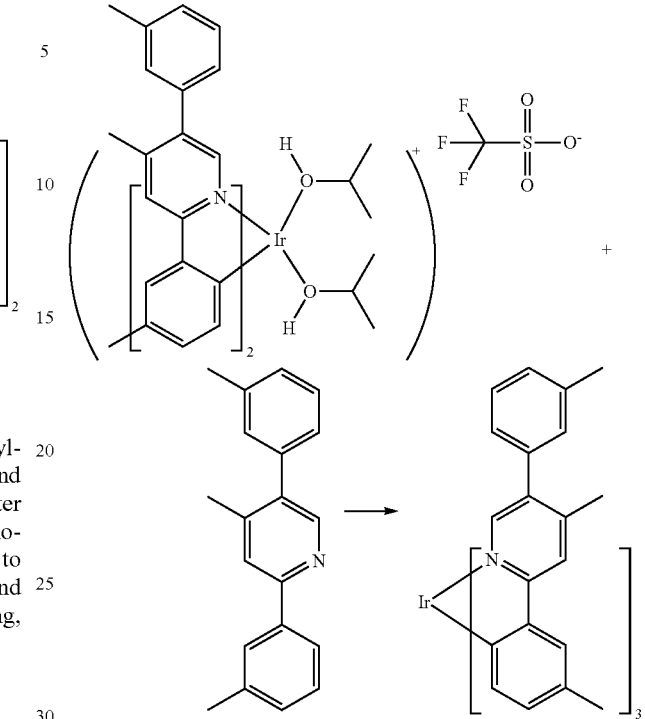

Synthesis of Compound 24

The iridium triflate (2.7 g, 2.95 mmol) and (3.6 g, 112 mmol) of 2,5-ditolyl-4-methylpyridine was placed in a 250 mL round bottom flask. 100 mL of ethanol was added and the mixture was refluxed for 16 h. Celite was added to the cooled solution and the mixture was poured onto a 2 inch bed of silica gel. The silica bed was then washed twice with ethanol (2×50 mL), followed by hexanes (2×50 mL). The product was then eluted through the silica plug with dichloromethane. Most of the dichloromethane was removed under vacuum and the product was precipitated with 2-propanol and filtered, washed with hexanes and dried to give 2.4 g of product (80.6% yield).

Example 21. Synthesis of Compound 25

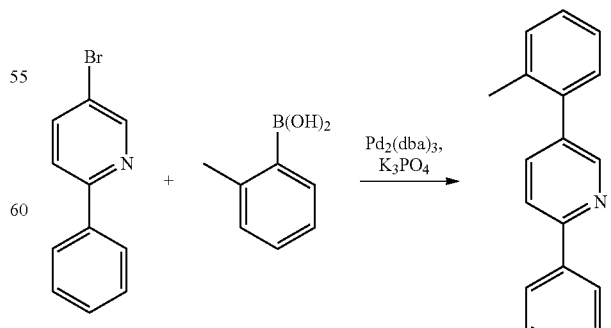

Synthesis of 2-phenyl-5-(m-tolyl)pyridine 2-methylphenyl boronic acid (5.1 g, 37.59 mmol), 2-phenyl-5-bromopyridine (8.0 g, 34.17 mmol), 2-dicyclohexylphosphino-2', 6'-dimethoxybiphenyl (561 mg, 1.366 mmol), and potassium phosphate tribasic (23.50 g, 102.51 mmol), 250 mL of toluene and 25 mL of water were placed in a 1 L round-bottom flask. Nitrogen was bubbled directly into the mixture for 30 min after which tris(dibenzylideneacetone)dipalladium(0) (312 mg, 0.341 mmol) was added. Nitrogen was then bubbled for another 15 minutes and the reaction mixture was heated to reflux for 16 h under nitrogen. The mixture was cooled and the organic layer was separated from the aqueous layer. The organic layer was washed with saturated brine solution, dried over magnesium sulfate, filtered, and the solvent removed under vacuum to give an off-white solid as the crude. The crude was purified by column chromatography using silica gel as the stationary phase and 2% ethyl acetate in hexanes as the mobile phase. 6.5 g of desired product was obtained after purification (78% yield).

Example 22. Synthesis of Compound 26

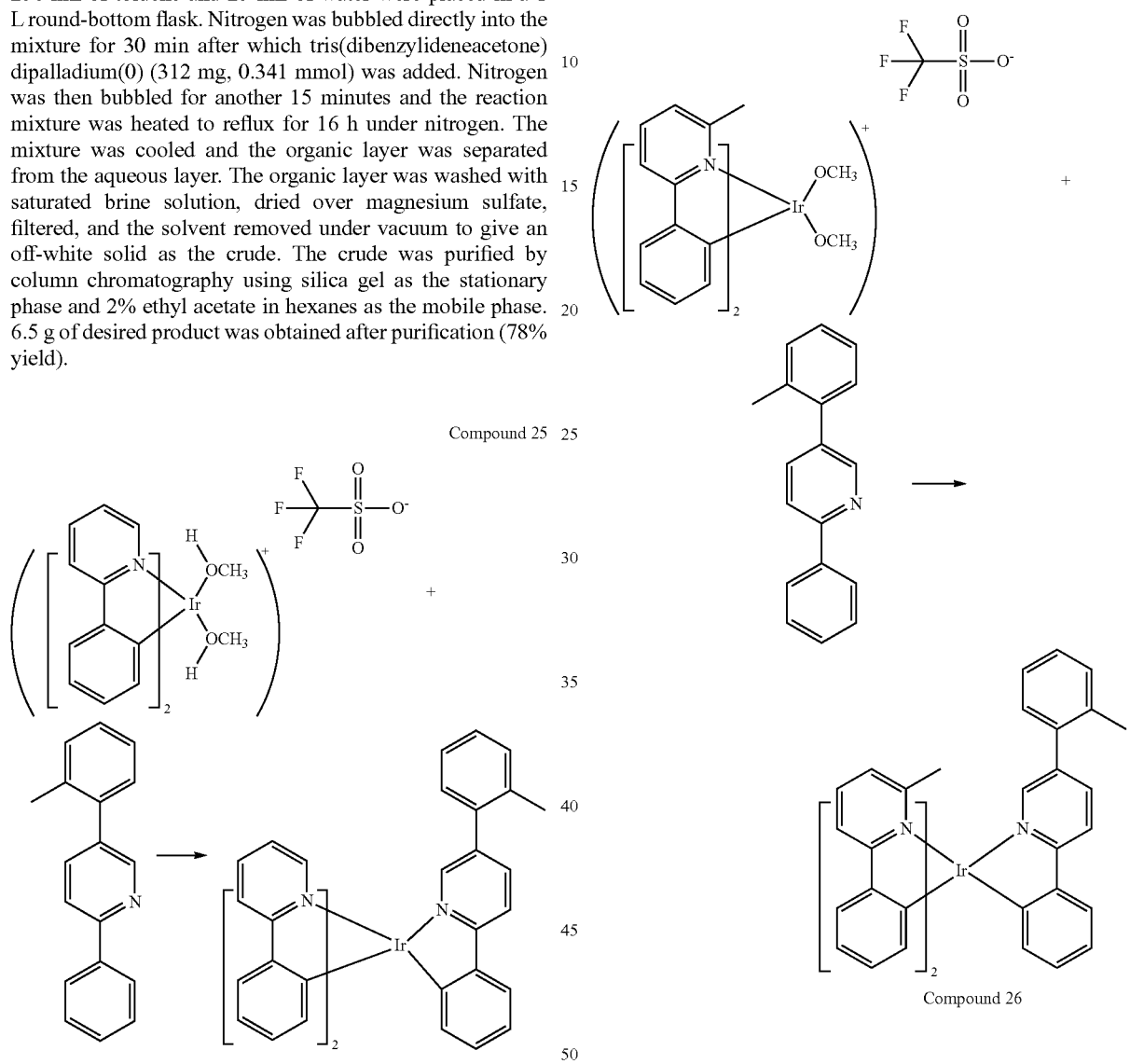

Compound 25

Compound 26

Synthesis of Compound 25

The iridium triflate (from the synthesis of compound 1) (3.25 g) and 2-phenyl-5-tolylpyridine (3.2 g) were placed in a 250 mL round bottom flask. A 50:50 mixture of methanol and ethanol (100 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 0.53 g of desired product was obtained after purification (15.6% yield).

Synthesis of Compound 26

The iridium triflate (3.25 g) and 2-phenyl-5-tolylpyridine (3.2 g) were placed in a 250 mL round bottom flask. A 50:50 mixture of methanol and ethanol (100 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as the desired compound. The compound was further purified by column chromatography using silica gel as the stationary phase and 1:1 dichloromethane/hexanes as the mobile phase. 3.38 g of desired product was obtained after purification (100% yield).

Example 23. Synthesis of Compound 27

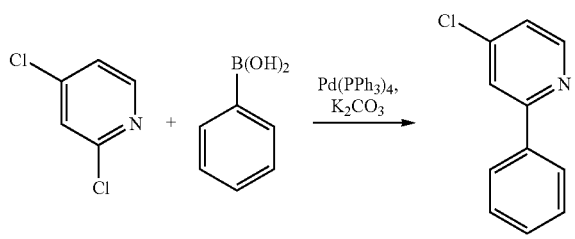 [SMILES: Clc1ccnc(Cl)c1 ; OB(O)c1ccccc1 ; Clc1ccnc(-c2ccccc2)c1]

Synthesis of 2-phenyl-4-chloropyridine 2,4-dichloropyridine (10 g, 67.57 mmol), phenylboronic acid (9.0 g, 74.32 mmol), and potassium carbonate (28 g, 202.70 mmol), 300 mL dimethoxyethane and 30 mL of water was placed in a 1 L round-bottom flask. Nitrogen was bubbled directly into the mixture for 30 min. Tetrakis(triphenylphosphine)palladium(0) (780 mg, 0.675 mmol) was added and nitrogen was bubbled into the reaction mixture for a another 15 min. The reaction mixture was then heated to reflux under nitrogen for 16 h. The reaction was then allowed to cool to room temperature and diluted with ethyl acetate and water. The organic and aqueous layers were separated and the aqueous layer was extracted with ethyl acetate. The organic layers were combined and washed with a saturated brine solution. The organic layer was then dried over magnesium sulfate, filtered, and the solvent was removed under vacuum to give an off-white solid as crude. The crude was purified by column chromatography using silica gel as the stationary phase and 2% ethyl acetate in hexanes as the mobile phase. 8.0 g of desired product was obtained after purification (54% yield). 11.5 g of desired product was obtained after purification (89.77% yield).

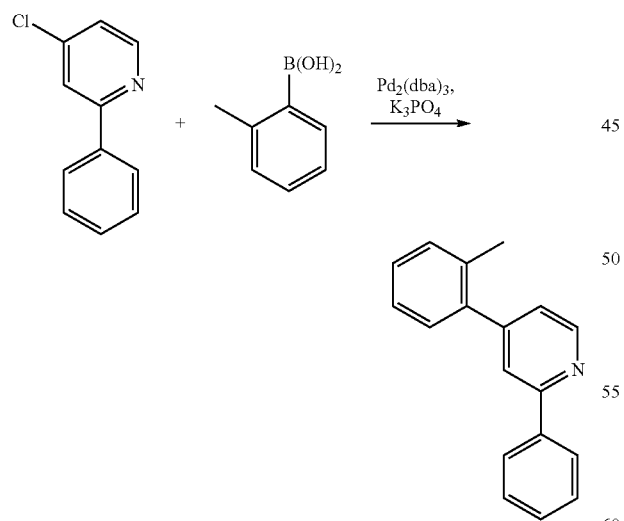

Synthesis of 2-phenyl-4-(m-tolyl)pyridine 2-methylphenyl boronic acid (6.3 g, 46.40 mmol), 2-phenyl-4-chloropyridine (8.0 g, 42.18 mmol), 2-dicyclohexylphosphino-2', 6'-dimethoxybiphenyl (692 mg, 1.68 mmol), and potassium phosphate tribasic (29.10 g, 126.54 mmol) 250 mL of toluene and 25 mL of water were placed in a 500 mL round-bottom flask. Nitrogen was bubbled directly into the mixture for 30 min after which tris(dibenzylideneacetone)dipalladium(0) (386 mg, 0.421 mmol) was added. Nitrogen was then bubbled for another 15 minutes then the reaction mixture was heated to reflux for 16 h under nitrogen. The mixture was cooled and the organic layer was separated from the aqueous layer. The organic layer was washed with a saturated brine solution, dried over magnesium sulfate, filtered, and the solvent removed under vacuum to give an off-white solid as the crude. The crude was purified by column chromatography using silica gel as the stationary phase and 2% ethyl acetate in hexanes as the mobile phase. 8.0 g of desired product was obtained after purification (77.4% yield).

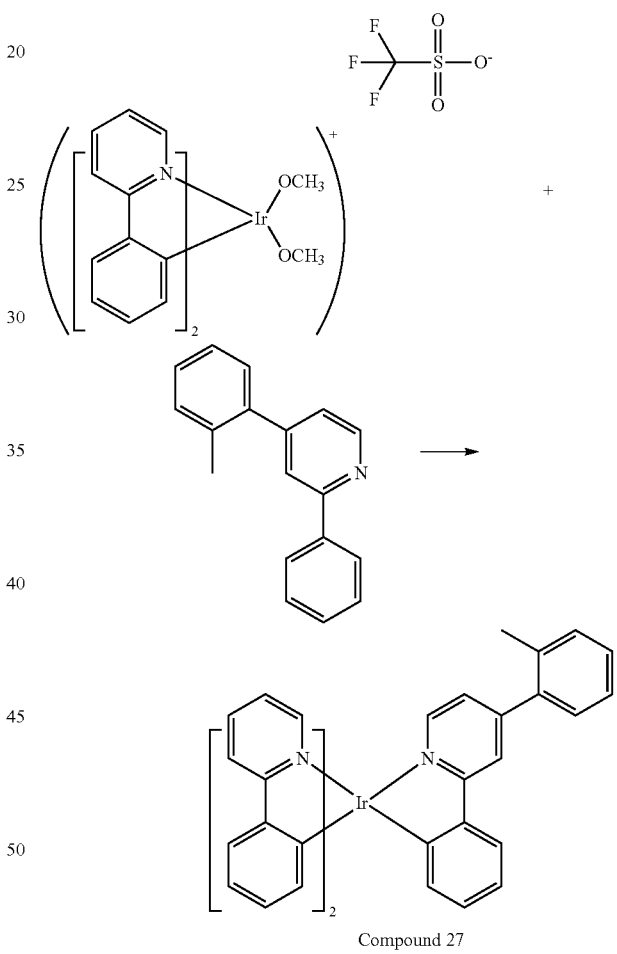

Compound 27

Synthesis of Compound 27

The iridium triflate (4.0 g) and 2-phenyl-4-o-tolylpyridine (4.0 g) were placed in a 250 mL round bottom flask. A 50:50 mixture of methanol and ethanol (100 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 2.0 g of desired product was obtained after purification (48% yield).

Example 24. Synthesis of Compound 28

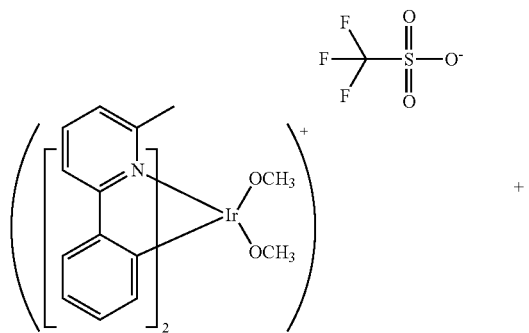

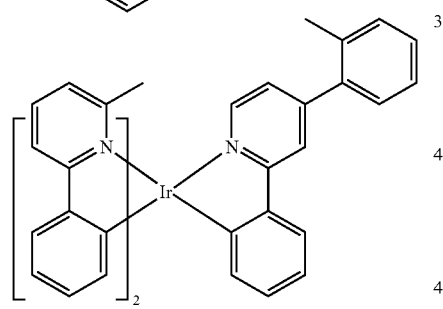

Compound 28

Synthesis of Compound 28

The iridium triflate (4.0 g) and 2-phenyl-4-o-tolylpyridine (4.0 g) was placed in a 250 mL round bottom flask. A 50:50 mixture of methanol and ethanol (100 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as the desired compound. The compound was further purified by column chromatography using silica gel as the stationary phase and 1:1 dichloromethane/hexanes as the mobile phase. 3.6 g of desired product was obtained after purification (86.6% yield).

Example 25. Synthesis of Compound 29

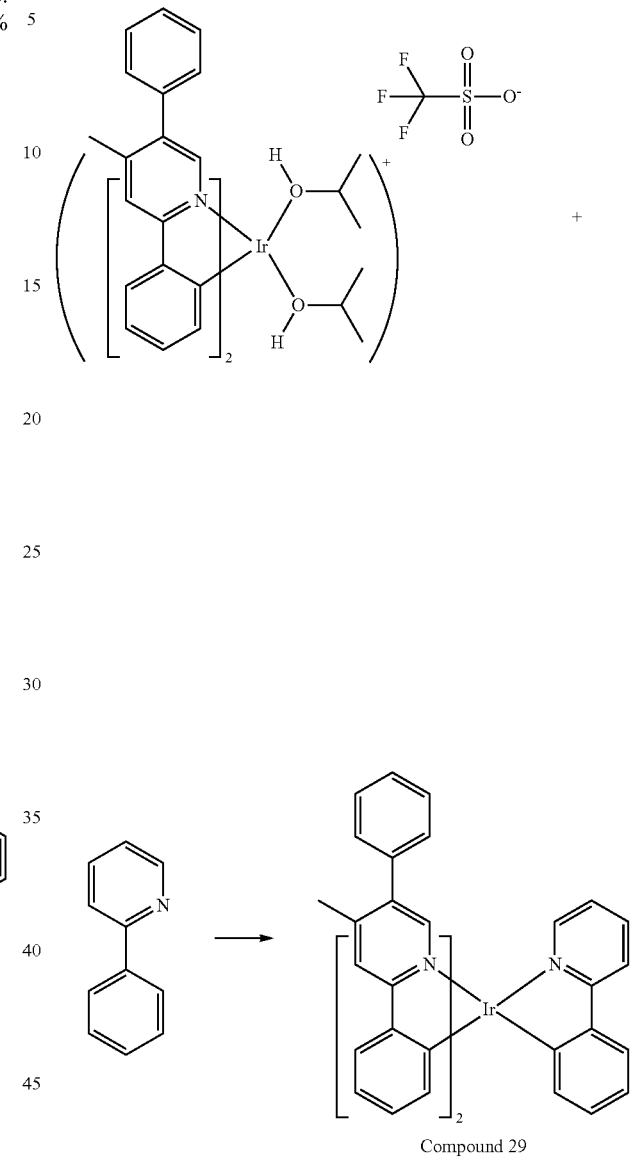

Compound 29

Synthesis of Compound 29

The iridium triflate (4.0 g, 4.62 mmol) and (2.15 g, 13.87 mmol) of 2-phenylpyridine were placed in a 100 mL round-bottom flask. A 50:50 mixture of methanol and ethanol (60 mL) was added and the mixture was refluxed for 16 h. Celite was added to the cooled solution and the mixture was poured onto a 2 inch bed of silica gel. The silica bed was then washed twice with ethanol (2×50 mL), followed by hexanes (2×50 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 1.1 g of desired product was obtained after purification (31.6% yield).

153
Example 26. Synthesis of Compound 30

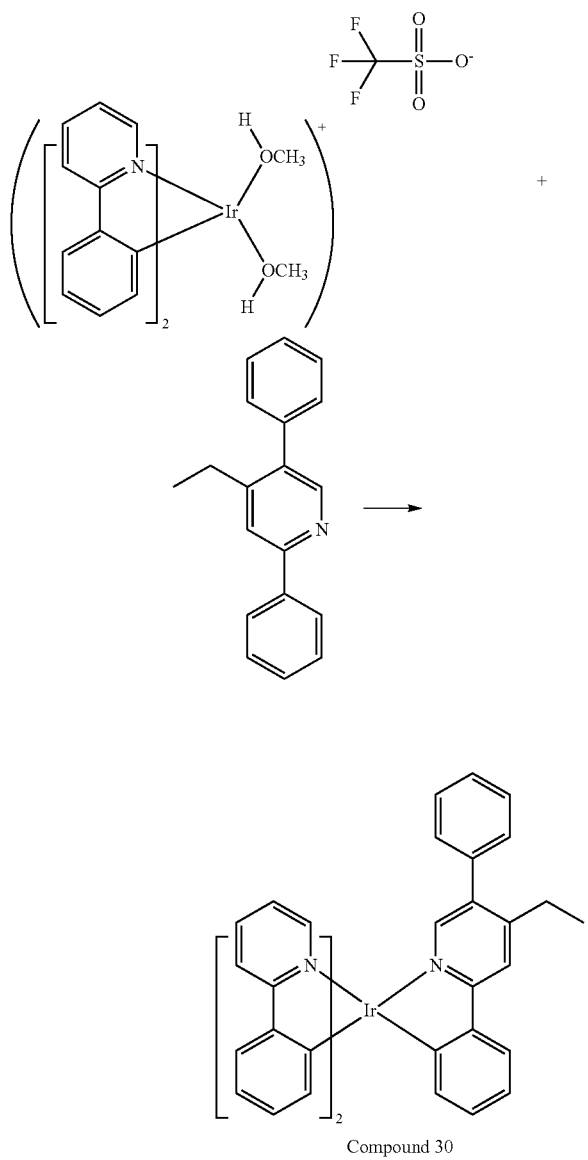

Compound 30

Synthesis of Compound 30

The iridium triflate (3.2 g) and 2,5-diphenyl-4-ethylpyridine (3.2 g) was placed in a 250 mL round bottom flask. 50 mL of ethanol was added and the mixture was refluxed for 16 h. Celite was added to the cooled solution and the mixture was poured onto a 2 inch bed of silica gel. The silica bed was then washed twice with ethanol (2×50 mL), followed by hexanes (2×50 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 1.22 g of desired product was obtained after purification (31.6% yield).

154
Example 27. Synthesis of Compound 31

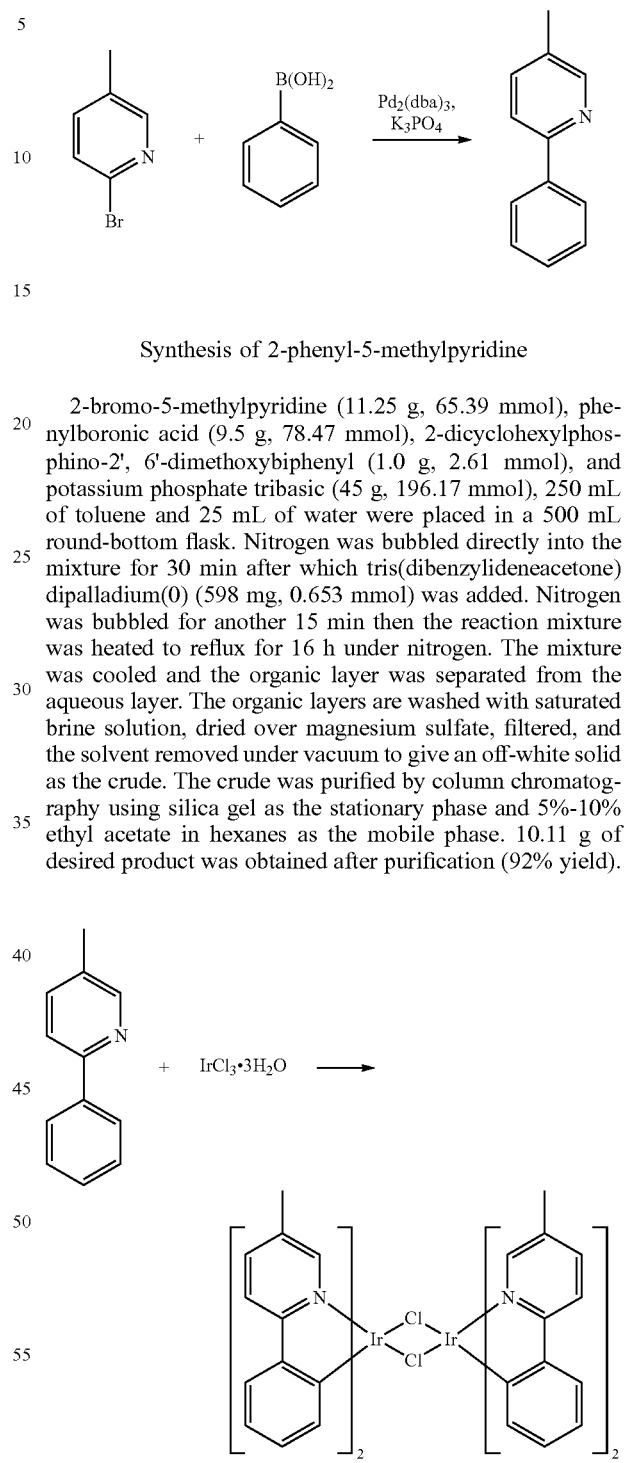

Synthesis of 2-phenyl-5-methylpyridine 2-bromo-5-methylpyridine (11.25 g, 65.39 mmol), phenylboronic acid (9.5 g, 78.47 mmol), 2-dicyclohexylphosphino-2', 6'-dimethoxybiphenyl (1.0 g, 2.61 mmol), and potassium phosphate tribasic (45 g, 196.17 mmol), 250 mL of toluene and 25 mL of water were placed in a 500 mL round-bottom flask. Nitrogen was bubbled directly into the mixture for 30 min after which tris(dibenzylideneacetone) dipalladium(0) (598 mg, 0.653 mmol) was added. Nitrogen was bubbled for another 15 min then the reaction mixture was heated to reflux for 16 h under nitrogen. The mixture was cooled and the organic layer was separated from the aqueous layer. The organic layers are washed with saturated brine solution, dried over magnesium sulfate, filtered, and the solvent removed under vacuum to give an off-white solid as the crude. The crude was purified by column chromatography using silica gel as the stationary phase and 5%-10% ethyl acetate in hexanes as the mobile phase. 10.11 g of desired product was obtained after purification (92% yield).

Synthesis of Ir Dimer 2-phenyl-5-methylpyridine (10.11 g, 59.8 mmol) and $IrCl_3 \cdot 3H_2O$ (6.0 g, 17 mmol) were dissolved in 90 mL of 2-ethoxyethanol and 30 mL of water in a 250 mL round-bottom flask. The reaction mixture was refluxed under nitrogen for 16 h. The reaction mixture was then allowed to cool to room temperature and the precipitate was filtered and washed with methanol followed by hexanes. The iridium dimer was then dried under vacuum and used for the next step without further purification. 8.75 g of the dimer was obtained after vacuum drying (91.0% yield).

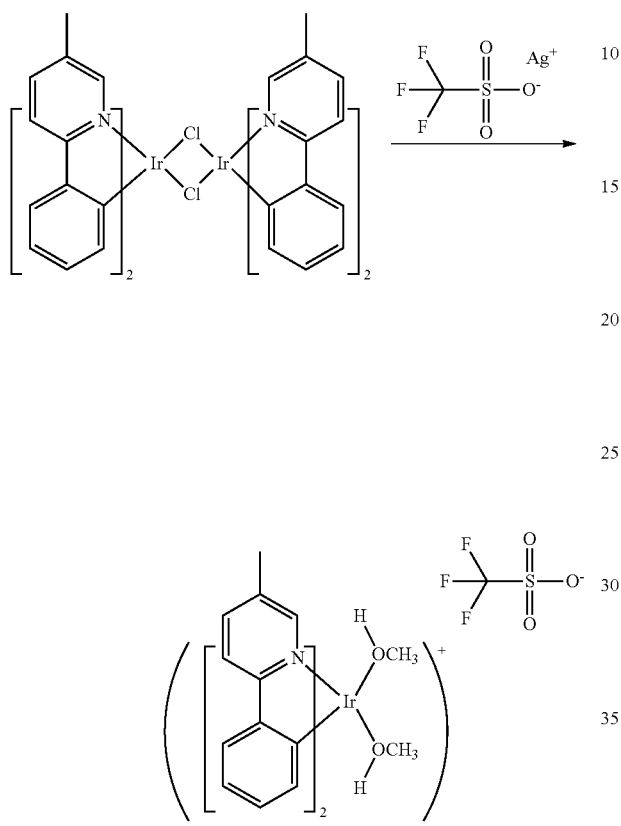

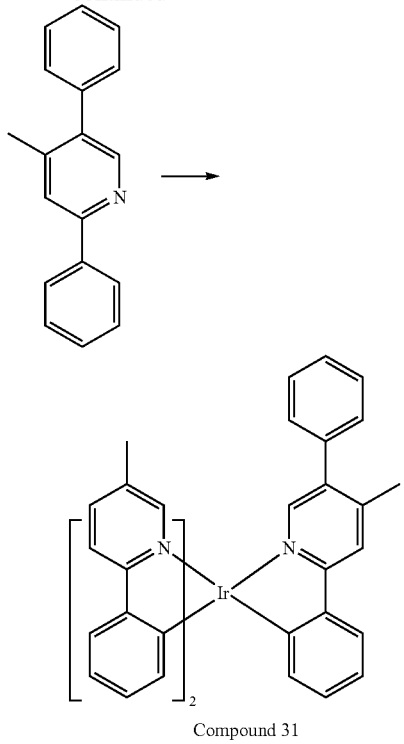

Compound 31

Synthesis of Compound 31

The iridium triflate (4.0 g) and 2,5-diphenyl-4-methyl-pyridine (4.0 g) were placed in a 250 mL round bottom flask. A 50:50 mixture of methanol and ethanol (80 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 3.75 g of desired product was obtained after purification (90% yield).

Example 28. Synthesis of Compound 32

Synthesis of Ir Triflate

The iridium dimer (8.74 g, 7.75 mmol) was dissolved in 1.0 L of dichloromethane. Silver triflate (4.18 g, 16.27 mmol) was dissolved in 500 mL of methanol and added to the iridium dimer solution. The resulting mixture was stirred for 18 h. The solution was then passed through a celite plug to remove silver chloride and the solvent was evaporated to give 4.0 g of iridium triflate. The solid was used for next step without further purification.

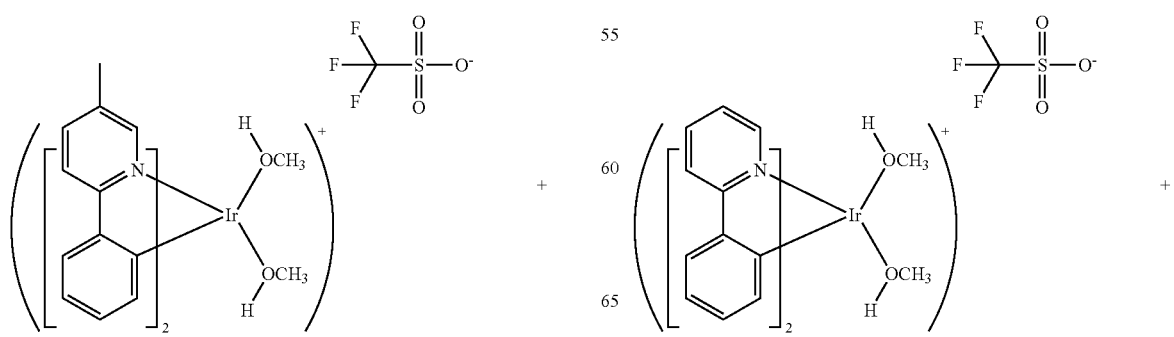

-continued

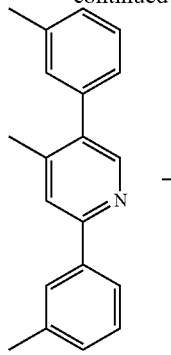

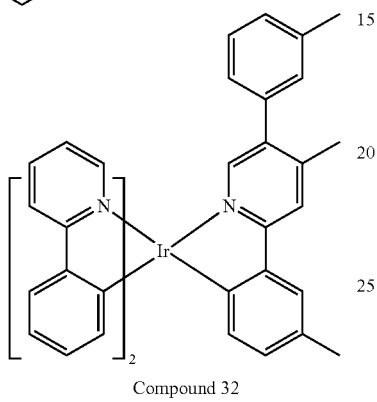

Compound 32

Synthesis of Compound 32

The iridium triflate (2.6 g, 3.66 mmol) and 2,5-ditolyl-4-methylpyridine (3.0 g, 11 mmol) were placed in a 100 mL round bottom flask. A 50:50 mixture of methanol and ethanol (50 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 0.9 g of desired product was obtained after purification (31.8% yield).

Example 29. Synthesis of Compound 33

-continued

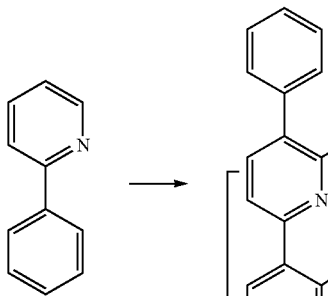

Compound 33

Synthesis of Compound 33

The iridium triflate (2.8 g) and 2-phenylpyridine (2.8 g) were placed in a 250 mL round bottom flask. A 50:50 mixture of methanol and ethanol (80 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as the desired compound. The compound was further purified by column chromatography using silica gel as the stationary phase and 1:1 dichloromethane/hexanes as the mobile phase. 2.3 g of desired product was obtained after purification (73.2% yield).

Example 30. Synthesis of Compound 34

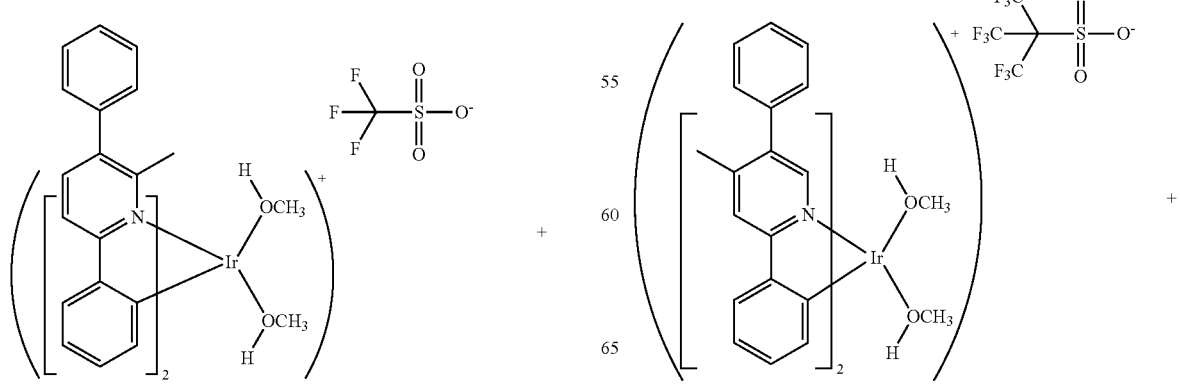

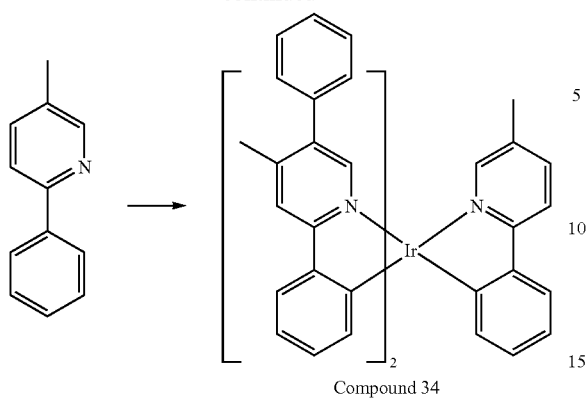

Compound 34

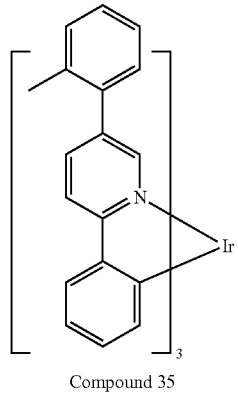

Compound 35

Synthesis of Compound 34

The iridium triflate (3.5 g) and 2-phenyl-5-methylpyridine (3.5 g) were placed in a 250 mL round bottom flask. A 50:50 mixture of methanol and ethanol (80 mL) was added and the mixture was refluxed for 16 h. Celite was added to the cooled solution and the mixture was poured onto a 2 inch bed of silica gel. The silica bed was then washed twice with ethanol (2×100 mL), followed by hexanes (2×100 mL). The product was then eluted through the silica plug with dichloromethane. The dichloromethane was removed under vacuum to give the crude product as a mixture of compounds. The desired compound was separated and isolated by column chromatography using silica gel as the stationary phase and 1:1 dichloromethane/hexanes as the mobile phase. 1.25 g of desired product was obtained after purification (31.4% yield).

Synthesis of Compound 35

2-phenyl-5-o-tolylpyridine (8.8 g, 35.9 mmol, 6 eq) and Iridium tris acetylacetonate (2.93 g, 5.98 mmol, 1 eq) were placed in a 50 mL round-bottom flask. The flask was purged with nitrogen for 0.5 h. The reaction mixture was then heated to 230° C. in a sand bath for 48 h. The reaction mixture was allowed to cool to room temperature and 100 mL of dichloromethane was added. The mixtures was filtered through a silica gel plug. The solvent was removed under vacuum to give the crude product. The crude was purified by column chromatography using silica gel as the stationary phase and 1:1 dichloromethane/hexanes as the mobile phase. 0.4 g of desired product was obtained after purification (7.2% yield).

Example 32. Synthesis of Compound 36

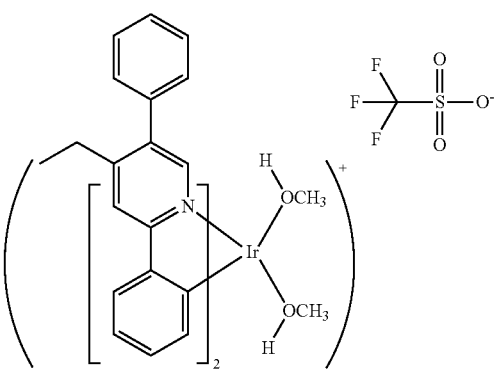

Example 31. Synthesis of Compound 35

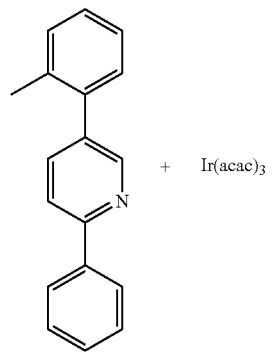

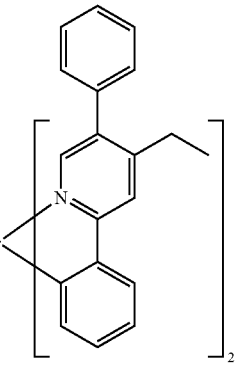

Compound 36

Synthesis of Compound 36

The iridium triflate and 3 molar equivalent of 2-phenylpyridine can be dissolved in a 50:50 mixture of methanol and ethanol and the mixture refluxed for 16 h. The mixture can be purified using a method similar to that described in Example 30.

Example 33. Synthesis of Compound 37

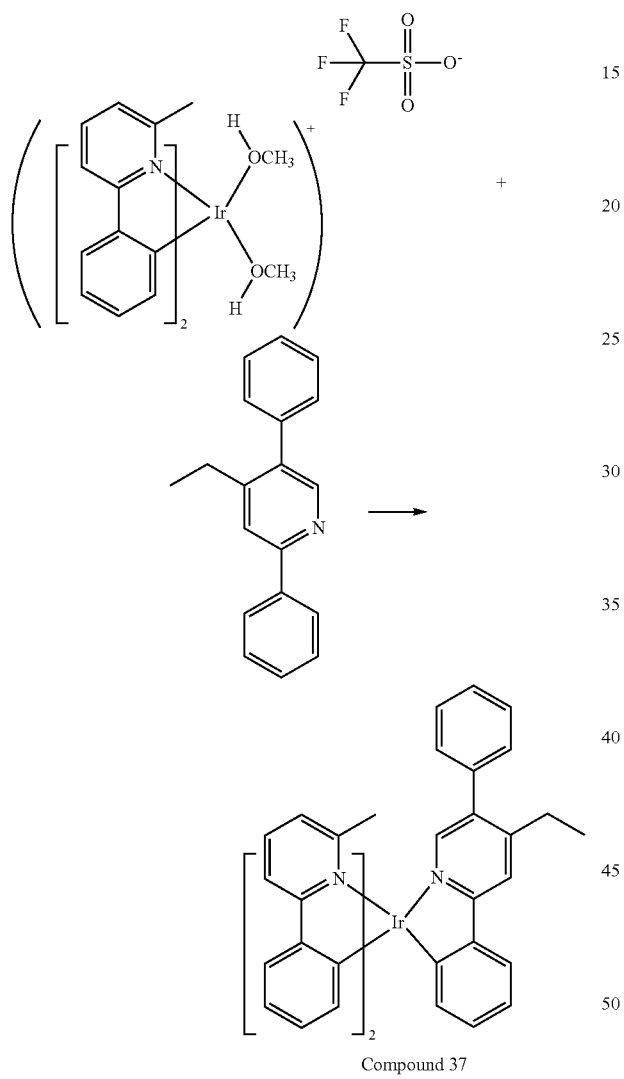

Compound 37

Synthesis of Compound 37

The iridium triflate (2.45 g) and 2,5-diphenyl-4-ethylpyridine (2.58 g) was placed in a 250 mL round bottom flask. 50 mL of ethanol was added and the mixture was refluxed for 16 h. Celite was added to the cooled solution and the mixture was poured onto a 2 inch bed of silica gel. The silica bed was then washed twice with ethanol (2×50 mL), followed by hexanes (2×50 mL). The product was then eluted through the silica plug with dichloromethane. The dichloromethane was removed under vacuum to give the desired compound. The compound was further purified by column chromatography using silica gel as the stationary phase and 1:1 dichloromethane/hexanes as the mobile phase. 1.25 g of desired product was obtained after purification (48% yield).

Device Examples

All device examples were fabricated by high vacuum (<$10^{-7}$ Torr) thermal evaporation. The anode electrode is 1200 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

Figure 3:
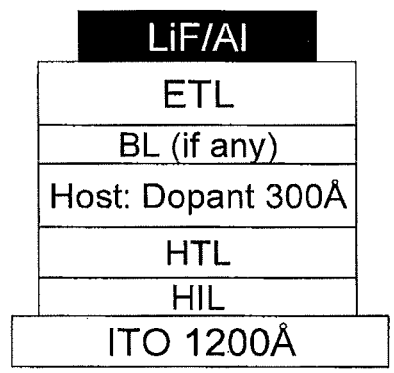
FIG. 3 shows a PHOLED having a particular structure.

The organic stack of the Device Examples 1 and 2 in Table 2, consisted of sequentially, from the ITO surface, 100 Å of E1 as the hole injection layer (HIL), 300 Å of 4,4'-bis[N-(1-naphthyl)-N-phenylamino]biphenyl (α-NPD) as the hole transporting later (HTL), 300 Å of H1 doped with 7% or 10% of Compound 1 as the emissive layer (EML), 50 Å of H1 as the blocking layer, and 400 Å of $Alq_3$ (tris-8-hydroxyquinoline aluminum) as the ETL. The device structure of the Device Examples is also summarized in FIG. 3.

Comparative Examples 1 and 2 were fabricated similarly to the Device Examples, except that E1 was used as the emissive dopant.

The device structures and data are summarized in Table 2 and Table 3. Table 2 shows device structure, and Table 3 shows the corresponding measured results for those devices. As used herein, E1, H1 and NPD, have the following structures:

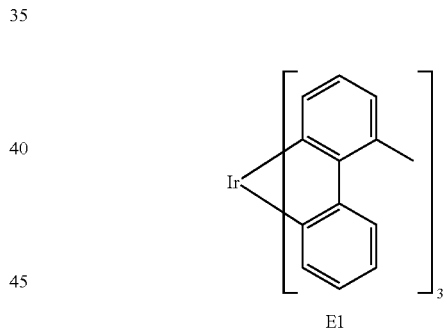

E1

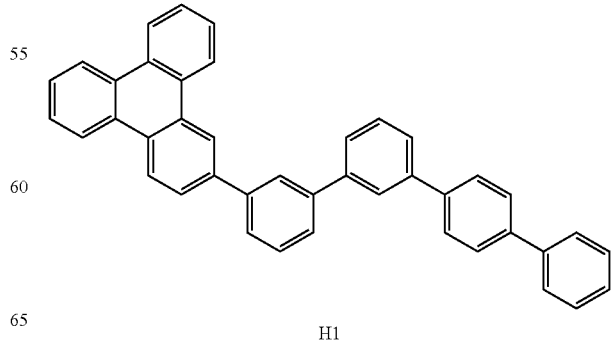

H1

-continued

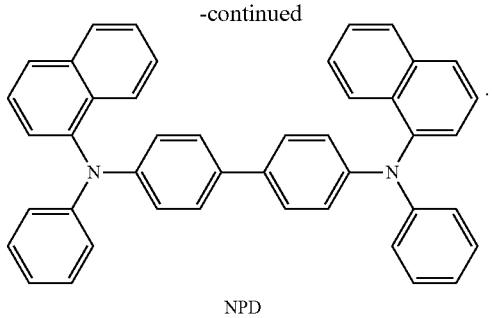

NPD

10% or 15% of an invention compound as the emissive layer (EML), 50 Å of H1 or H2 as the blocking layer, and 400 Å of Alq$_3$ (tris-8-hydroxyquinoline aluminum) as the ETL. The device structure of the Device Examples is also summarized in FIG. 3.

Comparative Example 3 was fabricated similarly to the Device Examples, except that E1 was used as the emissive dopant.

The device structures and data are summarized in Table 4 and Table 5. Table 4 shows device structure, and Table 5 shows the corresponding measured results for those devices. As used herein, E1, H1, H2 and NPD, have the following structures:

TABLE 2

| Device Example | HIL | HTL | Host | Dopant % | BL | ETL |
|---|---|---|---|---|---|---|
| 1 | E1 100 Å | NPD 300 Å | H1 | Compound 1 7% | H1 50 Å | Alq$_3$ 450 Å |
| Comparative Example 1 | E1 100 Å | NPD 300 Å | H1 | E1 7% | H1 50 Å | Alq$_3$ 450 Å |
| 2 | E1 100 Å | NPD 300 Å | H1 | Compound 1 10% | H1 50 Å | Alq$_3$ 450 Å |
| Comparative Example 2 | E1 100 Å | NPD 300 Å | H1 | E1 10% | H1 50 Å | Alq$_3$ 450 Å |

TABLE 3

| | | | At 1000 cd/m$^2$ | | | | At J = 40 mA/cm$^2$ | | |
|---|---|---|---|---|---|---|---|---|---|
| | $\lambda_{max}$ | CIE | | V | LE | EQE | PE | L$_0$ | RT$_{80\%}$ | RT$_{50\%}$ |
| Ex. | (nm) | X | Y | (V) | (cd/A) | (%) | (lm/W) | (cd/m$^2$) | (hr) | (hr) |
| 1 | 558 | 0.440 | 0.546 | 6.2 | 64.4 | 19.2 | 32.6 | 18,504 | 265 | 900 |
| Comp. Ex. 1 | 528 | 0.355 | 0.607 | 6 | 53.4 | 14.7 | 27.9 | 15,985 | 214 | 760 |
| 2 | 560 | 0.449 | 0.537 | 6 | 59.5 | 18.2 | 31.1 | 19,320 | 400 | 1400 |
| Comp. Ex. 2 | 529 | 0.357 | 0.607 | 5.9 | 53.2 | 14.6 | 28.3 | 16,781 | 340 | 1130 |

From the Device Examples in Table 3, it can be seen that devices containing the inventive compound may have particularly good properties. Specifically, devices having an emissive layer containing Compound 1 as the emissive dopant. These devices demonstrate that Compound 1 may be beneficial to device stability. In particular, Comparative Example 1 and Device Example 1 have RT$_{80\%}$ (defined as the time taken for the initial luminance, L$_0$, to drop to 80% of its initial luminance) of 760 and 900 h, respectively. Comparative Example 2 and Device Example 2 have RT$_{80\%}$ of 1130 and 1400 h, respectively. These results indicate that extended conjugation of heteroleptic Ir (III) complexes may be beneficial to device stability.

Low evaporation temperature is desirable for OLED manufacturing. Prolonged heating of the materials is required during OLED manufacturing, so materials having a low evaporation temperature have less thermal stress typically resulting in cleaner evaporations. The extended conjugation achieved by adding a phenyl to the heteroatomic ring of Compound 1 results in a low sublimation temperature. Therefore, devices with Compound 1 may have improved manufacturing.

The organic stack of the Device Examples 3-12 in Table 4, consisted of sequentially, from the ITO surface, 100 Å of E1 as the hole injection layer (HIL), 300 Å of 4,4'-bis[N-(1-naphthyl)-N-phenylamino]biphenyl (α-NPD) as the hole transporting later (HTL), 300 Å of H1 or H2 doped with 7%,

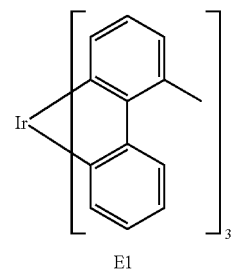

E1

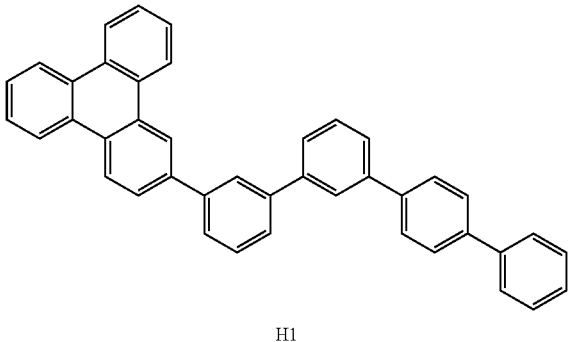

H1

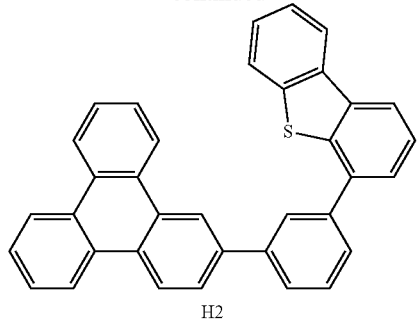

H2

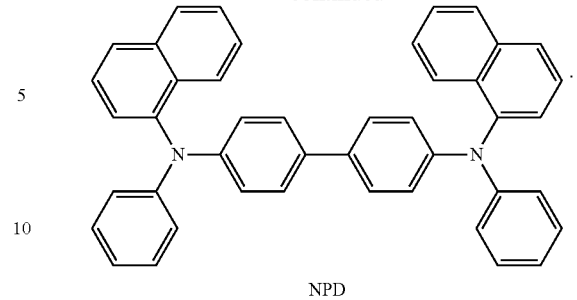

NPD

TABLE 4

| Device Example | HIL | HTL | Host | Dopant % | BL | ETL |
|---|---|---|---|---|---|---|
| Example 1 | E1 100 Å | NPD 300 Å | H1 | Compound 1 7% | H1 50 Å | $Alq_3$ 450 Å |
| Example 2 | E1 100 Å | NPD 300 Å | H1 | Compound 1 10% | H1 50 Å | $Alq_3$ 450 Å |
| Example 3 | E1 100 Å | NPD 300 Å | H2 | Compound 2 7% | H2 100 Å | $Alq_3$ 400 Å |
| Example 4 | E1 100 Å | NPD 300 Å | H2 | Compound 2 10% | H2 100 Å | $Alq_3$ 400 Å |
| Example 5 | E1 100 Å | NPD 300 Å | H2 | Compound 8 7% | H2 100 Å | $Alq_3$ 400 Å |
| Example 6 | E1 100 Å | NPD 300 Å | H2 | Compound 8 10% | H2 100 Å | $Alq_3$ 400 Å |
| Example 7 | E1 100 Å | NPD 300 Å | H2 | Compound 9 7% | H2 100 Å | $Alq_3$ 400 Å |
| Example 8 | E1 100 Å | NPD 300 Å | H2 | Compound 9 10% | H2 100 Å | $Alq_3$ 400 Å |
| Example 9 | E1 100 Å | NPD 300 Å | H2 | Compound 10 7% | H2 100 Å | $Alq_3$ 400 Å |
| Example 10 | E1 100 Å | NPD 300 Å | H2 | Compound 10 10% | H2 100 Å | $Alq_3$ 400 Å |
| Example 11 | E1 100 Å | NPD 300 Å | H2 | Compound 11 7% | H2 100 Å | $Alq_3$ 400 Å |
| Example 12 | E1 100 Å | NPD 300 Å | H2 | Compound 11 10% | H2 100 Å | $Alq_3$ 400 Å |
| Example 13 | E1 100 Å | NPD 300 Å | H2 | Compound 12 7% | H2 100 Å | $Alq_3$ 400 Å |
| Example 14 | E1 100 Å | NPD 300 Å | H2 | Compound 12 10% | H2 100 Å | $Alq_3$ 400 Å |
| Example 15 | E1 100 Å | NPD 300 Å | H2 | Compound 12 15% | H2 100 Å | $Alq_3$ 400 Å |
| Comparative Example 1 | E1 100 Å | NPD 300 Å | H1 | E1 7% | H1 50 Å | $Alq_3$ 450 Å |
| Comparative Example 2 | E1 100 Å | NPD 300 Å | H1 | E1 10% | H1 50 Å | $Alq_3$ 450 Å |
| Comparative example 3 | E1 100 Å | NPD 300 Å | H2 | E1 7% | H2 100 Å | $Alq_3$ 400 Å |

TABLE 5

| | CIE | | At 1000 $cd/m^2$ | | | | At J = 40 $mA/cm^2$ | | |
|---|---|---|---|---|---|---|---|---|---|
| Ex. | λ max, nm | X | Y | V (V) | LE (cd/A) | EQE (%) | PE (lm/W) | Lo, ($cd/m^2$) | $RT_{80\%}$, (hr) | $RT_{50\%}$, (hr) |
| Ex. 1 | 558 | 0.440 | 0.546 | 6.2 | 64.4 | 19.2 | 32.6 | 8,504 | 265 | 900 |
| Ex. 2 | 560 | 0.449 | 0.537 | 6 | 59.5 | 18.2 | 31.1 | 19,320 | 400 | 1400 |
| Ex. 3 | 543 | 0.417 | 0.569 | 6 | 70.5 | 19.6 | 36.9 | 19,818 | 390 | |
| Ex. 4 | 545 | 0.426 | 0.562 | 5.3 | 65.5 | 18.4 | 38.8 | 20,393 | 480 | |
| Ex. 5 | 536 | 0.383 | 0.594 | 6.4 | 48.8 | 13.3 | 24.1 | 14,056 | 440 | |
| Ex. 6 | 537 | 0.388 | 0.590 | 6.4 | 42.4 | 11.6 | 20.9 | 13,158 | 440 | |
| Ex. 7 | 532 | 0.367 | 0.602 | 6.3 | 51.4 | 14.1 | 25.6 | 14,637 | 305 | |
| Ex. 8 | 533 | 0.37 | 0.602 | 6 | 42.7 | 11.7 | 22.5 | 13,031 | 340 | |
| Ex. 9 | 532 | 0.376 | 0.598 | 5.7 | 59.2 | 16.3 | 32.6 | 16,212 | 225 | |
| Ex. 10 | 533 | 0.378 | 0.597 | 5.2 | 58.2 | 16 | 35.1 | 17,151 | 240 | |
| Ex. 11 | 541 | 0.411 | 0.575 | 5.5 | 73.7 | 20.3 | 42.2 | 21,430 | 335 | |
| Ex. 12 | 545 | 0.420 | 0.568 | 4.9 | 76 | 21.1 | 48.6 | 24,136 | 480 | |
| Ex. 13 | 525 | 0.342 | 0.612 | 5.8 | 56.9 | 15.8 | 30.7 | 15,843 | 208 | |
| Ex. 14 | 527 | 0.337 | 0.619 | 5 | 62.9 | 17.2 | 39.5 | 18,952 | 330 | |
| Ex. 15 | 528 | 0.349 | 0.611 | 5 | 55.7 | 15.3 | 34.8 | 17,941 | 320 | |
| Comp. Ex. 1 | 528 | 0.355 | 0.607 | 6 | 53.4 | 14.7 | 27.9 | 15,985 | 214 | 760 |
| Comp. Ex. 2 | 529 | 0.357 | 0.607 | 5.9 | 53.2 | 14.6 | 28.3 | 16,781 | 340 | 1130 |
| Comp. Ex. 3 | 528 | 0.361 | 0.601 | 6.5 | 52.1 | 14.6 | 25.2 | 14,768 | 250 | |

From the Device Examples in Table 4, it can be seen that devices containing the inventive compound may have particularly good properties. Specifically, devices having an emissive later containing Compound 1, Compound 2, Compound 8-12 as the emissive dopant demonstrate that these inventive compounds may be beneficial to device stability.

Particular devices are provided wherein inventive compounds, Compound 21 through Compound 35, are the emitting dopant and H-2 is the host. The organic stack of the Device Examples 21-35 consisted of sequentially, from the ITO surface, 100 Å of E1 as the hole injection layer (HIL), 300 Å of 4,4'-bis[N-(1-naphthyl)-N-phenylamino]biphenyl (α-NPD) as the hole transporting later (HTL), 300 Å of 112 doped with 7% of Compound 21-35 and 37 as the emissive layer (EML), 100 Å of H2 as the electron transporting layer (ETL2), and 400 Å of Alq$_3$ (tris-8-hydroxyquinoline aluminum) as the electron transporting layer (ETL1).

Comparative Device Examples 4-6 were fabricated similarly to the Device Examples, except E2 was used the emitting dopant in Comparative Device Example 4; CBP was as the host, E3 was used as the emitting dopant, and 50 Å of HPT was used as the ETL2 and 450 Å of Alq$_3$ was used as the ETL1 in Comparative Device Example 5; in E4 was used as the emitting dopant in Comparative Device Example 6.

As used herein, the following compounds have the following structures:

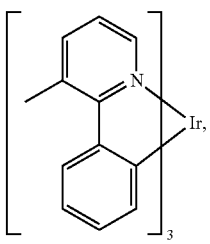

E1

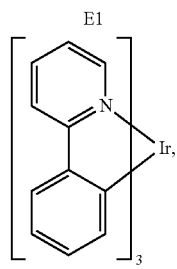

E2

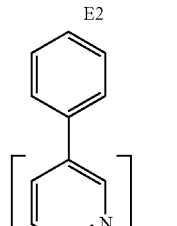

E3

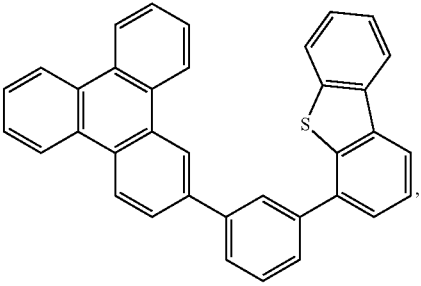

E4

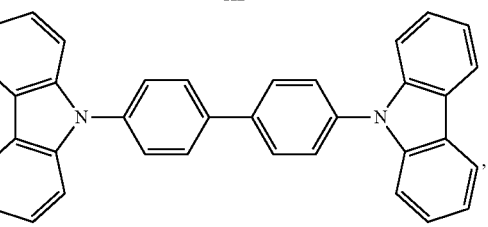

H2

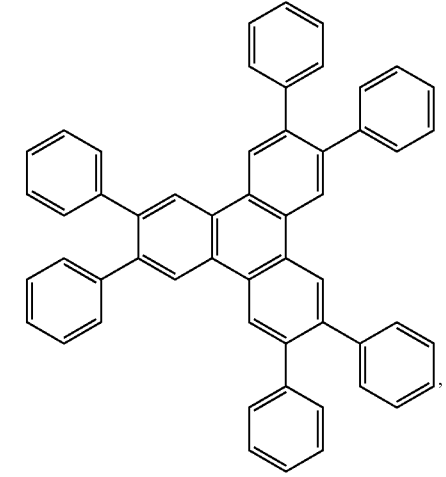

CBP

HPT

Particular materials for use in an OLED are provided. The materials may be used an emitting dopant in the emissive layer of such a device. The materials provided herein may be used to provide devices having high efficiency and a narrow electroluminescence. In addition, these materials may provided improved stability and improved processability, such as high solubility and low evaporation temperature.

TABLE 6

| Device Example | Compound | Evaporation temperature (° C.) |
|---|---|---|
| Example 16 | 21 | 239 |
| Example 17 | 22 | 232 |
| Example 18 | 23 | 250 |
| Example 19 | 25 | 216 |
| Example 20 | 26 | 202 |
| Example 21 | 27 | 205 |
| Example 22 | 28 | 208 |
| Example 23 | 29 | 204 |
| Example 24 | 30 | 203 |
| Example 25 | 31 | 213 |
| Example 26 | 32 | 209 |
| Example 27 | 34 | 236 |
| Example 28 | 35 | 216 |
| Example 29 | 37 | 202 |
| Comparative example 4 | E2 | 230 |
| Comparative example 5 | E3 | 270 |
| Comparative example 6 | E4 | 204 |

TABLE 7

| Device Example | CIE | | | |
|---|---|---|---|---|
| | $\lambda_{max}$ (nm) | FWHM (nm) | x | y |
| Example 16 | 526 | 68 | 0.337 | 0.623 |
| Example 17 | 528 | 64 | 0.342 | 0.622 |
| Example 18 | 520 | 66 | 0.324 | 0.622 |
| Example 27 | 532 | 68 | 0.368 | 0.607 |
| Comparative example 4 | 519 | 74 | 0.321 | 0.621 |
| Comparative example 5 | 548 | 70 | 0.43 | 0.56 |
| Comparative example 6 | 520 | 74 | 0.320 | 0.632 |

Table 7 shows additional device data for Device Examples and Comparative Examples. In particular, Table 7 provides $\lambda_{max}$ and CIE coordinates for Device Examples 16-18 and 27 compared to the Comparative Device Examples 4, 5 and 6. From the data, it can be seen that Device Examples 16-18 and 27 are significantly blue shifted from Comparative Device Example 5. This result suggests that the conjugation may be reduced by the presence of the twisted phenyl C-ring.

TABLE 8

| | CIE | | | | At 1000 cd/m² | | | | At J = 40 mA/cm² | |
|---|---|---|---|---|---|---|---|---|---|---|
| Ex. | $\lambda_{max}$ | FWHM (nm) | x | y | V (V) | LE (cd/A) | EQE (%) | PE (lm/W) | LE EQE | $L_o$ (cd/m²) | $RT_{80\%}$ (h) |
| 16 | 526 | 68 | 0.337 | 0.623 | 6.9 | 49.3 | 13.3 | 22.4 | 3.7 | 16,895 | 210 |
| 17 | 528 | 64 | 0.342 | 0.622 | 6.0 | 55.1 | 14.8 | 28.7 | 3.7 | 18,175 | 260 |
| 18 | 520 | 66 | 0.324 | 0.622 | 6.9 | 43.7 | 12.0 | 19.9 | 3.6 | 16,240 | 54 |
| 19 | 532 | 72 | 0.372 | 0.599 | 5.4 | 65.6 | 17.8 | 38.0 | 3.7 | 18,482 | 245 |
| 20 | 532 | 70 | 0.36 | 0.608 | 5.6 | 69 | 18.6 | 39 | 3.7 | 19,934 | 142 |
| 21 | 538 | 82 | 0.371 | 0.594 | 5.8 | 59.8 | 16.6 | 32.2 | 3.6 | 17,658 | 174 |
| 22 | 532 | 74 | 0.346 | 0.613 | 7.1 | 59.7 | 16.2 | 26.5 | 3.7 | 14,187 | 90 |
| 23 | 528 | 70 | 0.345 | 0.616 | 5.4 | 62.5 | 17 | 36.5 | 3.7 | 19,280 | 237 |
| 24 | 522 | 70 | 0.327 | 0.623 | 5.4 | 63.3 | 17.3 | 36.7 | 3.7 | 18,212 | 223 |
| 25 | 528 | 70 | 0.342 | 0.618 | 5.2 | 66.6 | 18.1 | 40.5 | 3.7 | 19,280 | 254 |
| 26 | 532 | 74 | 0.369 | 0.600 | 5.9 | 59.7 | 16.3 | 31.6 | 3.7 | 16,240 | 42 |
| 27 | 532 | 72 | 0.361 | 0.608 | 4.9 | 59.6 | 16.0 | 43.2 | 3.7 | 20,057 | 290 |
| 28 | 532 | 68 | 0.368 | 0.607 | 5.2 | 67.6 | 18 | 40.6 | 3.8 | 20,324 | 200 |
| 29 | 522 | 72 | 0.333 | 0.619 | 5.6 | 62.7 | 17.2 | 35.0 | 3.6 | 17,205 | 121 |
| Comp. 4 | 519 | 74 | 0.321 | 0.621 | 6 | 45.1 | 12.6 | 23.6 | 3.6 | 13,835 | 196 |
| Comp. 6 | 520 | 74 | 0.320 | 0.632 | 5.5 | 54.9 | 14.9 | 31.2 | 3.7 | 17,153 | 42 |

Table 6 shows the evaporation temperature of the emitting compounds, Compounds 21-33, used in the Device Examples compared to the evaporation temperatures of the emitting compounds E2 and E3 used in Comparative Device Examples 4 and 5, respectively. In particular, Compounds 21-24 have significantly lower evaporation temperatures than E3. A lower evaporation temperature may be a desirable property for the thermal evaporation and long term thermal stability of dopants. It is believed that the C-ring phenyl-pyridine in Compounds 21-23 has more twist between the two rings than the phenyl-pyridine twist, as is present in E3. The heteroleptic compounds (Compounds 25-33 and 37) which contain the twisted C-ring feature have similar or lower evaporation temperatures than E2 which does not have a C-ring at all. The result indicates that the twisted C-ring feature may lower evaporation temperature while keeping the molecular weight as high or even higher than the structurally similar compounds without this feature.

Table 8 provides a comparison of device properties between Device Examples 16-29 and Comparative Examples 4 and 6. From the data, it can be seen that Device Examples 16 (Compound 21), 17 (Compound 22), 19 (Compound 25), 20 (Compound 26), 21 (Compound 27), 23 (Compound 29), 24 (Compound 30), 25 (Compound 31), 27 (Compound 34), 28 (Compound 25), 29 (Compound 37) provide high efficiency and long device lifetime. Particularly, Device Examples 16, 17, 19, 23, 24, 25 and 27, which use Compounds 21, 22, 25, 29, 30, 31 and 34 respectively as the emitting dopant, have very good device performance. These particular devices show an $RT_{80\%}$ (defined as the time required for the initial luminance $L_0$ to drop to from 100% to 80% at room temperature under constant DC drive) of 210, 260, 245 237, 223, 254 and 290 h compared to an $RT_{80\%}$ of 196 h of Comparative Device Example 4. Furthermore, Device Examples 16, 17, 19, 23, 24, 25 and 27 all operate at higher $L_0$ than Comparative Device Example 4. The result indicates that the phenyl C-ring may improve the device stability by adding some conjugation to emitting dopant. However, the conjugation is limited by the presence of the twist feature, described above, which does not cause significant red-shift in emission compared to a phenyl in regular conjugation as in E-3. In addition, the EL spectra of Device Examples 16-20, 23-25 and 27-29 are all narrower than that of Comparative Example 4. Narrow emission may be an desirable factor for achieving saturated color coordinates, high LE:EQE conversion, microcavity tuning, and color filter matching in OLED technology.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A method for making a homoleptic Ir(III) complex, comprising:

reacting

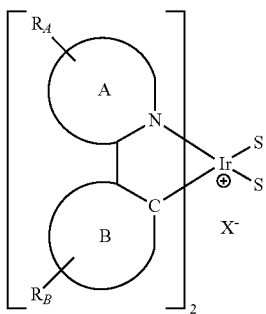

with

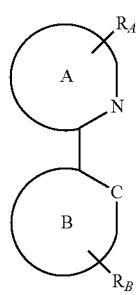

in the presence of a low boiling alcohol to form

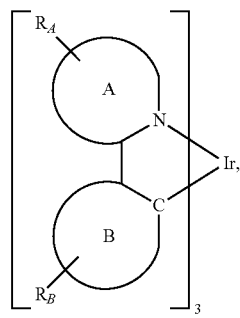

wherein at least one of $R_A$ and $R_B$ is an alkyl group and the alkyl group is not adjacent to the nitrogen on the pyridine ring;

wherein S is a neutral ligand;

wherein X is a counterion;

wherein A is a pyridine ring and B is a phenyl ring;

wherein A-B represents a bonded pair of carbocyclic or heterocyclic rings coordinated to the iridium via a nitrogen atom on ring A and an $sp^2$ hybridized carbon atom on ring B;

wherein each of $R_A$, and $R_B$ may represent mono, di, tri, or tetra substitutions; and wherein $R_A$ and $R_B$, are each independently selected from the group consisting of hydrogen, alkyl, alkoxy, amino, alkenyl, alkynyl, arylkyl, aryl, and heteroaryl.

2. The method of claim 1, wherein the low boiling alcohol is selected from the group consisting of methanol, ethanol, n-propanol, isopropanol, n-butanol, 1:1 ratio of ethanol and methanol, 2-methoxyethanol, and 2-ethoxyethanol.

3. The method of claim 1, wherein A is

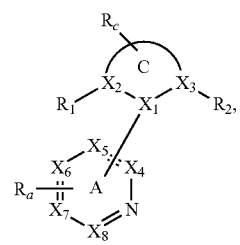

wherein C is a 5 or 6-membered aryl or heteroaryl ring;

wherein A-C represents a bonded pair of rings;

wherein $R_A$ and $R_C$ may represent mono, di, tri, or tetra substitutions;

wherein $R_A$ and $R_C$ are independently selected from the group consisting of hydrogen, alkyl, alkoxy, amino, alkenyl, alkynyl, arylkyl, aryl, and heteroaryl;

wherein each of $X_1$, $X_2$, and $X_3$ is independently selected from carbon and nitrogen;

wherein each of $X_4$, $X_5$, $X_6$, $X_7$, and $X_8$ is carbon;

wherein $R_1$ and $R_2$ are independently selected from the group consisting of hydrogen, alkyl, alkoxy, amino, alkenyl, alkynyl, arylkyl, aryl, and heteroaryl; and wherein at least one of $R_1$, $R_2$, and an $R_a$ substituent adjacent to a bond with $X_1$ is not hydrogen.

4. The method of claim 1, wherein X is triflate.
5. The method of claim 1, comprising:
reacting
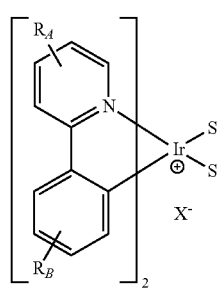
with
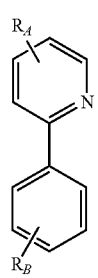
in the presence of a low boiling alcohol to form
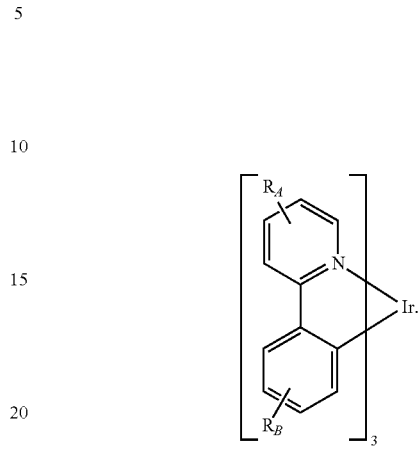
* * * * *